US012616463B2

(12) United States Patent
Heneveld et al.

(10) Patent No.: US 12,616,463 B2
(45) Date of Patent: May 5, 2026

(54) MULTI-FUNCTION SYSTEMS, APPARATUS AND METHODS FOR APPROXIMATING, LIGATING AND FIXATING SOFT TISSUE

(71) Applicant: Passer Stitch, LLC, Henderson, NV (US)

(72) Inventors: Scott Heneveld, Whitmore, CA (US); John Valadez, Agua Dulce, CA (US); Christopher Morris, Santa Clarita, CA (US); Justin Anderson, Henderson, NV (US); Brad Topper, Santa Clarita, CA (US); Jeffrey Sonntag, South Bend, IN (US)

(73) Assignee: Passer Stitch, LLC, Henderson, NV (US)

( * ) Notice: Subject to any disclaimer, the term of this patent is extended or adjusted under 35 U.S.C. 154(b) by 0 days.

(21) Appl. No.: 19/330,007

(22) Filed: Sep. 16, 2025

(65) Prior Publication Data

US 2026/0000394 A1     Jan. 1, 2026

Related U.S. Application Data

(63) Continuation-in-part of application No. 19/271,062, filed on Jul. 16, 2025, which is a continuation of application No. 18/623,903, filed on Apr. 1, 2024, now Pat. No. 12,390,213.

(60) Provisional application No. 63/766,960, filed on Mar. 4, 2025, provisional application No. 63/602,605, filed (Continued)

(51) Int. Cl.
A61B 17/04      (2006.01)
A61B 17/06      (2006.01)
*A61B 17/00*      (2006.01)
*A61B 17/29*      (2006.01)

(52) U.S. Cl.
CPC ..................... *A61B 17/0469* (2013.01); *A61B 2017/00367* (2013.01); *A61B 2017/047* (2013.01); *A61B 2017/2925* (2013.01); *A61B 2017/2926* (2013.01)

(58) Field of Classification Search
CPC .... A61B 2017/047; A61B 2017/00367; A61B 2017/2925; A61B 2017/2926; A61B 2017/2936; A61B 2017/2933; A61B 2017/2934; A61B 2017/2944; A61B 2017/294; A61B 17/0469; A61B 17/0483;

(Continued)

(56) References Cited

U.S. PATENT DOCUMENTS 8,177,796 B2    5/2012   Akyuz et al.
10,383,621 B2   8/2019   Gregoire et al.

(Continued)

*Primary Examiner* — Tuan V Nguyen
(74) *Attorney, Agent, or Firm* — Francis Law Group

(57) ABSTRACT

A system for passing suture into and through soft tissue that includes a multi-function jaw mechanism, and a needle adapted to engage a suture and pierce into the soft tissue. The multi-function jaw mechanism adapted to capture the soft tissue, provide highly reliable suture loading and retrieval with minimal visual guidance, and measure stitch placement positions in the soft tissue in a confined surgical site for accurate and precise provision of complex stitch patterns. The system also includes system control means for synchronizing articulation of the jaw mechanism, articulation of the needle, and engagement of the suture by the needle and release of the suture therefrom.

16 Claims, 37 Drawing Sheets

Related U.S. Application Data on Nov. 26, 2023, provisional application No. 63/456,513, filed on Apr. 2, 2023.

(58) Field of Classification Search
CPC .......... A61B 17/0482; A61B 17/06004; A61B 17/06066
See application file for complete search history.

(56) References Cited

U.S. PATENT DOCUMENTS

| | | | |
|---|---|---|---|
| 2011/0118760 A1* | 5/2011 | Gregoire ............ | A61B 17/0469 606/145 |
| 2017/0172565 A1 | 6/2017 | Heneveld | |
| 2018/0235601 A1 | 8/2018 | Malkowski et al. | |
| 2019/0167257 A1* | 6/2019 | Heneveld ......... | A61B 17/06004 |
| 2020/0093479 A1 | 3/2020 | Murillo et al. | |
| 2020/0360012 A1 | 11/2020 | Heneveld | |
| 2021/0000463 A1 | 1/2021 | Murillo et al. | |

* cited by examiner (7°rotation)

(40°rotation)

FIG. 6A          FIG. 6B

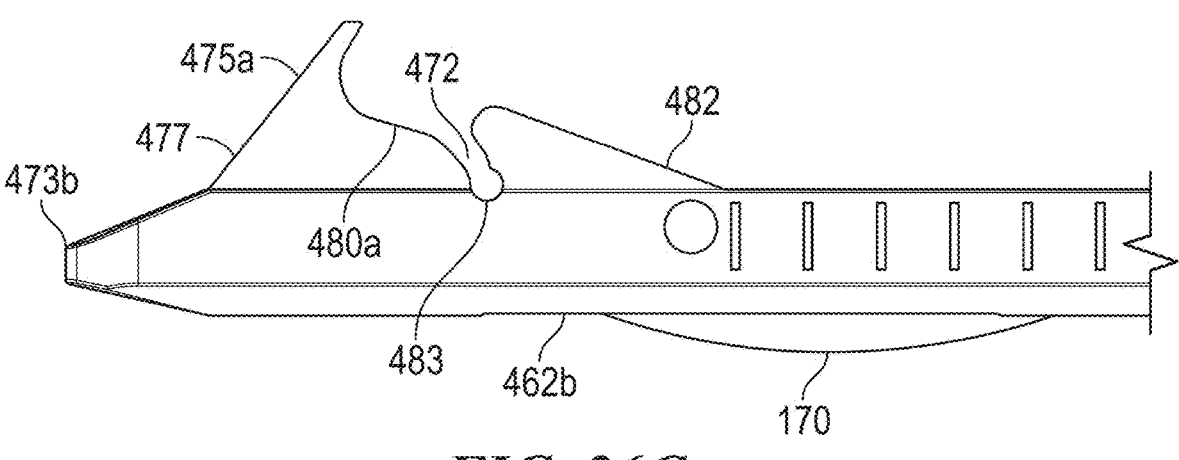
FIG. 26C
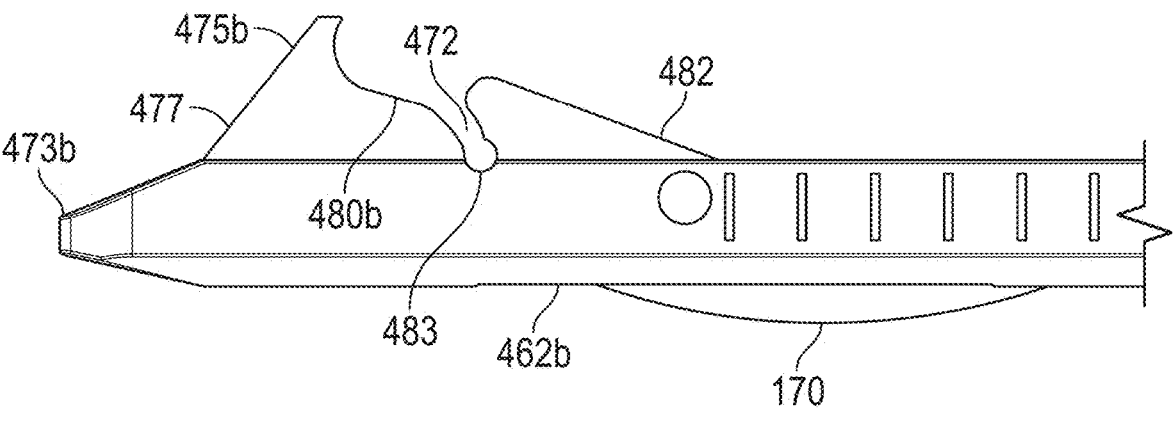
FIG. 26D
FIG. 26E

MULTI-FUNCTION SYSTEMS, APPARATUS AND METHODS FOR APPROXIMATING, LIGATING AND FIXATING SOFT TISSUE

CROSS-REFERENCES TO RELATED APPLICATIONS

This application claims the benefit of U.S. Provisional Application No. 63/766,960, filed on Mar. 4, 2025, and is a continuation-in-part of U.S. application Ser. No. 19/271, 062, filed on Jul. 16, 2025, which is a continuation of U.S. application Ser. No. 18/623,903, filed on Apr. 1, 2024, now U.S. Pat. No. 12,390,213, which claims the benefit of U.S. Provisional Application No. 63/456,513, filed on Apr. 2, 2023, and U.S. Provisional Application No. 63/602,605, filed on Nov. 26, 2023.

FIELD OF THE INVENTION

The present invention relates to multi-function systems, apparatus and associated methods for approximating, ligating and fixating soft tissue; particularly, soft tissue that is accessed via an endoscopic procedure.

BACKGROUND OF THE INVENTION

As is well established, approximating, ligating and fixating soft tissue, such as fascia, muscles, ligaments and tendons, is a fundamental aspect of many surgical procedures. The process of approximating, ligating and fixating soft tissue often involves passing suture through the soft tissue with a suture passing system or device.

Various suture passing systems and devices have thus been developed and employed to pass suture through soft tissue, such as the device disclosed in U.S. Pat. No. 10,383, 621 to Gregoire, et al. The Gregoire, et al. device, as well as most conventional suture passing devices, include an elongated shaft and a low-profile distal jaw mechanism that is adapted to be advanced into a surgical site via access cannula in minimally invasive surgical procedures. The jaw mechanism typically comprises top and bottom jaw members that are adapted to capture and position the soft tissue for passage of a suture therethrough.

Conventional suture passing systems and devices also typically comprise means for positioning and capturing a portion of a suture and retracting the suture into the device after it is passed through soft tissue. Such means typically comprises a bendable needle having a suture capture end that is advanced into and through elongated shaft of the device and through a distal opening in the bottom jaw member.

Several conventional suture passing systems also include suture retainment means that is adapted and configured to retain a portion of suture (usually in a top jaw member of a jaw mechanism) after the portion of suture has been drawn through soft tissue for manipulation by the system in a surgical site, e.g., forming a particular suture pattern.

Although many conventional suture passing systems can effectively be employed to pass suture into and through soft tissue in a surgical site and retain a portion of the suture after passage through soft tissue, there are numerous drawbacks and disadvantages associated with the use of conventional suture passing systems and associated devices to approximate, ligate and fixate soft tissue.

Major drawbacks and disadvantages associated with most conventional suture passing systems include difficultly manipulating soft tissue in a confined surgical site, cumbersome operation and, often complicated and sight dependent, suture loading procedures, and difficulty manipulating and retrieving suture in a confined surgical site.

A further major drawback and disadvantage associated with conventional suture passing systems is that such systems are typically devoid of any means for effectively engaging and capturing soft tissue or a portion thereof (prior to or after passing suture therethrough) and surgical instruments in a surgical site during a surgical procedure.

Yet another major drawback and disadvantage associated with conventional suture passing systems is that such systems are also devoid of any means for measuring stitch placement positions in soft tissue to accurately produce complex stitch patterns, such as modified Mason-Allen stitch patterns. The conventional systems solely rely on visual guidance by an operator to produce common and complex stitch patterns, which significantly limits a surgeon's ability to consistently provide precise stitch patterns.

Difficulties with manipulation of soft tissue and the absence of any means for measuring stitch placement positions in soft tissue also limits the types of soft tissue that can be approximated and fixated by the conventional suture passing systems.

A further drawback and disadvantage associated with conventional suture passing systems is that such systems are also typically devoid of any means for protecting the needles employed therewith from breakage in a surgical site during a surgical procedure, e.g., breakage resulting from contact with hard tissue, such as bone.

A further drawback and disadvantage associated with conventional suture passing systems is that such systems typically have a limited life cycle due to needle wear and fatigue.

There is thus a need for improved suture passing systems, apparatus and methods that substantially reduce or eliminate the disadvantages and drawbacks associated with conventional suture passing systems, apparatus and methods.

It is thus an object of the present invention to provide improved suture passing systems, apparatus and methods that substantially reduce or eliminate the disadvantages and drawbacks associated with conventional suture passing systems, apparatus and methods.

It is another object of the present invention to provide improved suture passing systems, apparatus and methods systems that can be readily employed to effectively approximate, ligate, fixate soft tissue and soft tissue structures in a confined surgical site.

It is another object of the present invention to provide improved suture passing systems, apparatus and methods that can be readily employed to pass suture into and through soft tissue and soft tissue structures without collateral damage to extraneous soft tissue and bone structures.

It is another object of the present invention to provide improved suture passing systems, apparatus and methods that provide an enhanced degree of control of soft tissue and soft tissue structure engagement, needle articulation and suture manipulation by an operator with minimal complexity.

It is another object of the present invention to provide improved suture passing systems, apparatus and methods that enable an operator to load suture with greater case and efficiency compared to conventional suture passing systems.

It is another object of the present invention to provide improved suture passing systems, apparatus and methods that provide enhanced suture manipulation in a confined surgical site with minimal visual guidance.

It is another object of the present invention to provide improved suture passing systems, apparatus and methods that enable an operator to precisely measure stitch placement locations in soft tissue and soft tissue structures in a confined surgical site for accurate and precise provision of complex stitch patterns.

It is another object of the present invention to provide improved suture passing systems, apparatus and methods that can be readily employed to effectively capture and engage soft tissue, soft tissue structures, sutures and surgical instruments within a confined surgical site.

It is another object of the present invention to provide improved suture passing systems, apparatus and methods that provide enhanced needle durability over thousands of cycles of suture passing in and through soft tissue and soft tissue structures.

It is another object of the present invention to provide improved suture passing systems and apparatus that can be readily employed to endure multiple use cycles with limited impact on suture passing efficacy.

It is another object of the present invention to provide improved suture passing systems, apparatus and methods that prevent needle breakage in a surgical site during a surgical procedure.

It is another object of the present invention to provide improved suture passing systems, apparatus and methods that (i) enable an operator to load suture with greater case and efficiency compared to conventional suture passing systems, and (ii) provide enhanced suture manipulation and retrieval in a confined surgical site with minimal visual guidance, and (iii) enable an operator to precisely measure stitch placement locations in soft tissue and soft tissue structures in a confined surgical site for accurate and precise provision of complex stitch patterns, such as modified Mason-Allen stitch patterns, and (iv) can be readily employed to effectively capture and engage soft tissue, soft tissue structures and surgical instruments within a confined surgical site, and (v) provide enhanced needle durability over thousands of cycles of suture passing in and through soft tissue and soft tissue structures, and (vi) prevent needle breakage in a surgical site during a surgical procedure.

SUMMARY OF THE INVENTION

The present invention is directed to apparatus, systems and methods for approximating, ligating and fixating soft tissue and structures (referred to herein as "soft tissue").

In one embodiment of the invention there is thus provided an apparatus for approximating and fixating soft tissue, the apparatus comprises a multi-function jaw mechanism comprising top and bottom jaw members, the top jaw member adapted to axially articulate with respect to the bottom jaw member, whereby the multi-function jaw mechanism is adapted to transition from an open jaw configuration, wherein the top and bottom jaw members provide an open internal jaw region, to a closed jaw configuration, the open internal jaw region configured to receive a suture and soft tissue therein, the bottom jaw member comprising a suture engagement region disposed on the bottom jaw member distal end, the suture engagement region comprising a raised proximal guide region, a raised distal guide region and a suture loading slot disposed between the raised proximal guide region and the raised distal guide region, the suture slot comprising a suture seat, the suture loading slot sized and configured to receive the suture therein and position the suture in the suture seat, the top and bottom jaw members forming a suture containment region when the multi-function jaw mechanism is in the closed jaw configuration, the top jaw member and suture engagement region of the bottom jaw member forming a gap therebetween when the multi-function jaw mechanism is in the closed jaw configuration, the gap sized to allow distal translation of the suture into the suture containment region when the multi-function jaw mechanism is in the closed jaw configuration, the multi-function jaw mechanism forming a suture backstop region in the suture containment region when the multi-function jaw mechanism is in the closed jaw configuration, the suture backstop region configured to abate translation of the suture in a distal direction when the suture is disposed in the suture containment region.

In some embodiments, the multi-function jaw mechanism further comprises means for measuring a stitch placement location in the soft tissue when the soft tissue is positioned in the open internal jaw region of the multi-function jaw mechanism.

In some embodiments, the means for measuring a stitch placement location in the soft tissue comprises a first plurality of markers disposed on a first outer surface of the lower jaw mechanism, each of the first plurality of markers spaced a defined distance from the suture loading slot, whereby, when a border of the soft tissue is advanced into the open internal jaw region of the multi-function jaw mechanism and aligned with a first marker of the first plurality of markers, a first measurement of a first stitch placement location in the soft tissue is provided.

In one embodiment of the invention there is thus also provided a system for approximating and fixating soft tissue, the system comprising a multi-function jaw mechanism and a tissue piercing needle, the needle comprising a tissue piercing distal end configured and adapted to releasably engage a suture and pierce into and through the soft tissue with the suture engaged thereto;

the multi-function jaw mechanism comprising top and bottom jaw members that are adapted to axially articulate, whereby the multi-function jaw mechanism is adapted to transition from an open jaw configuration, wherein the top and bottom jaw members provide an open internal jaw region, to a closed jaw configuration, the open internal jaw region sized and configured to receive the suture and soft tissue therein, the bottom jaw member comprising a suture engagement region disposed on the distal end of the bottom jaw member, the suture engagement region comprising a raised proximal guide region, a raised distal guide region and a suture loading slot disposed between the raised proximal guide region and the raised distal guide region, the suture loading slot sized and configured to receive the suture therein and position the suture in the bottom jaw member for engagement by the needle, the top and bottom jaw members forming a suture containment region when the multi-function jaw mechanism is in the closed jaw configuration, the top jaw member and suture engagement region of the bottom jaw member forming a gap therebetween when the multi-function jaw mechanism is in the closed jaw configuration, the gap sized to allow distal translation of the suture into the suture containment region when the multi-function jaw mechanism is in the closed jaw configuration,

5 the multi-function jaw mechanism forming a suture back-stop region in the suture containment region when the multi-function jaw mechanism is in the closed jaw configuration, the suture backstop region configured to abate translation of the suture in a distal direction.

In a preferred embodiment, the system further comprises suture control means adapted to control access of the suture into the open internal jaw region of the multi-function jaw mechanism, the releasable engagement of the suture by the needle, and release of the suture by the needle.

In a preferred embodiment, the system further comprises system control means for synchronizing the axial articulation of the top jaw member, the needle articulation and the noted suture control means functions.

In a preferred embodiment, the multi-function jaw mechanism further comprises means for measuring a stitch placement location in the soft tissue when the soft tissue is advanced into the internal jaw region of the multi-function jaw mechanism.

In a preferred embodiment, the means for measuring a stitch placement location in the soft tissue comprises a first plurality of markers disposed on at least an outer surface of the lower jaw mechanism, each of the first plurality of markers spaced a defined distance from the suture loading slot, whereby, when a border of the soft tissue is advanced into the internal jaw region of the multi-function jaw mechanism and aligned with a first marker of the first plurality of markers, a first stitch placement location in the soft tissue can be measured and realized when the needle and engaged suture are advanced into the soft tissue.

In some embodiments, the distal ends of the top and bottom jaw members comprise tissue engaging regions that are aligned and configured to capture and engage at least a portion of the soft tissue or suture or surgical devices within a confined surgical site when the multi-function jaw mechanism transitions from the open jaw configuration to the closed jaw configuration.

In a preferred embodiment, the multi-function jaw mechanism and, thereby, suture passing system thus provides, among several seminal features, (i) uncomplicated and highly reliable suture loading with minimal visual guidance, (ii) enhanced suture manipulation and retrieval in a confined surgical site with minimal visual guidance, (iii) enables an operator to precisely measure stitch placement locations in soft tissue in a confined surgical site for accurate and precise provision of complex stitch patterns, such as modified Mason-Allen stitch patterns, and (iv) enables an operator to capture and engage soft tissue, soft tissue structures and surgical instruments within a confined surgical site.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

6

Figure 1A:
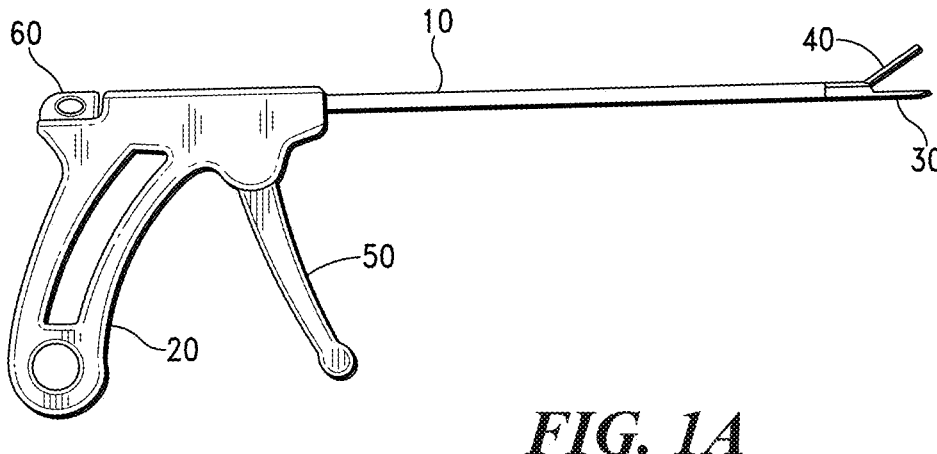
FIGS. 1A-1C are side plan views of an embodiment of a suture passing system in various stages of deployment, in accordance with the invention.
Figure 3A:
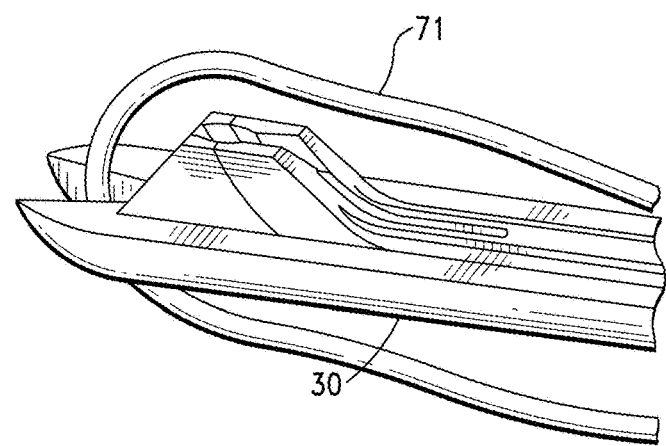
Figure 3B:
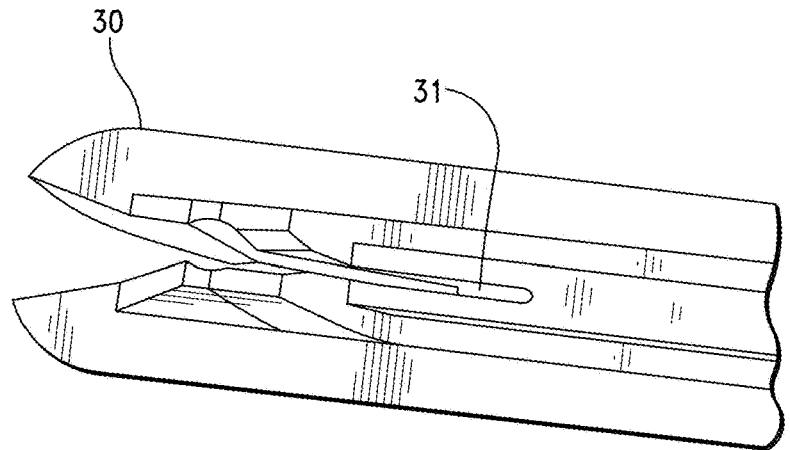
Figure 3C:
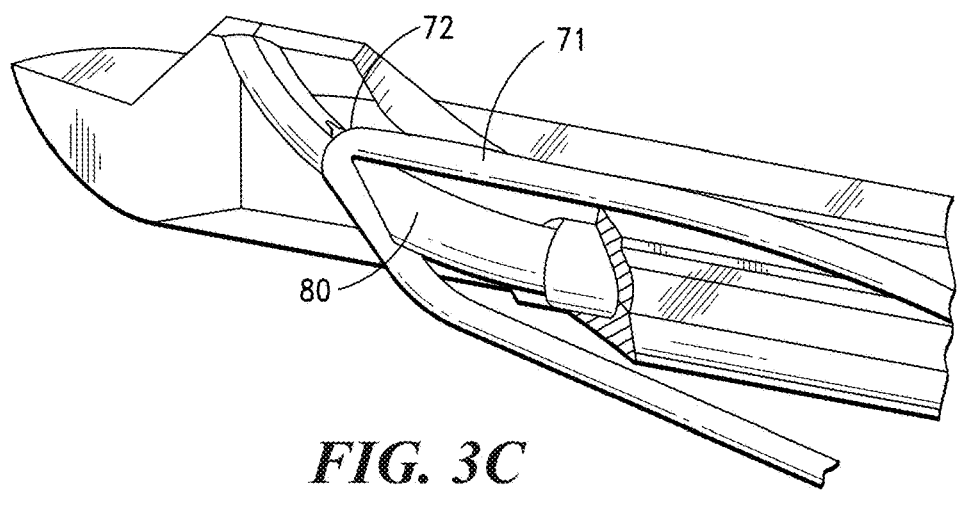
Figure 4A:
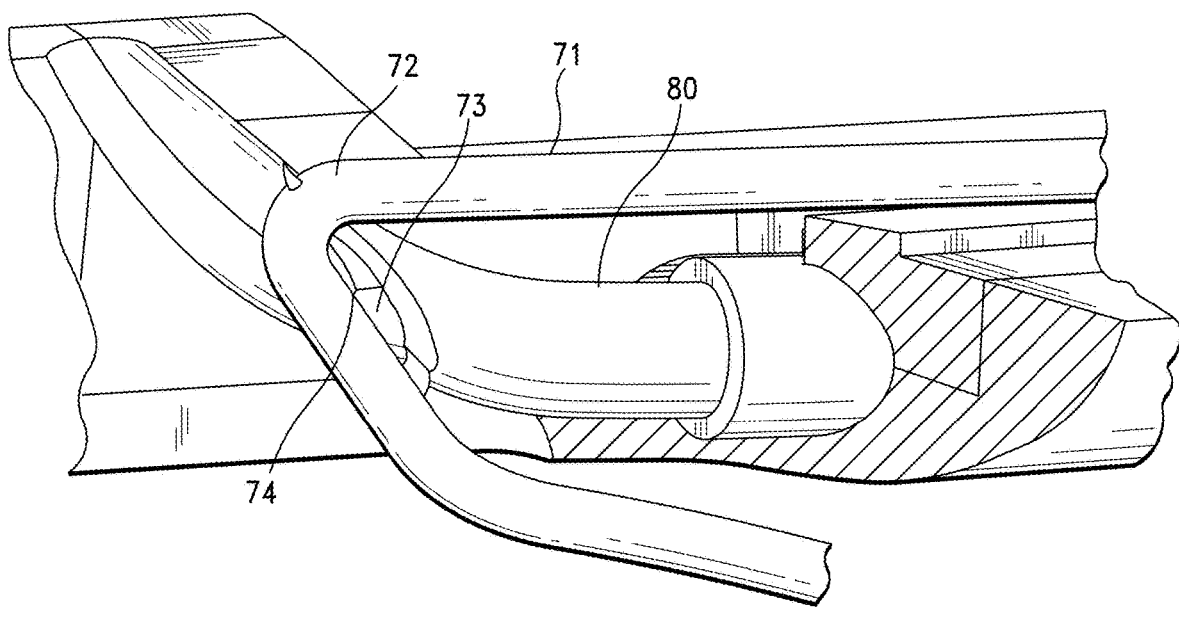
Figure 4B:
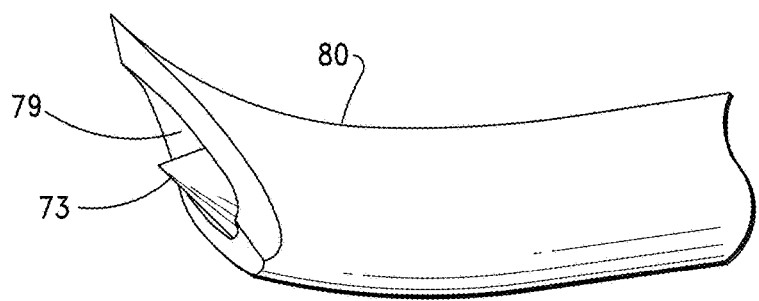
Figure 4C:
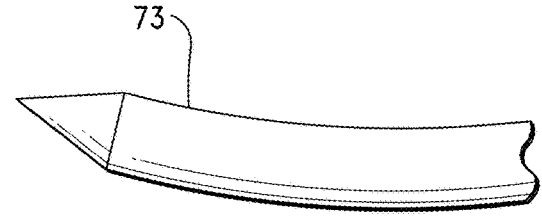
Figure 5A:
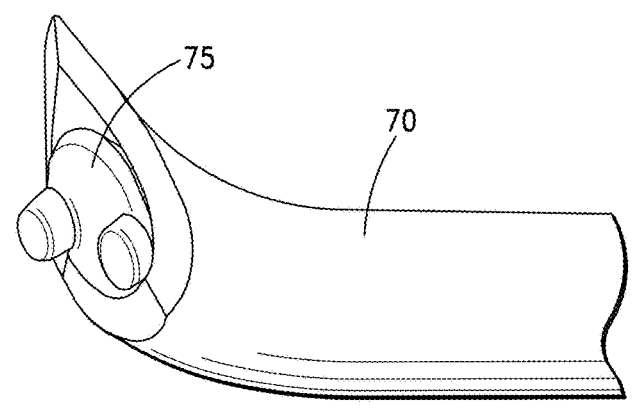
Figure 5B:
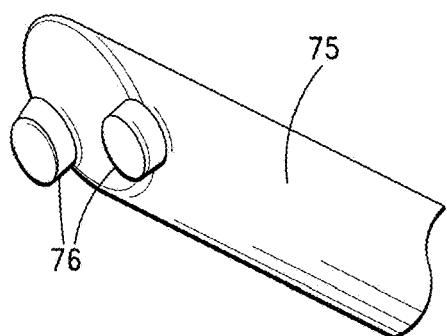
Figure 5C:
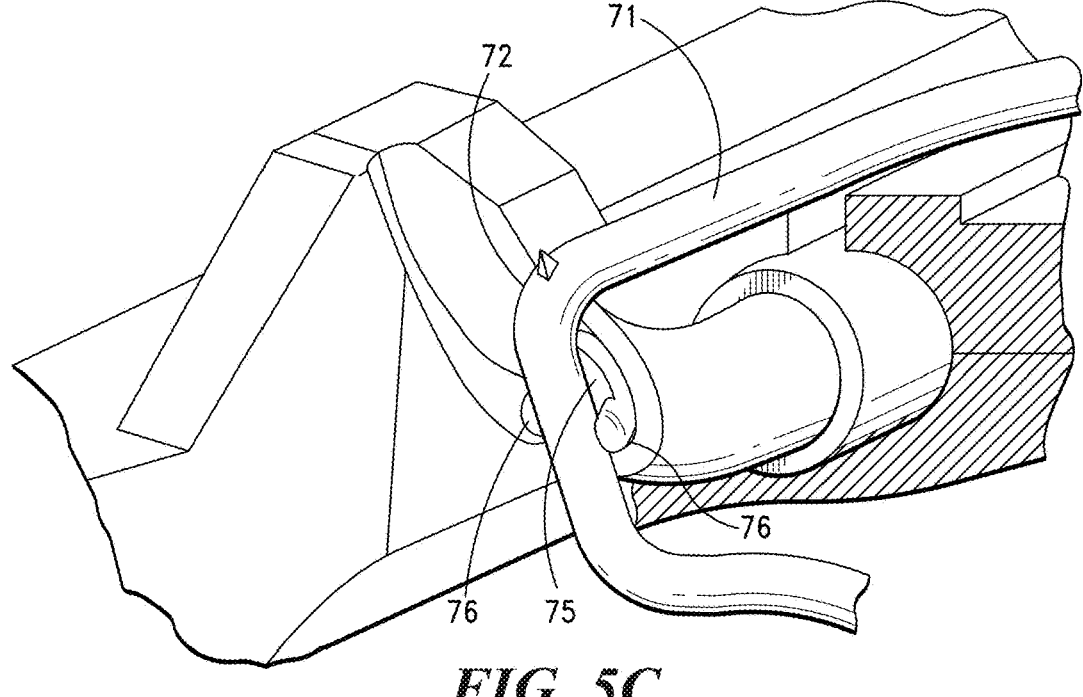
Figure 6C:
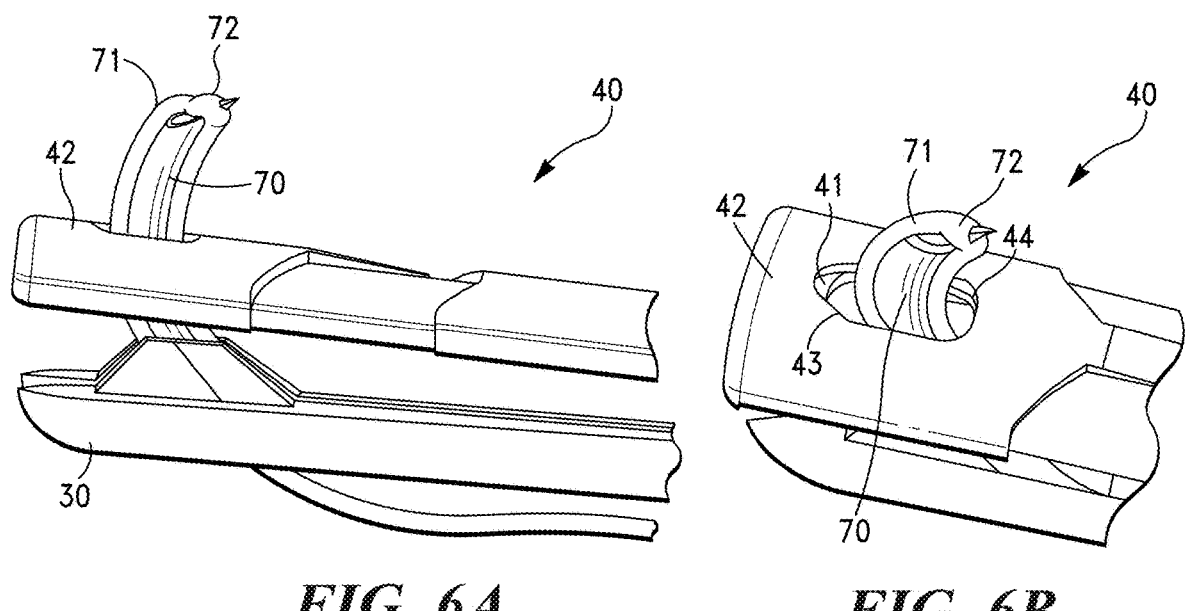
Figure 6C:
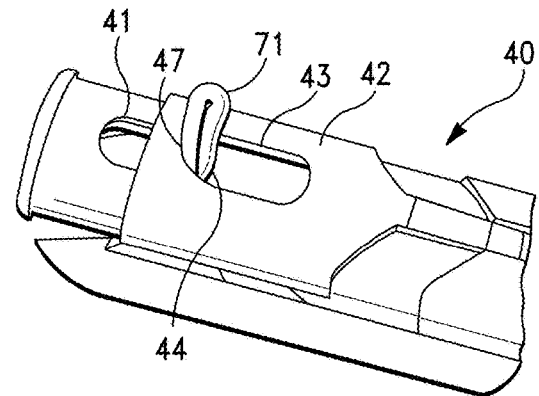
Figure 6D:
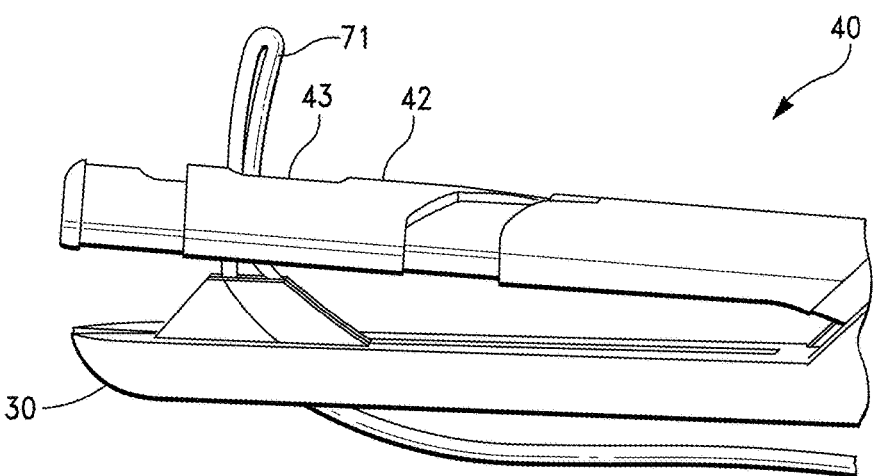
Figure 7A:
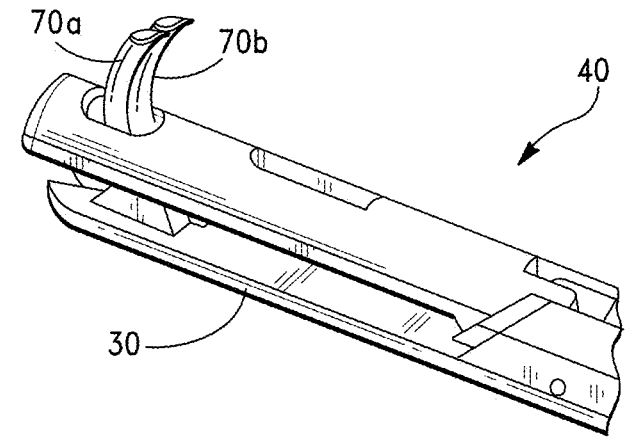
Figure 7B:
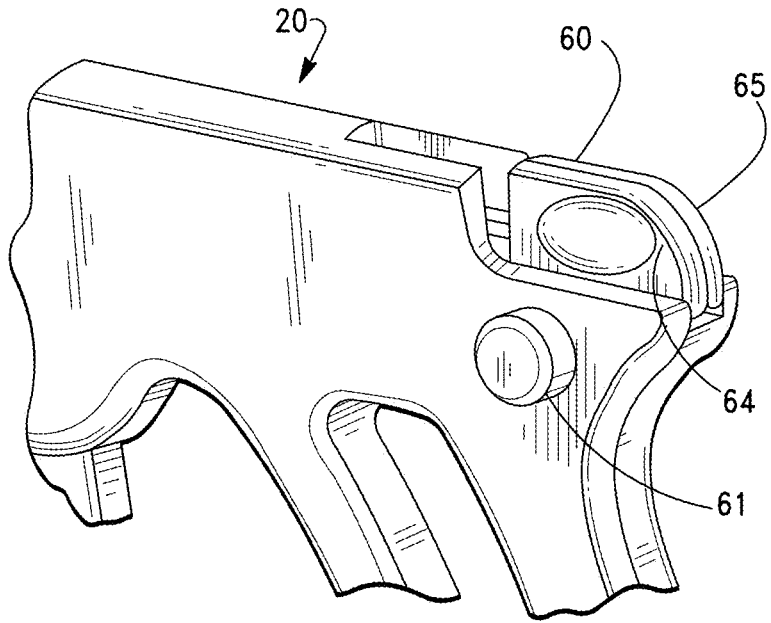
Figure 8A:
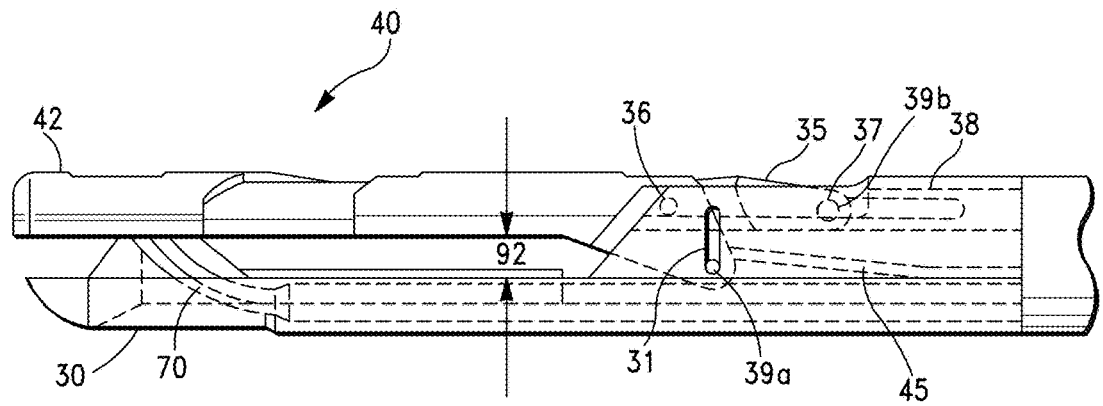
Figure 8B:
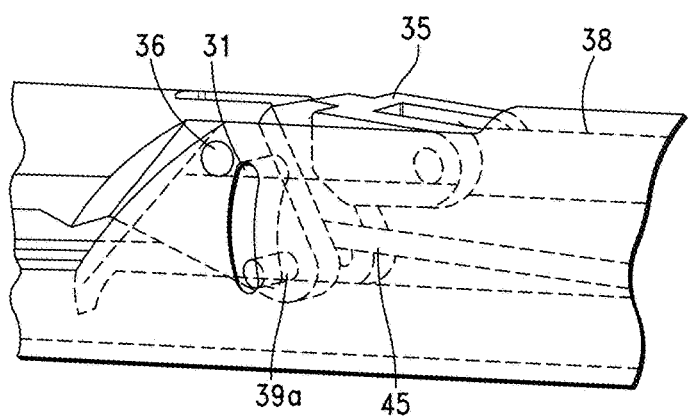
Figure 8C:
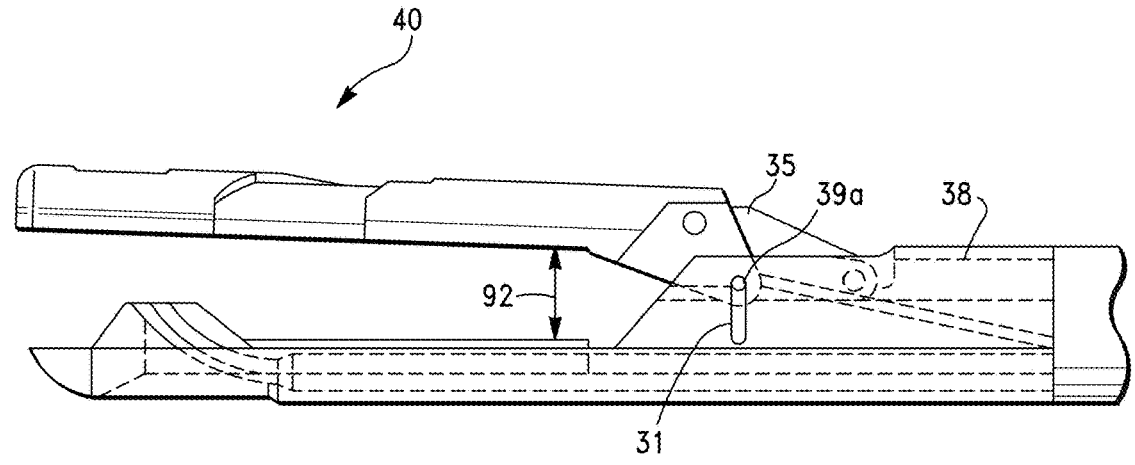
Figures 9A, 9B, 9C:
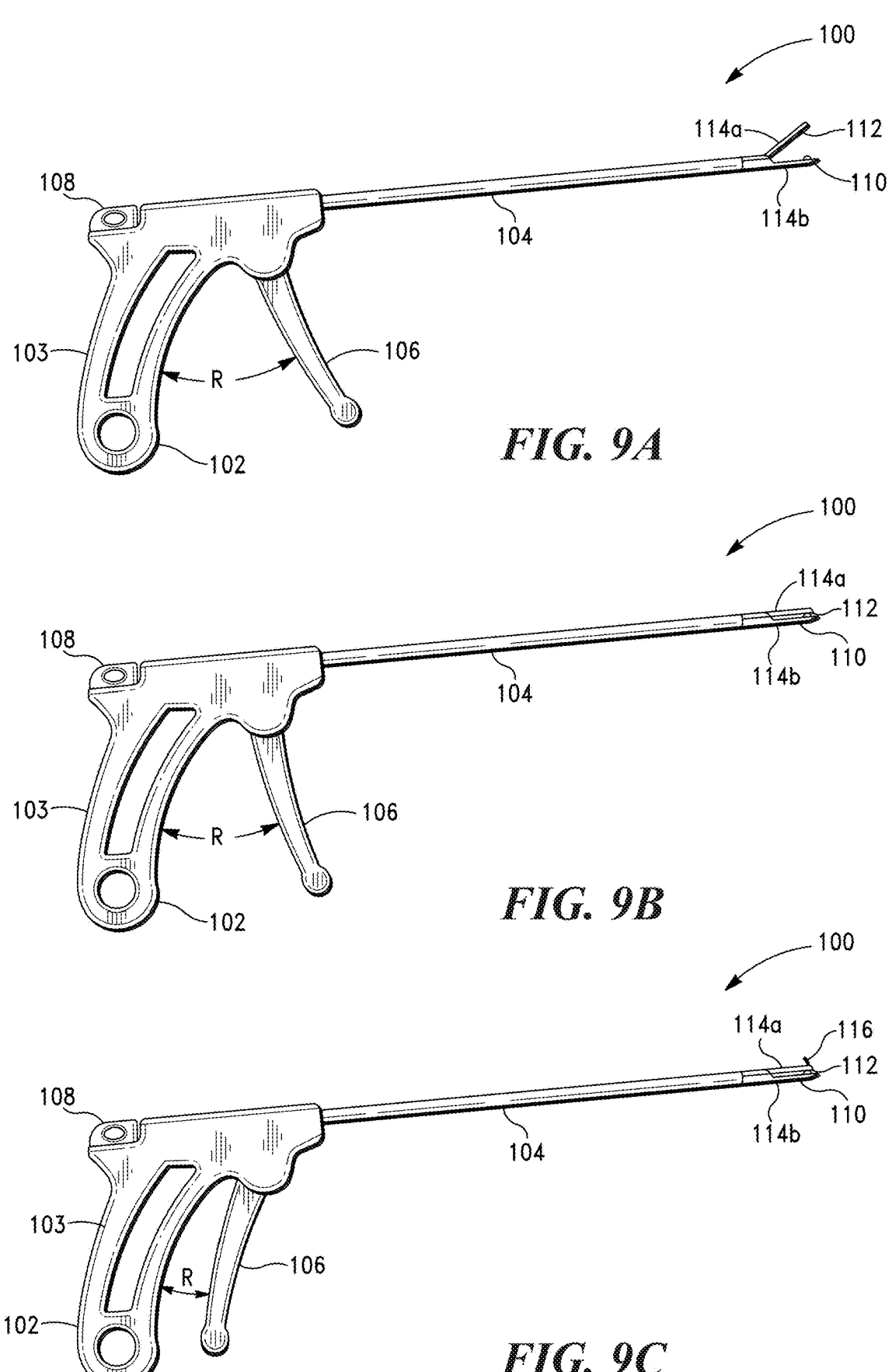
Figure 10A:
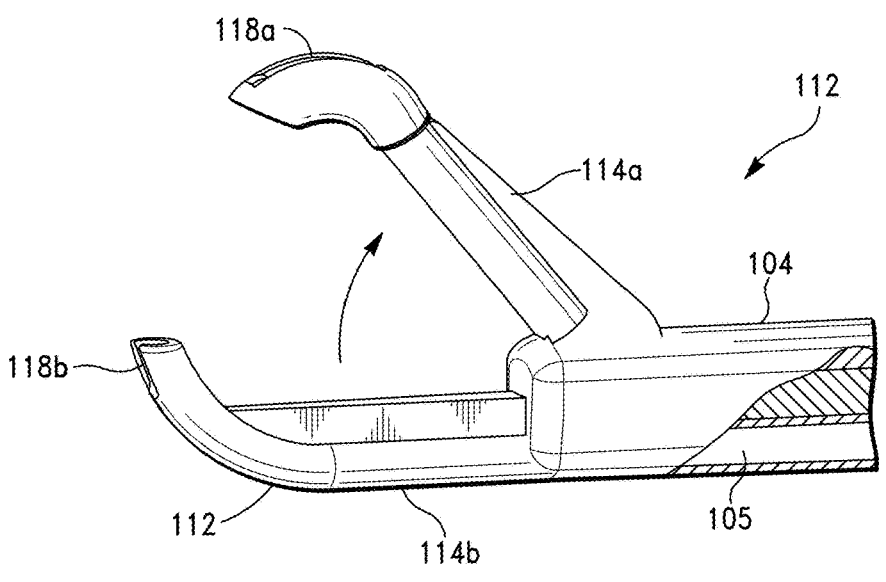
Figure 10B:
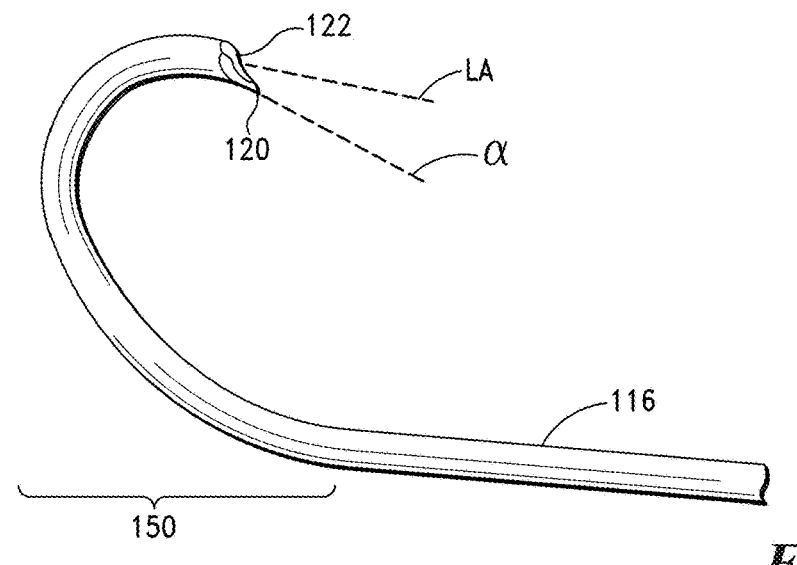
Figure 10C:
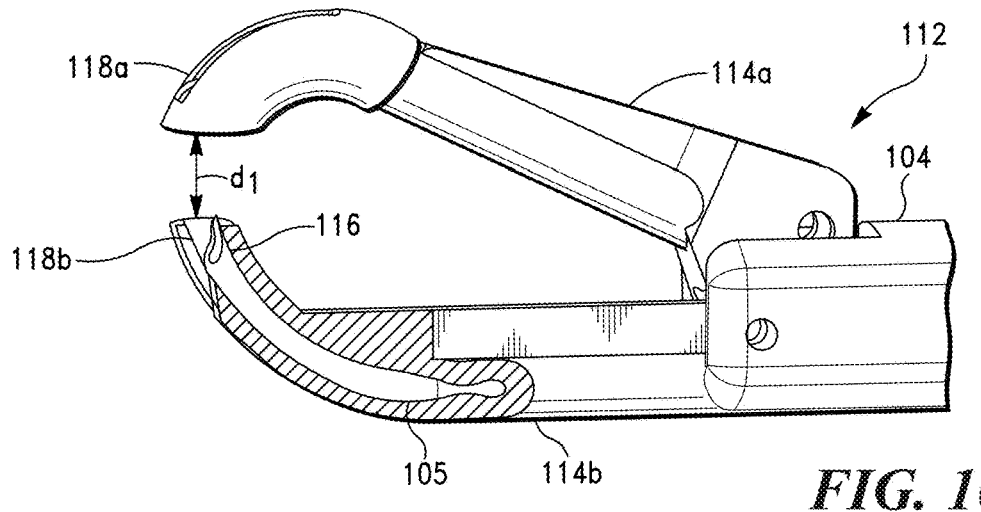
Figures 11A, 11B, 11C:
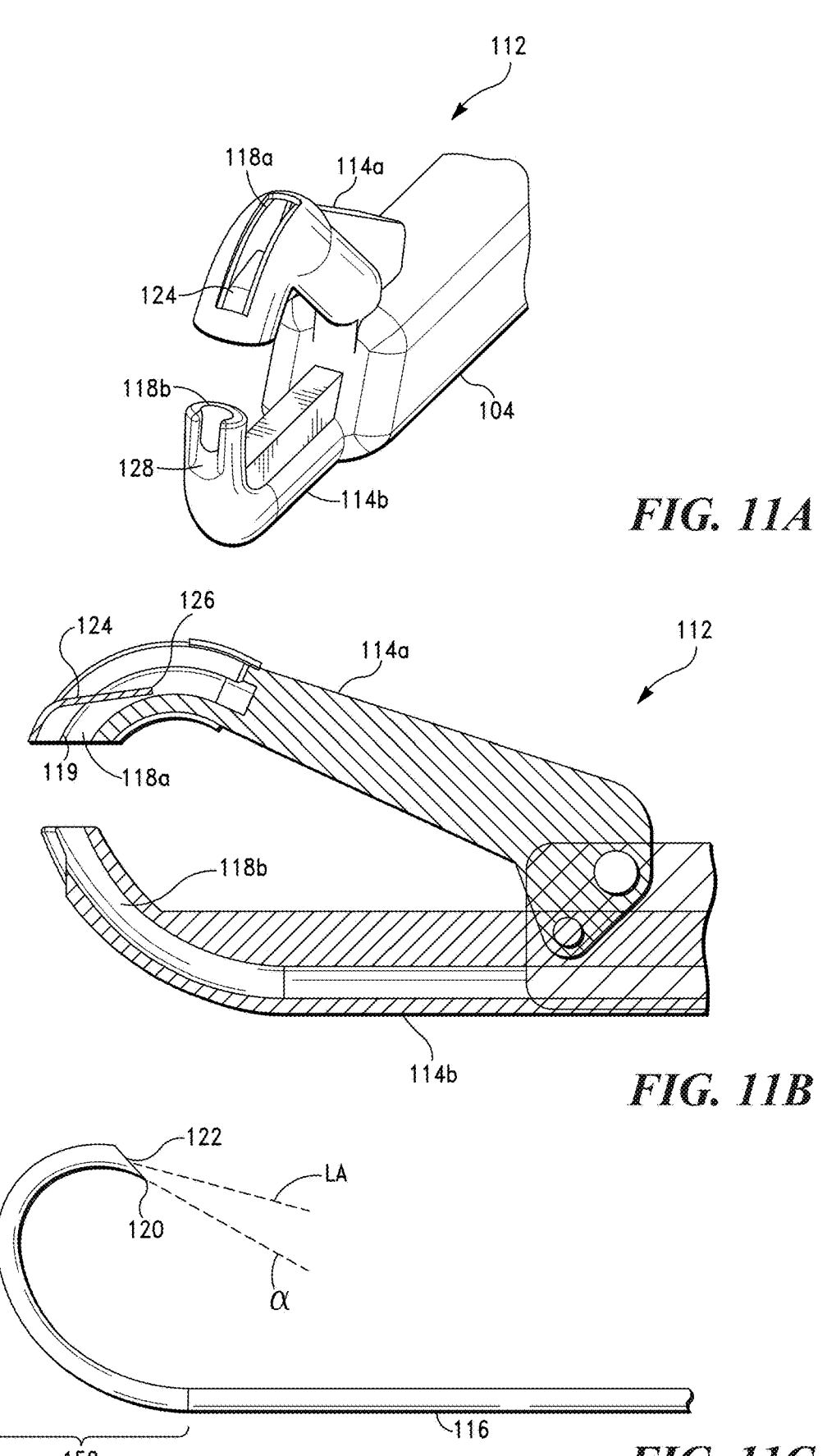
Figure 12A:
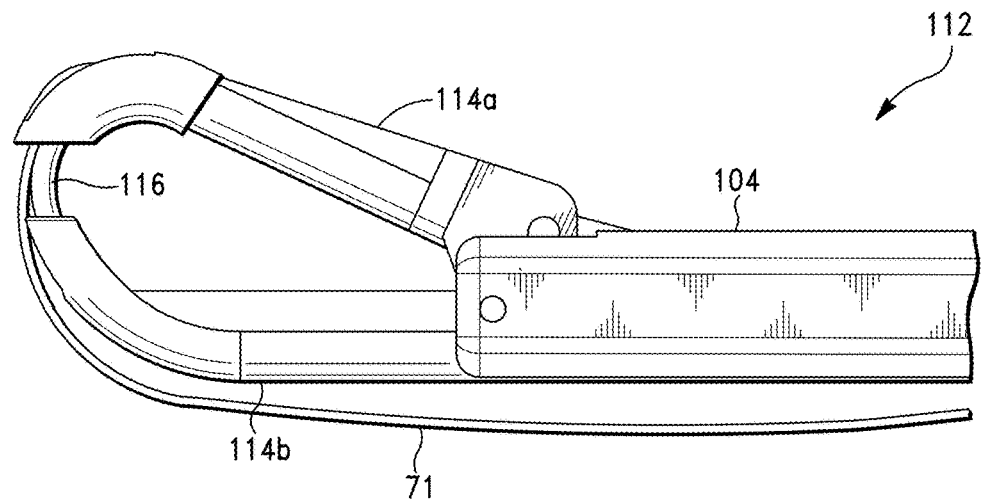
Figure 12B:
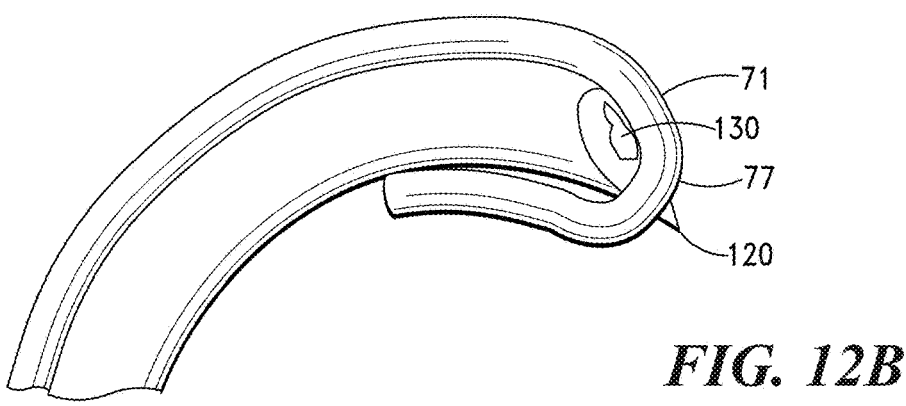
Figure 12C:
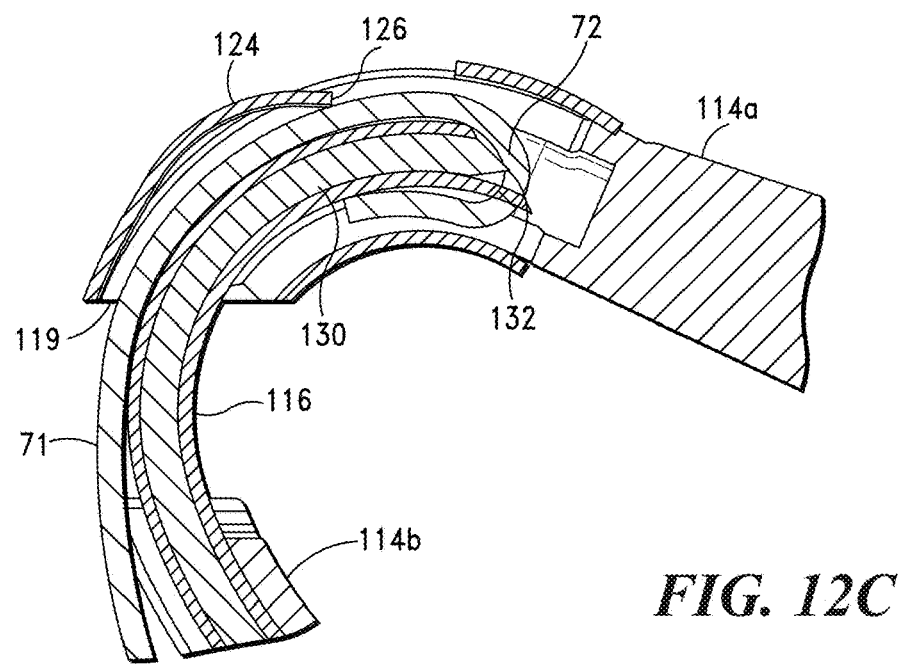
Figure 13A:
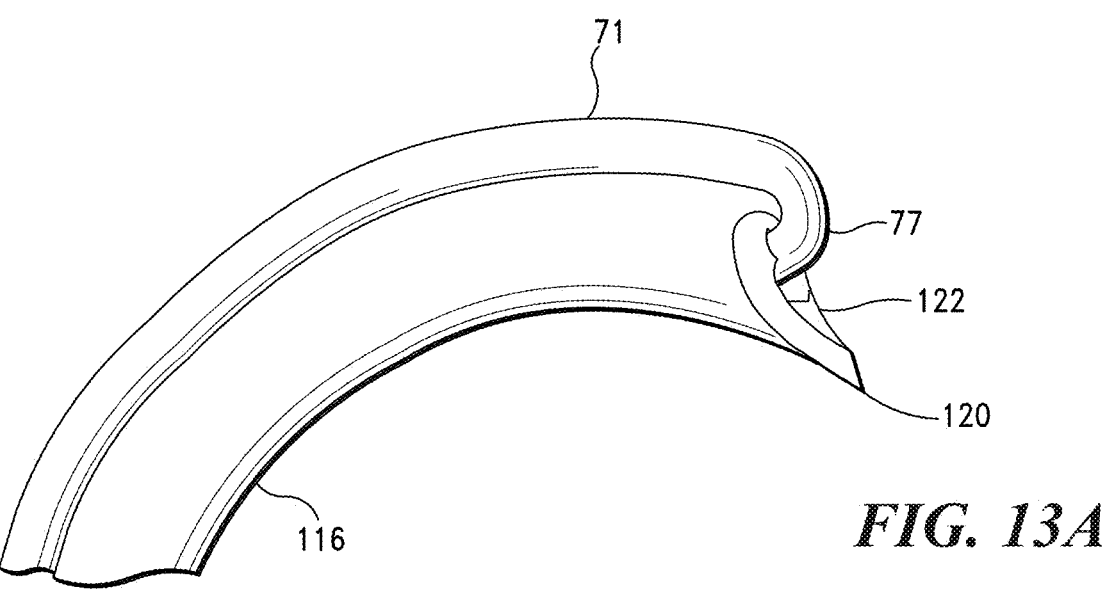
Figure 13B:
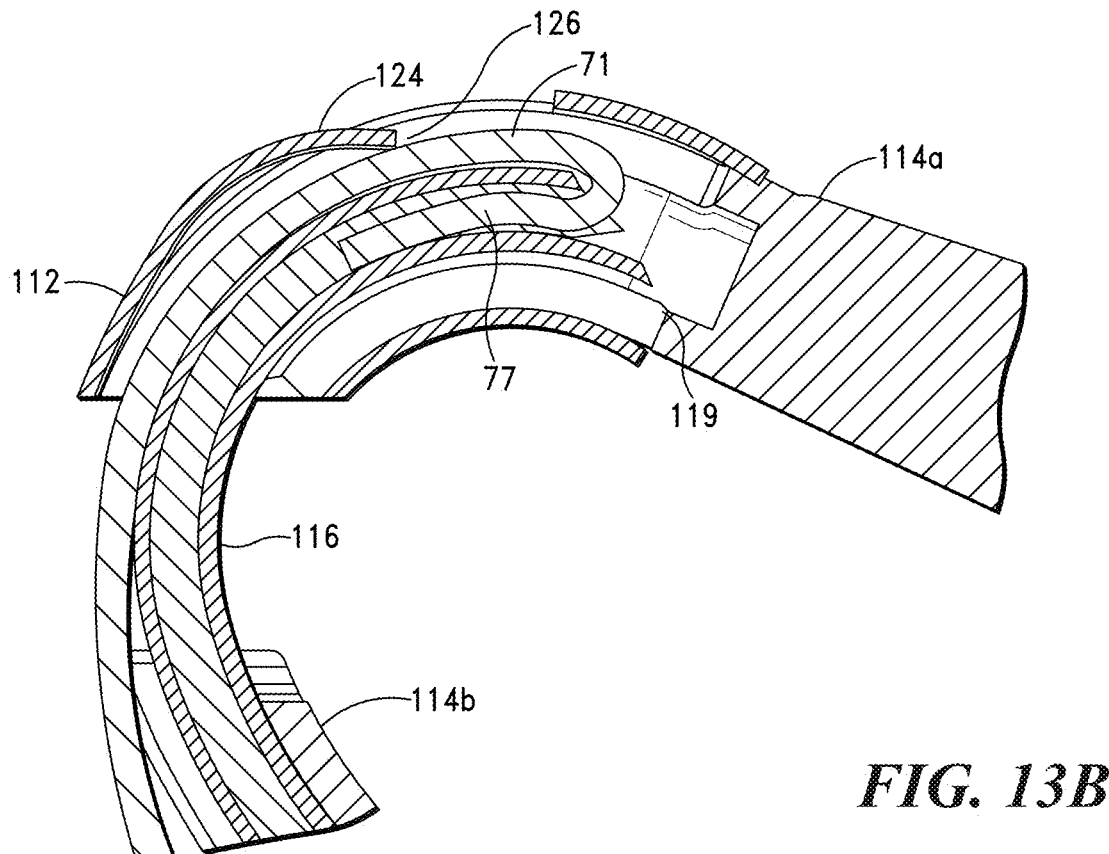
Figure 14:
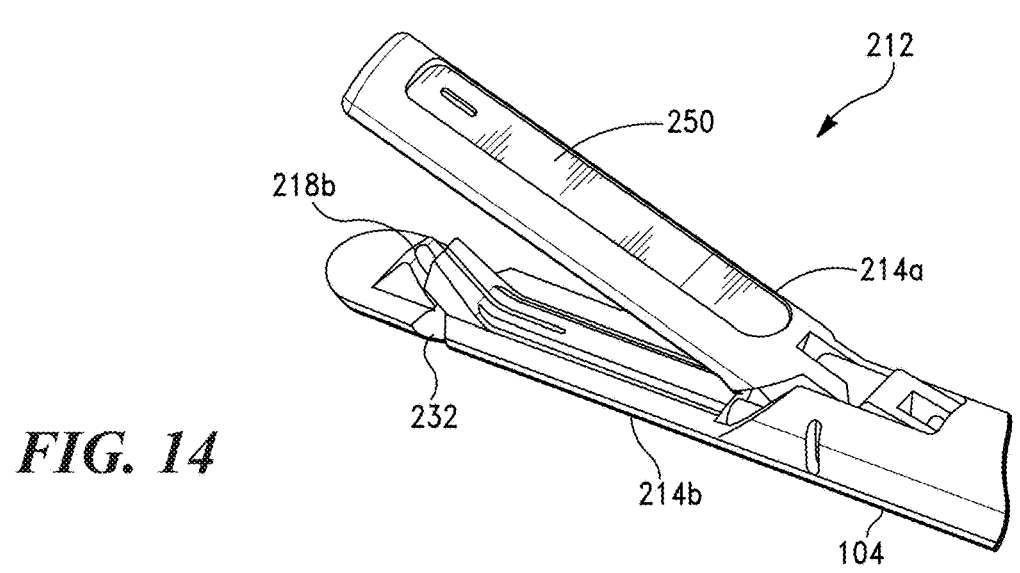
Figure 15:
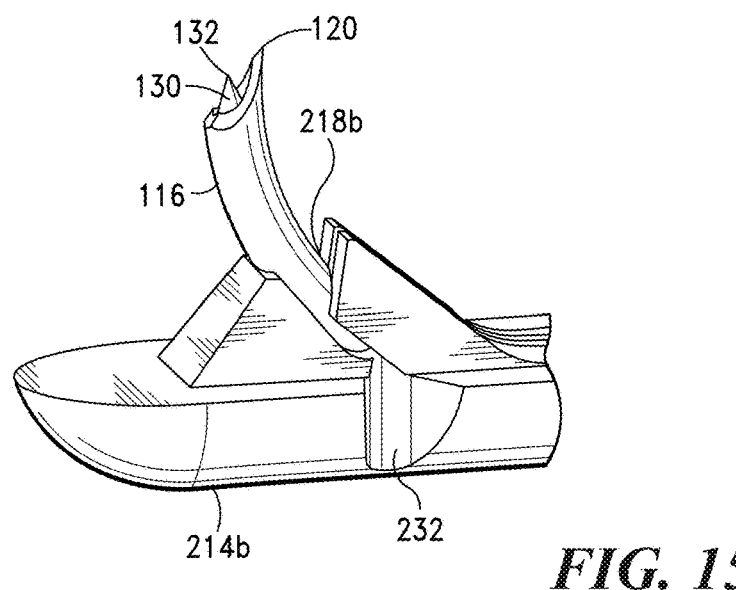
Figure 16:
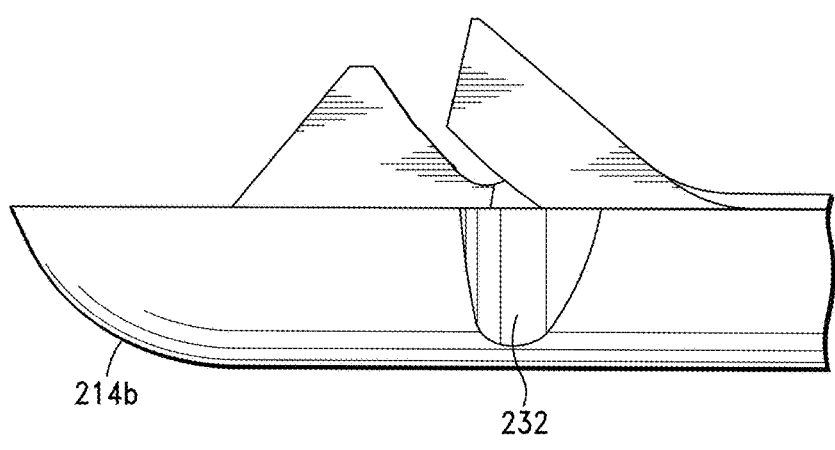
Figures 17, 18, 19:
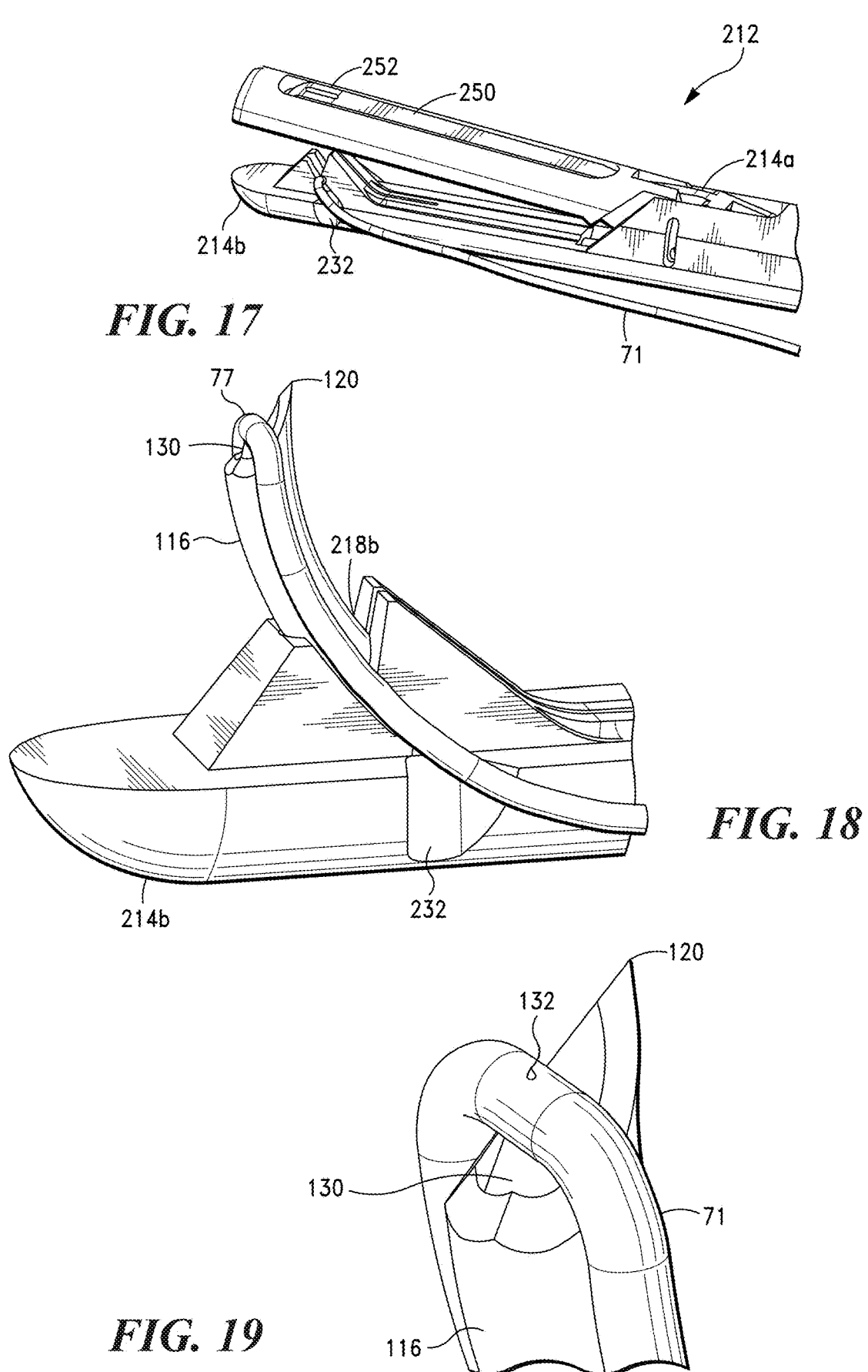
Figure 20:
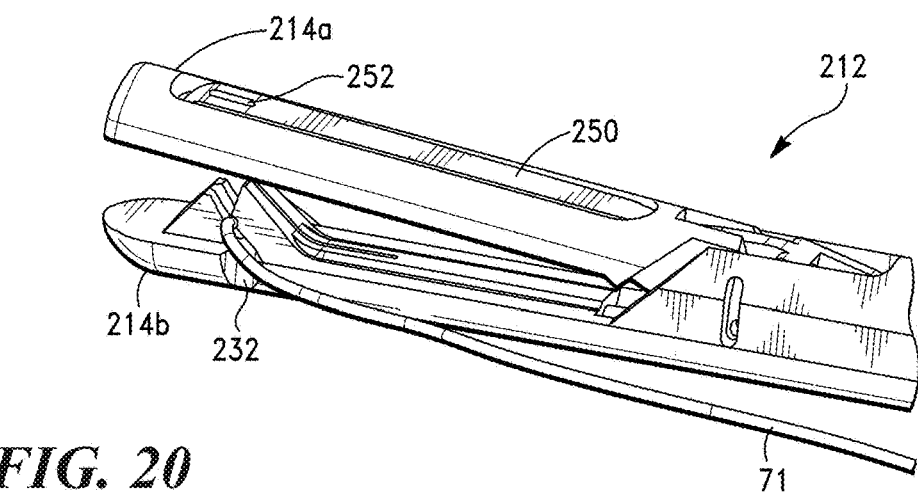
Figure 21:
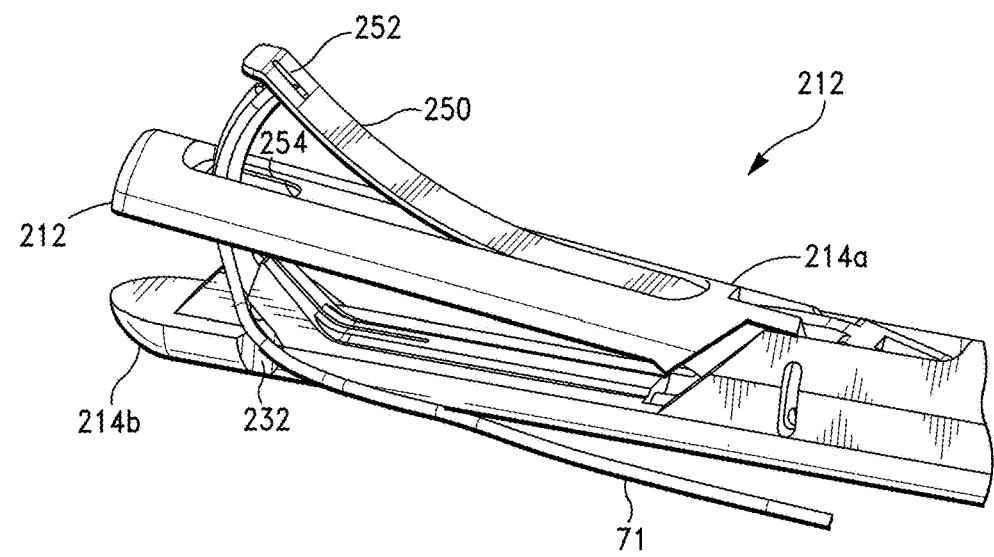
Figure 22:
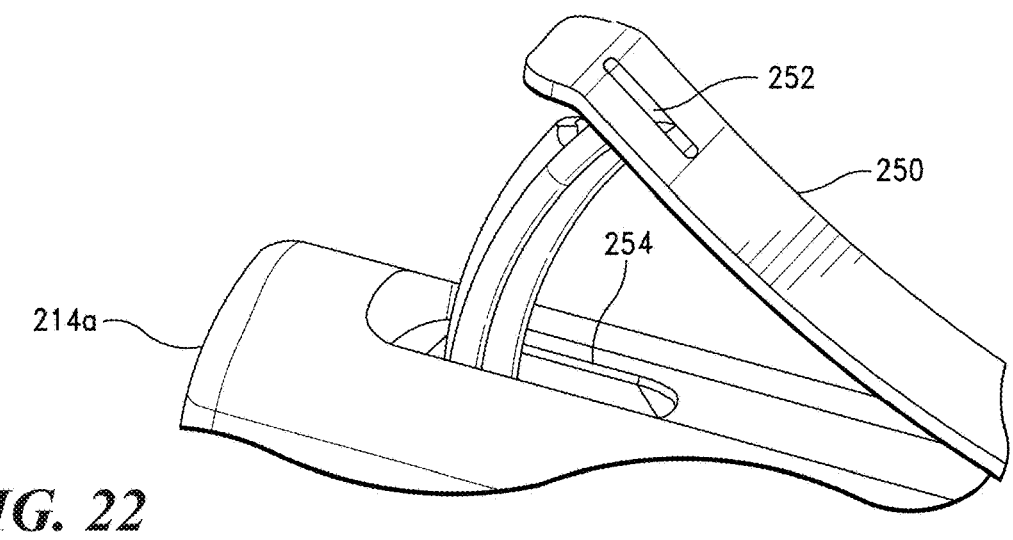
Figure 23:
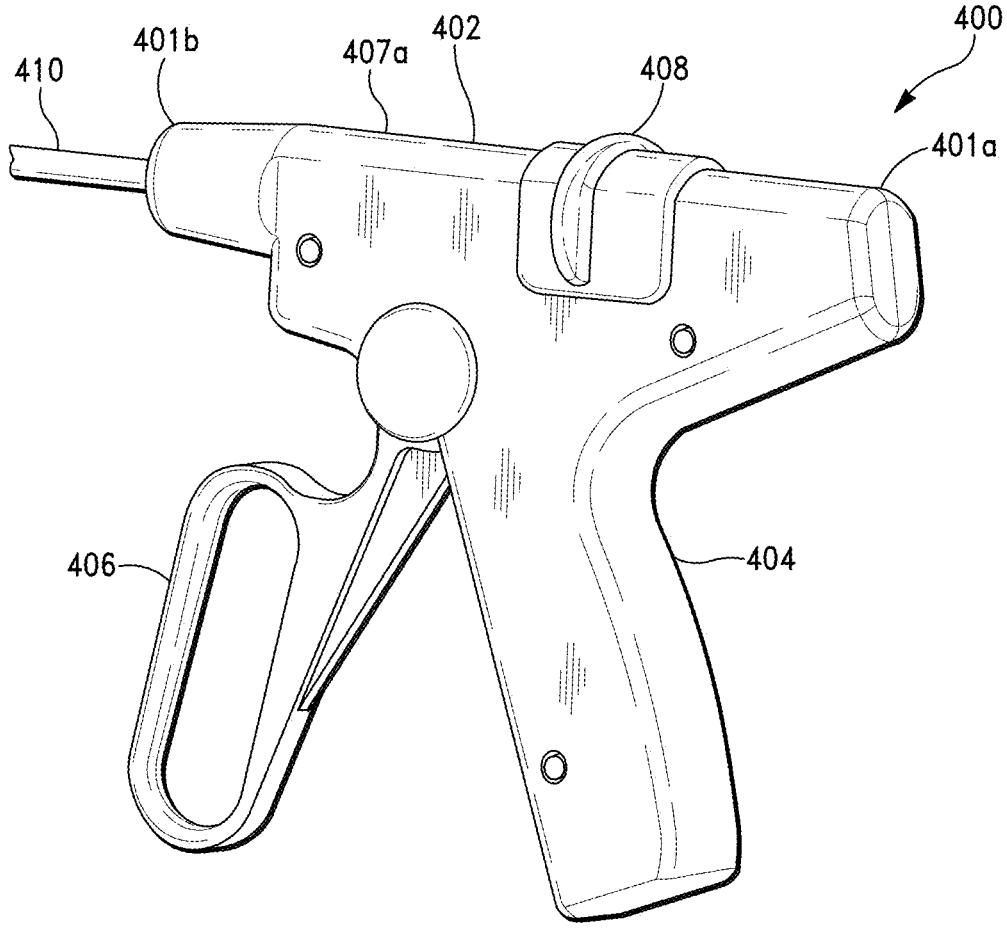
Figures 24A, 24B:
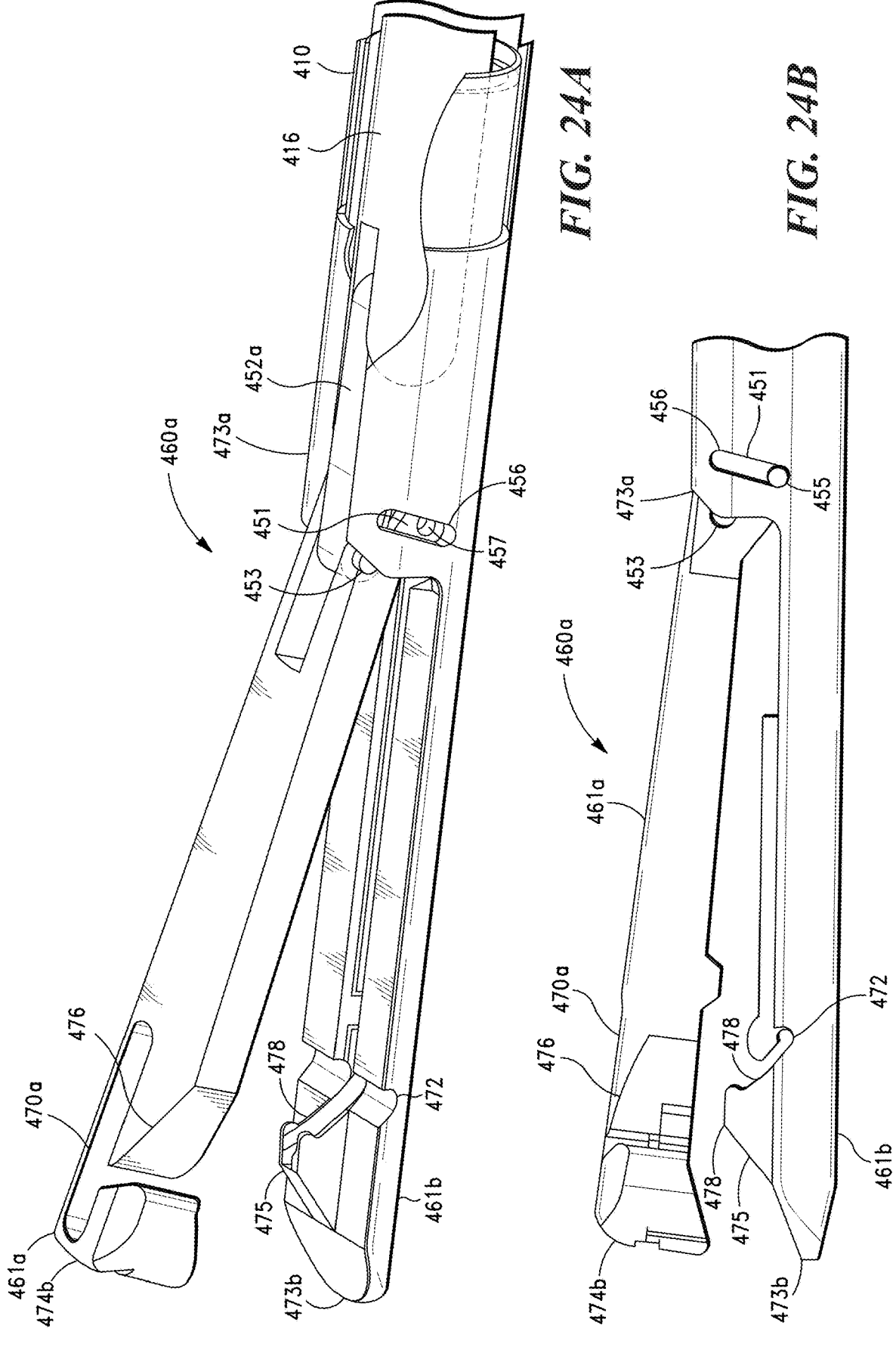
Figures 24C, 24D:
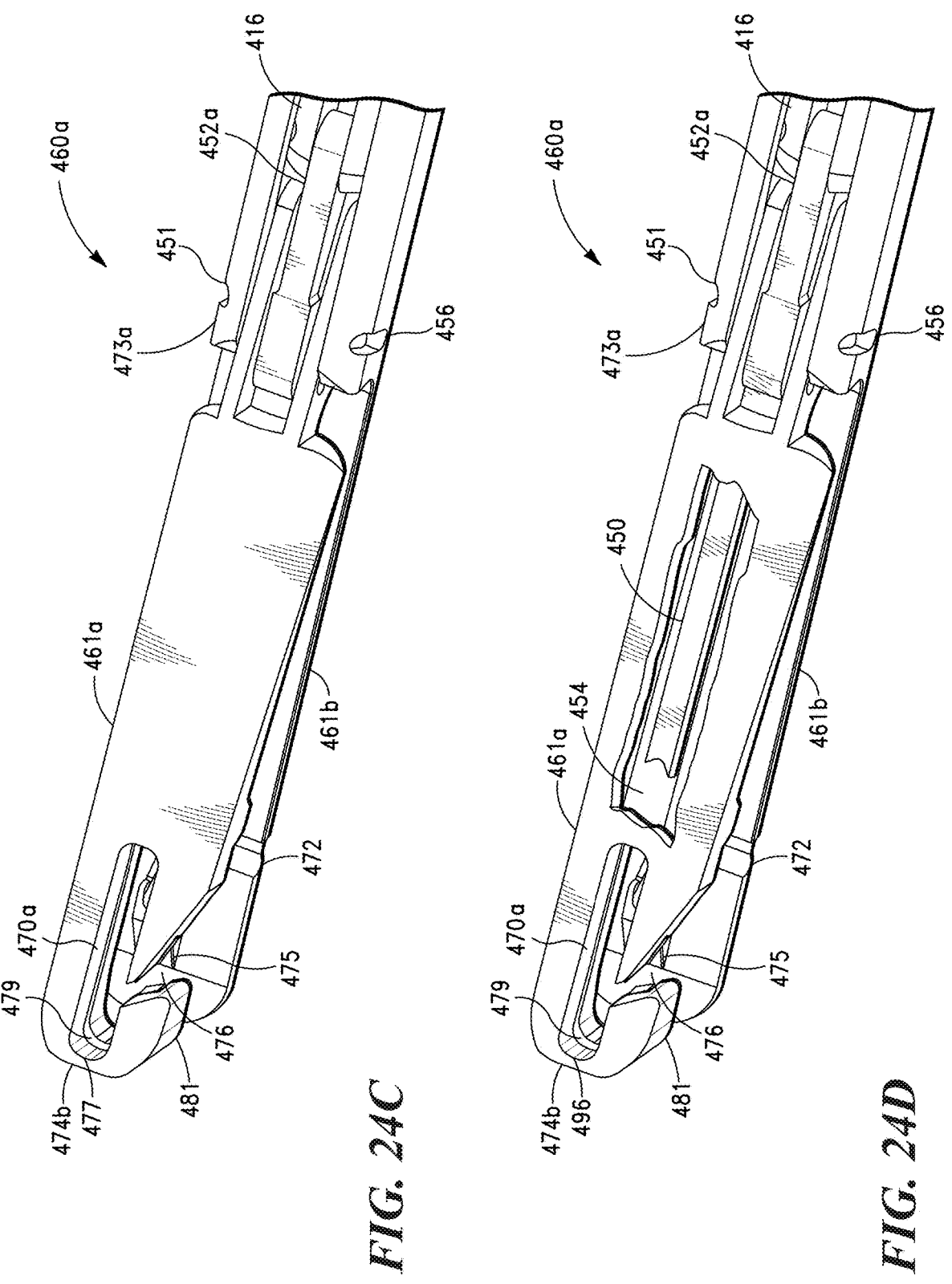
Figure 24E:
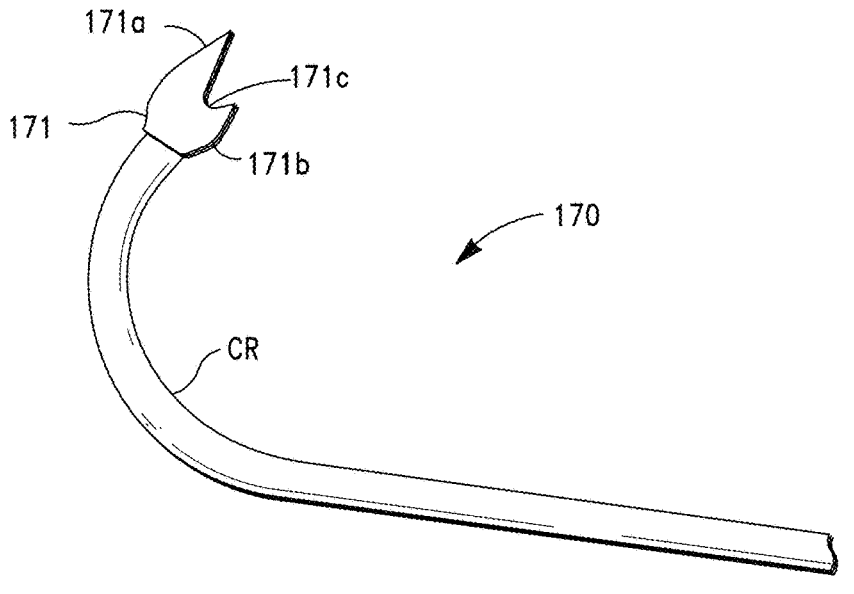
Figure 24F:
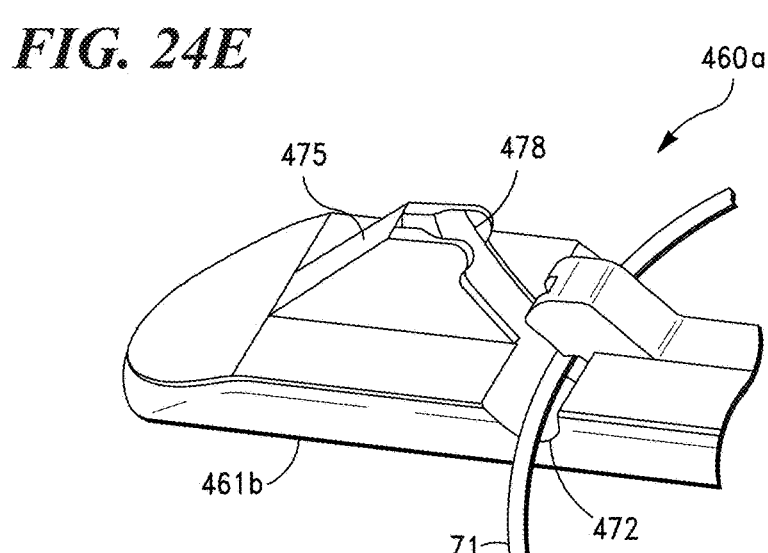
Figure 24G:
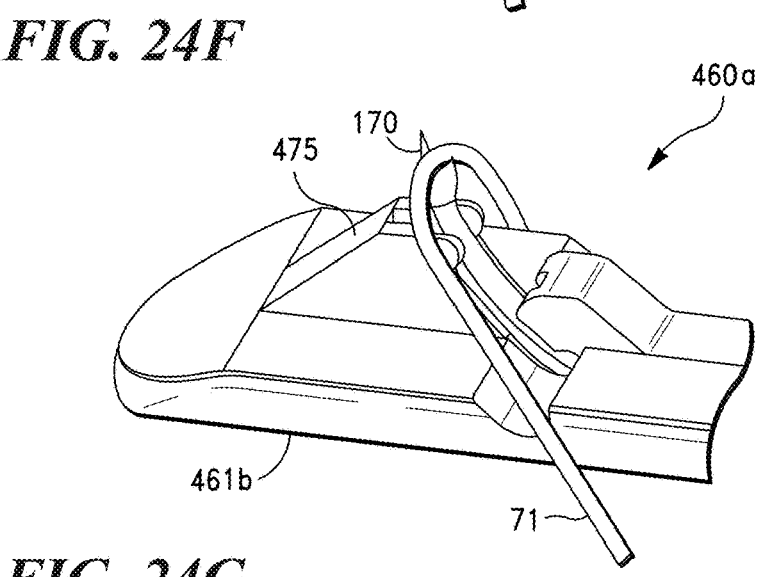
Figure 25:
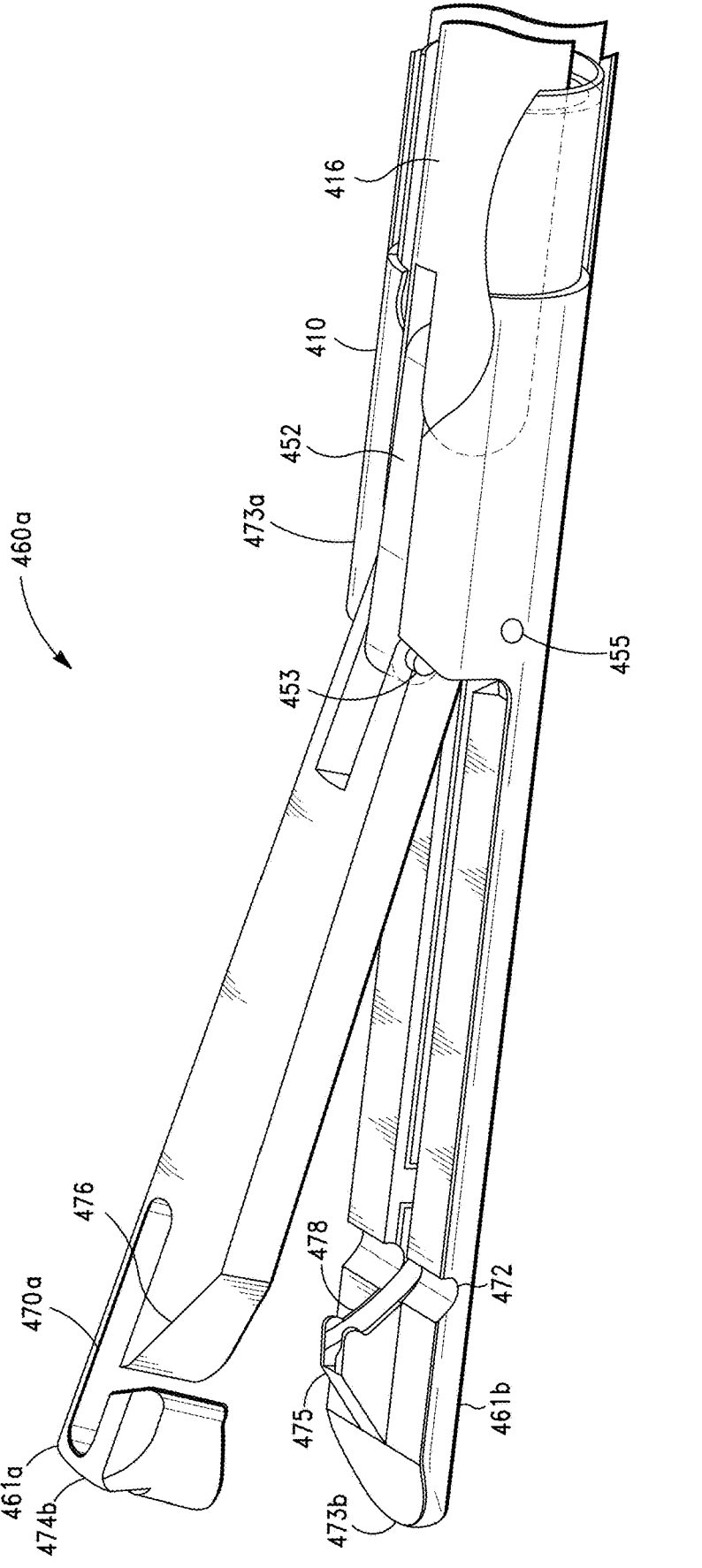
Figure 26A:
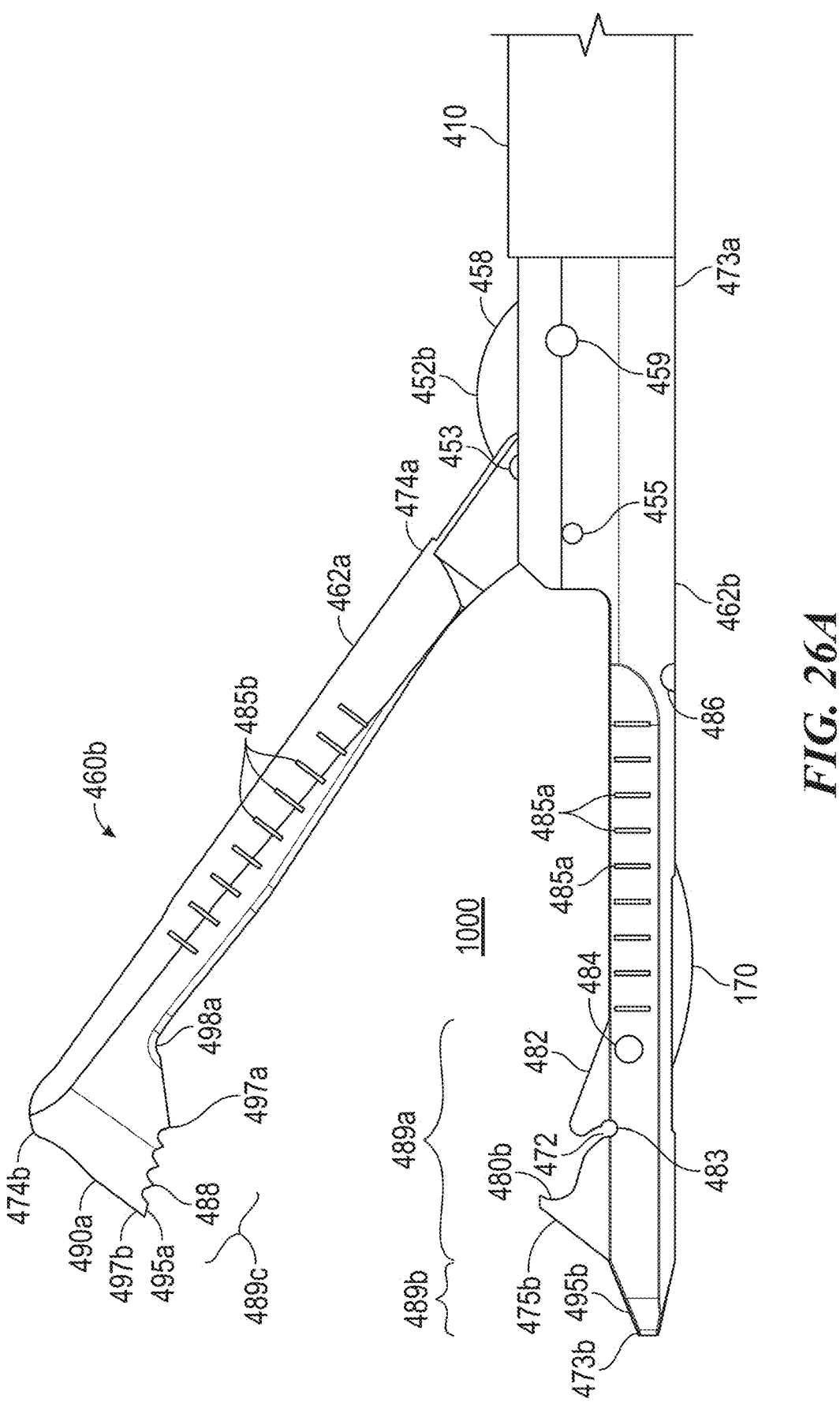
Figure 26B:
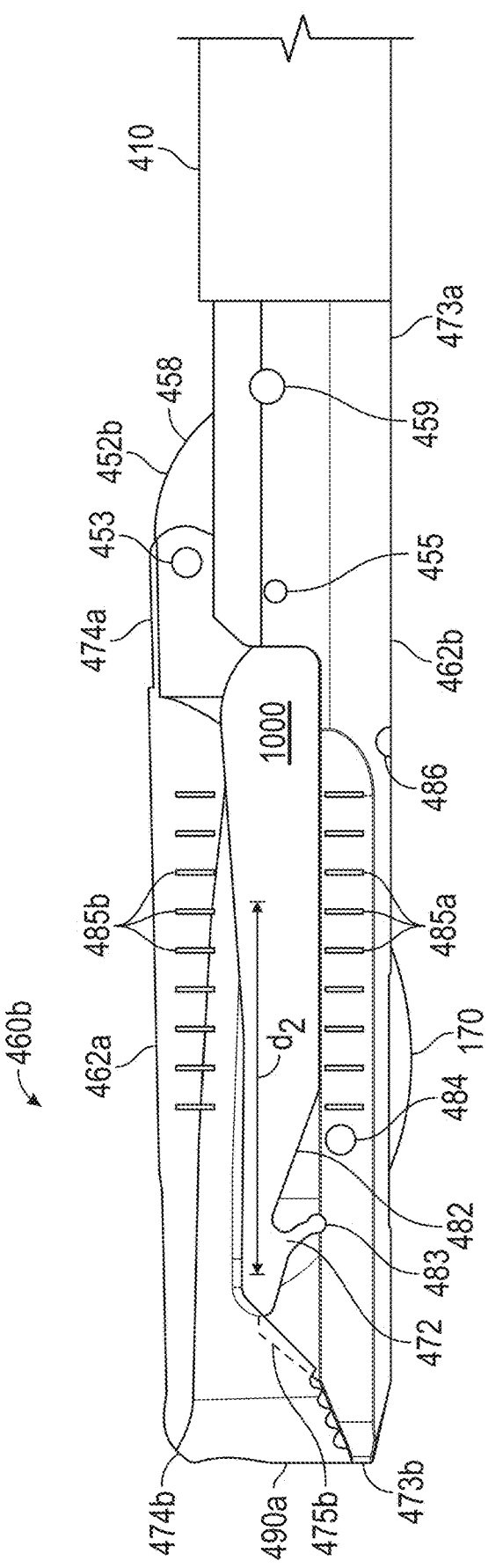
Figure 26F:
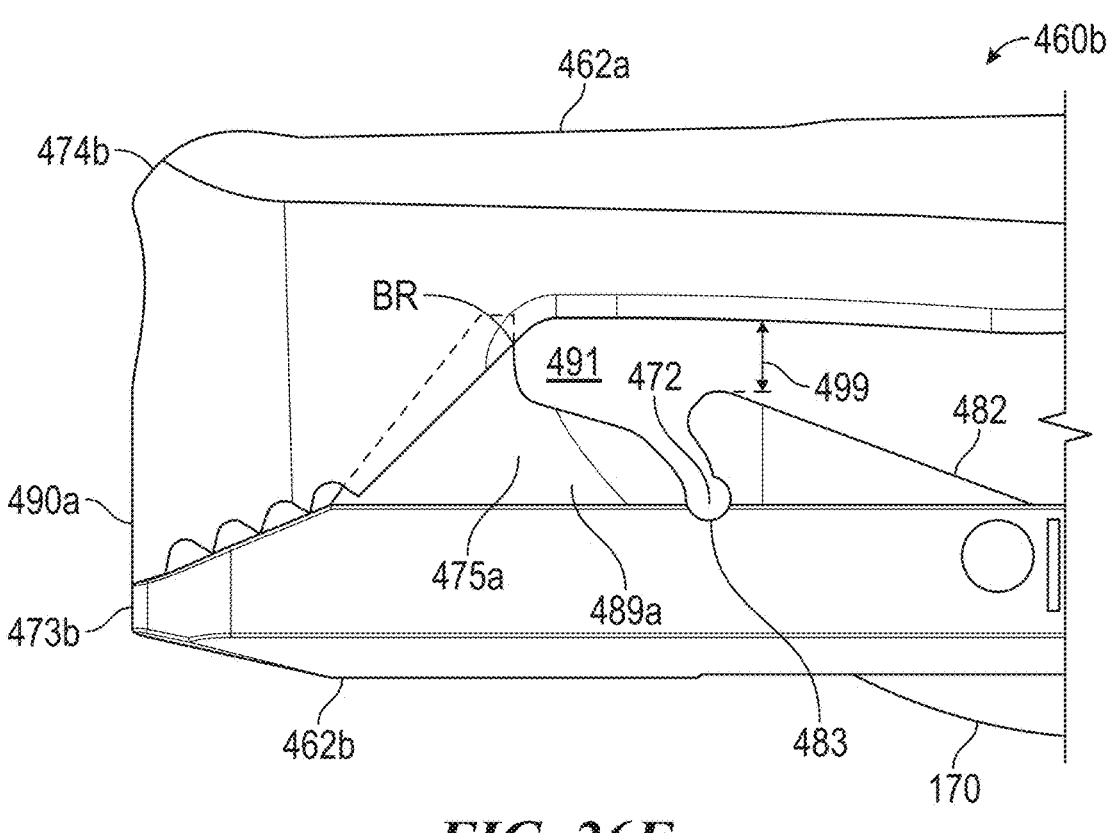
Figure 26G:
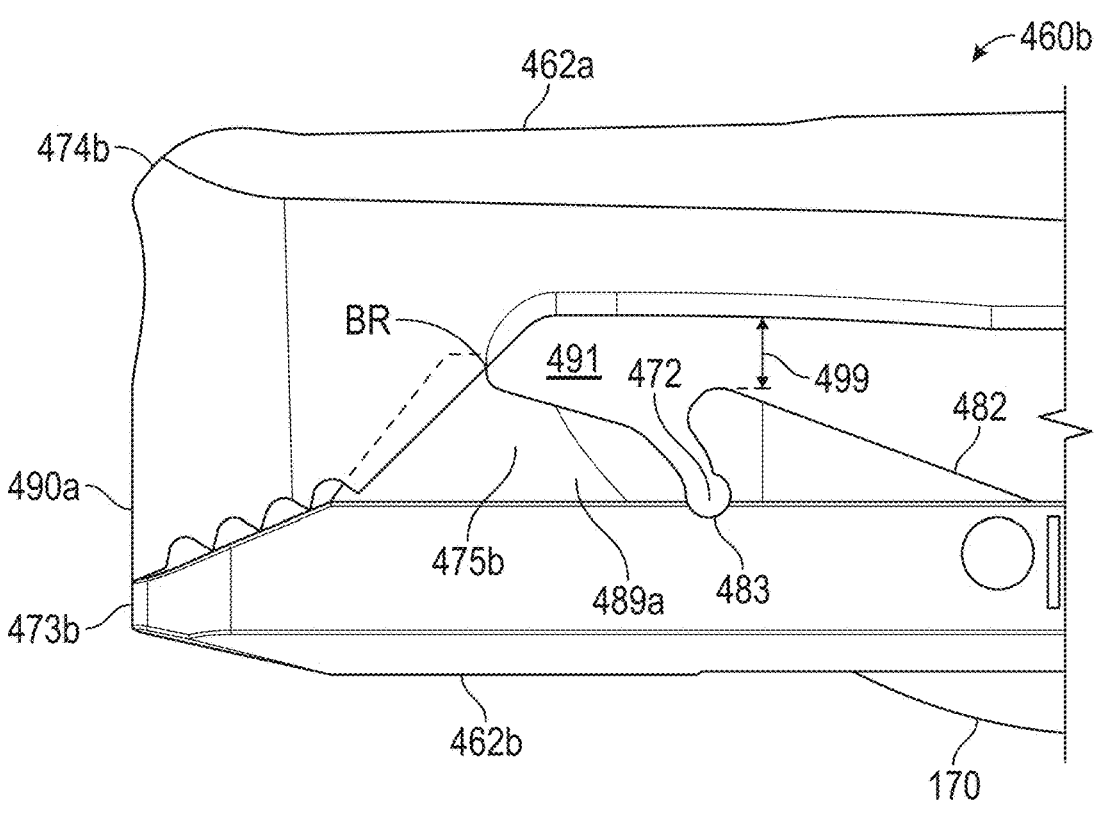
Figures 26H, 26I:
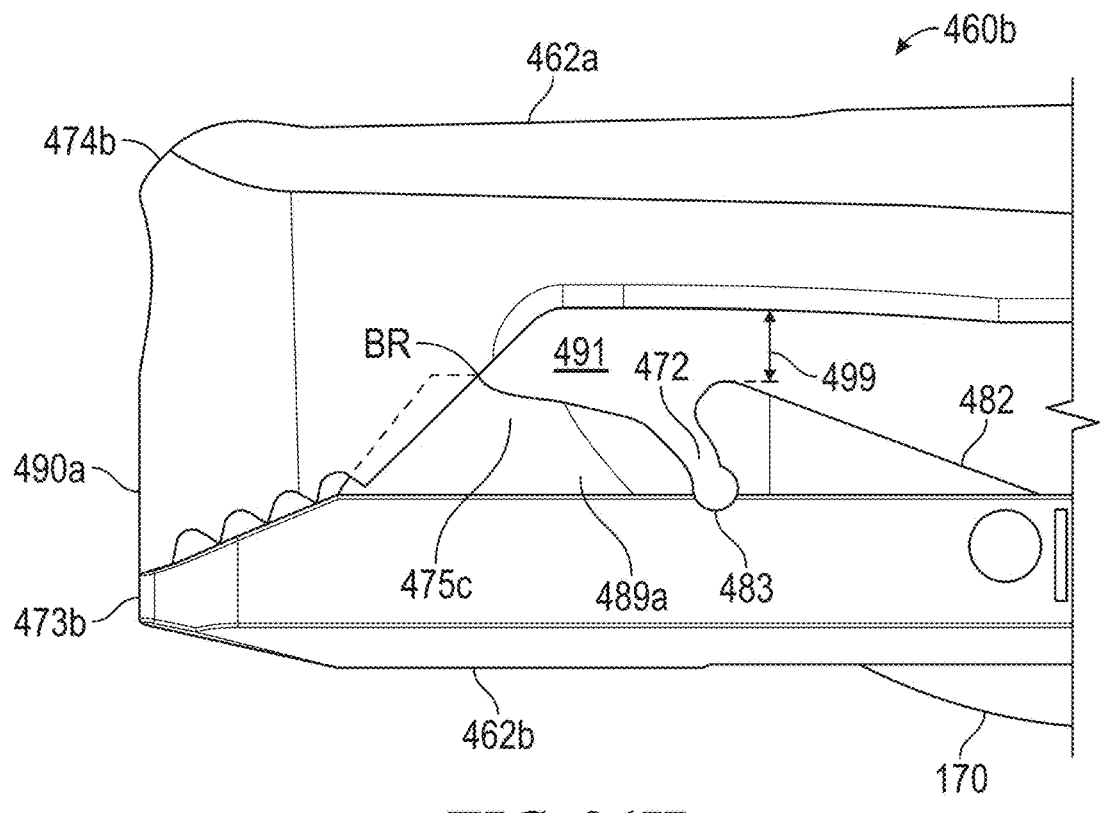
Figure 26J:
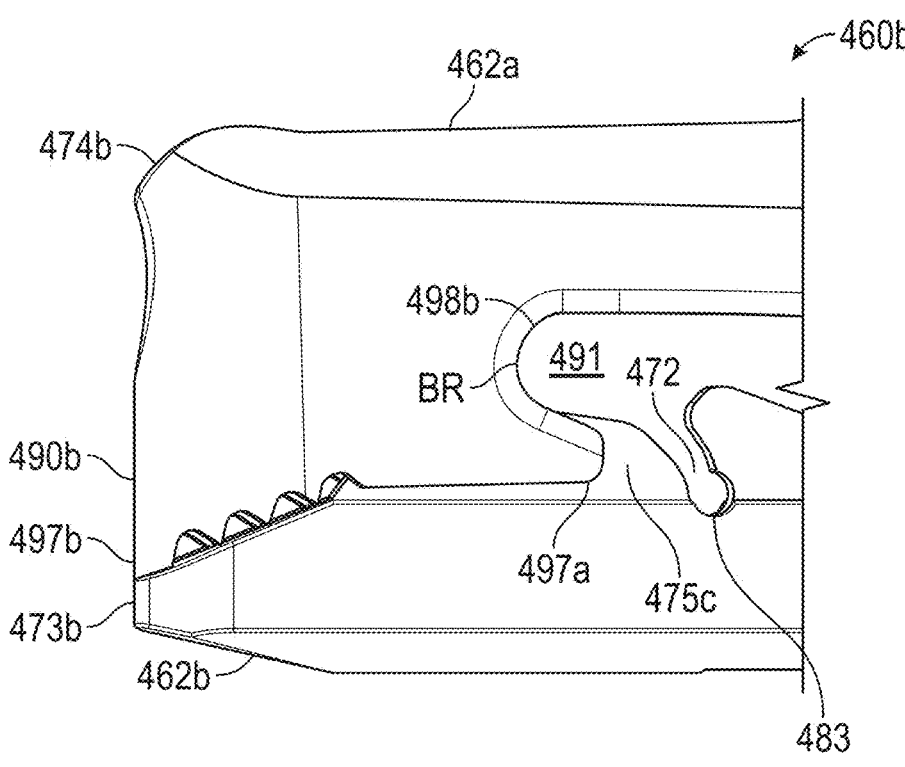
Figure 26K:
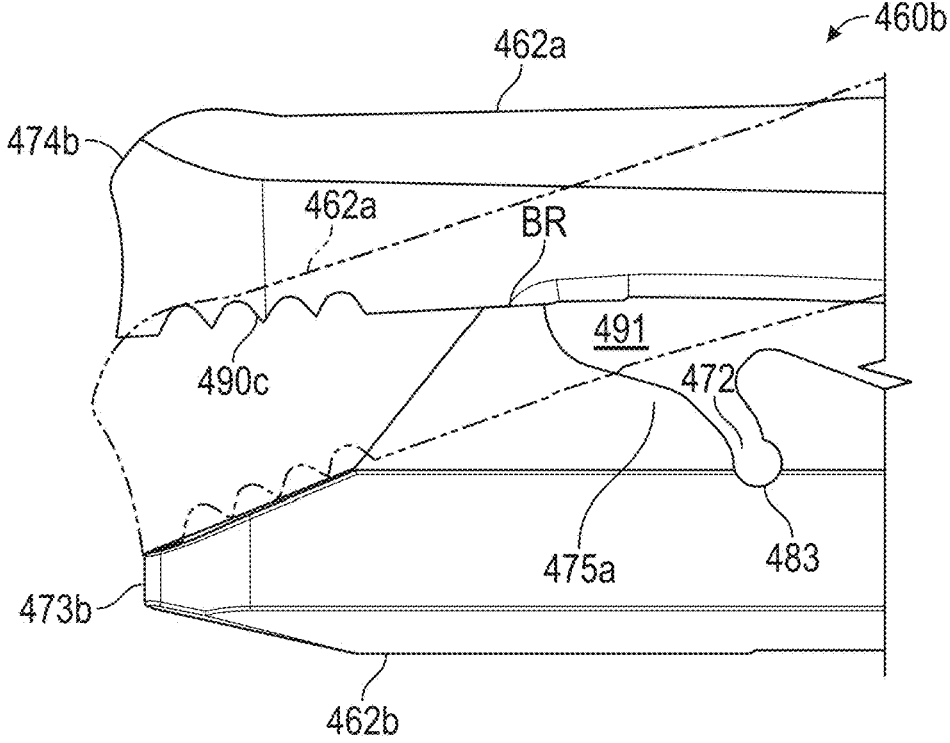
Figure 26L:
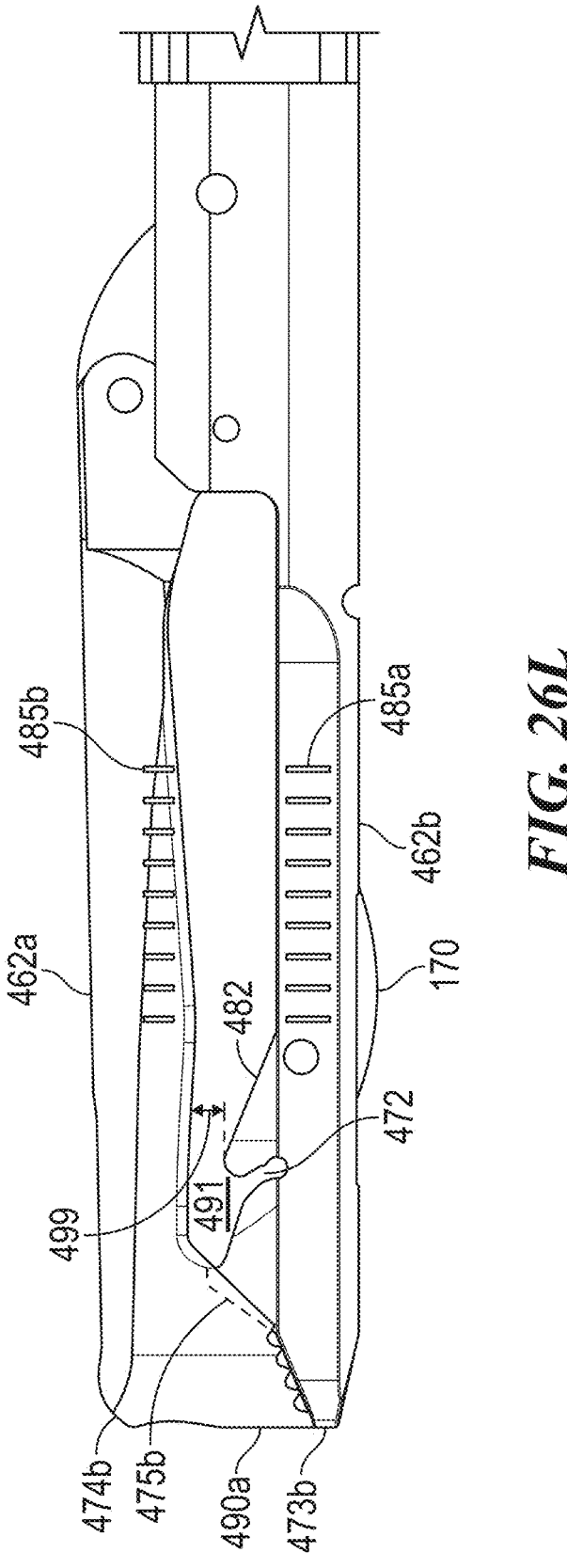
Figure 26M:
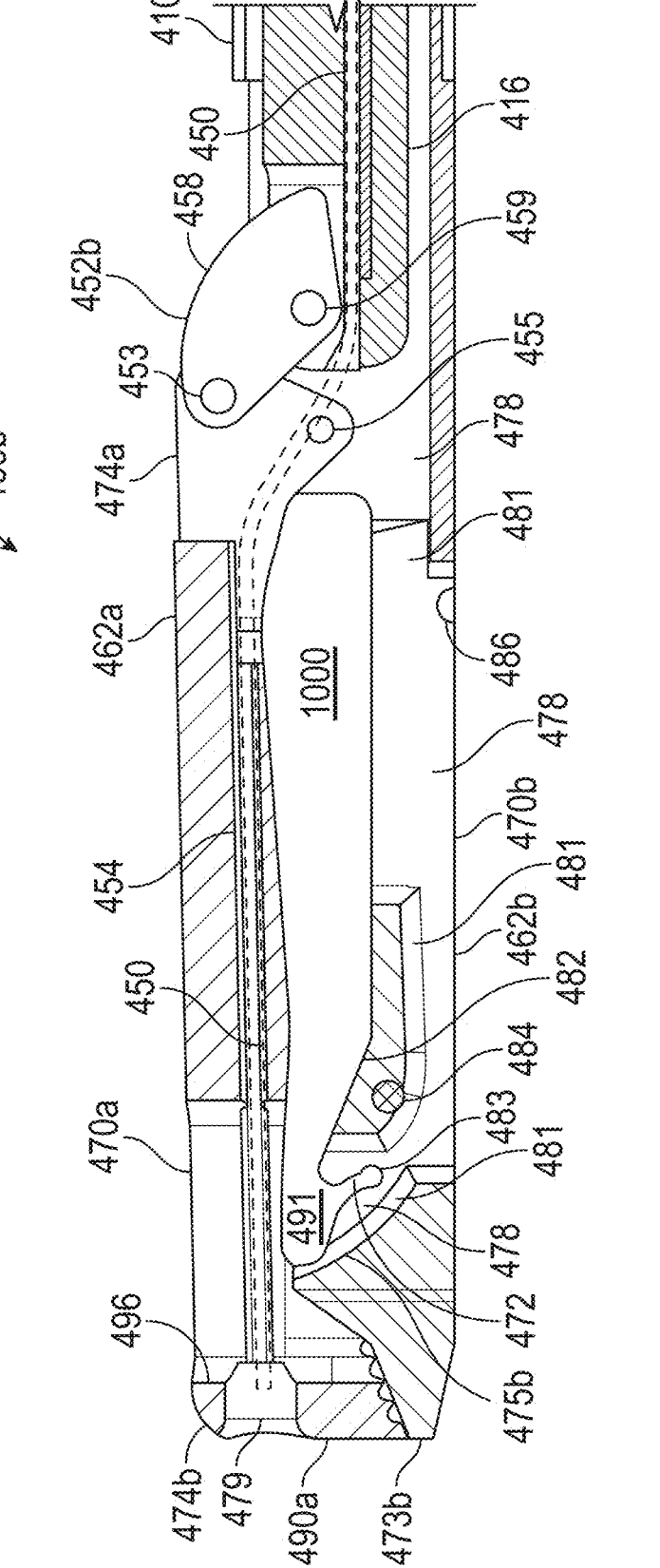
Figure 26N:
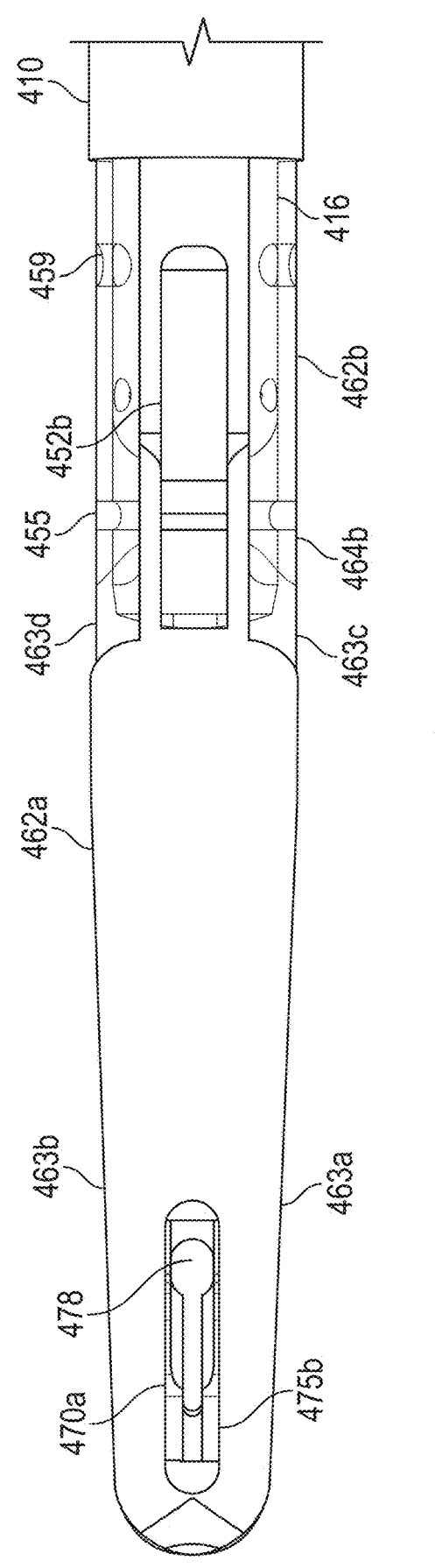
Figure 26O:
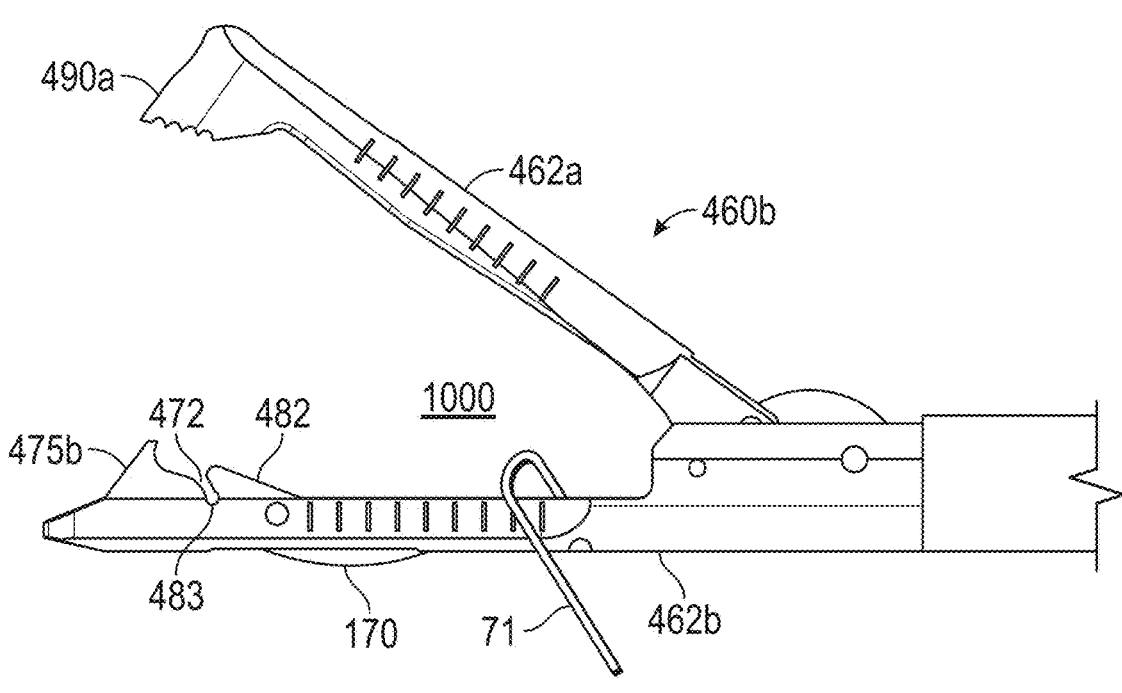
Figure 26P:
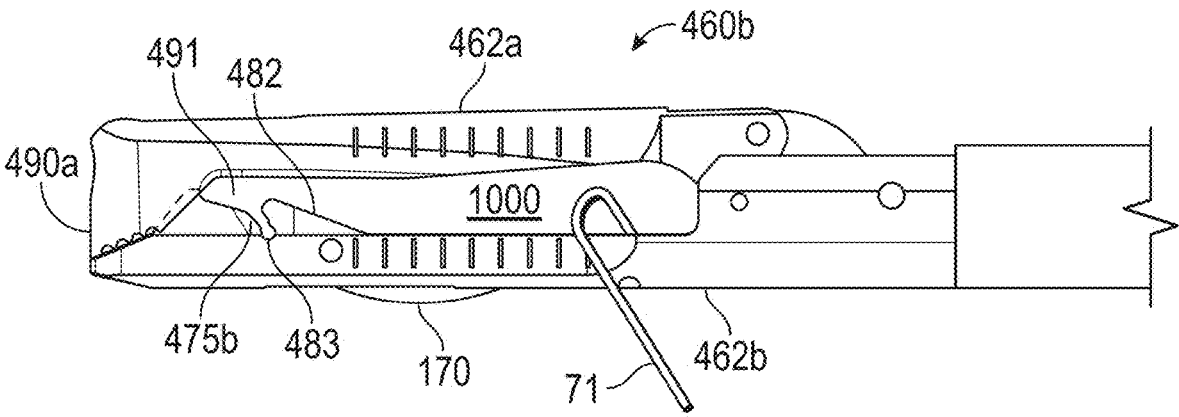
Figure 26Q:
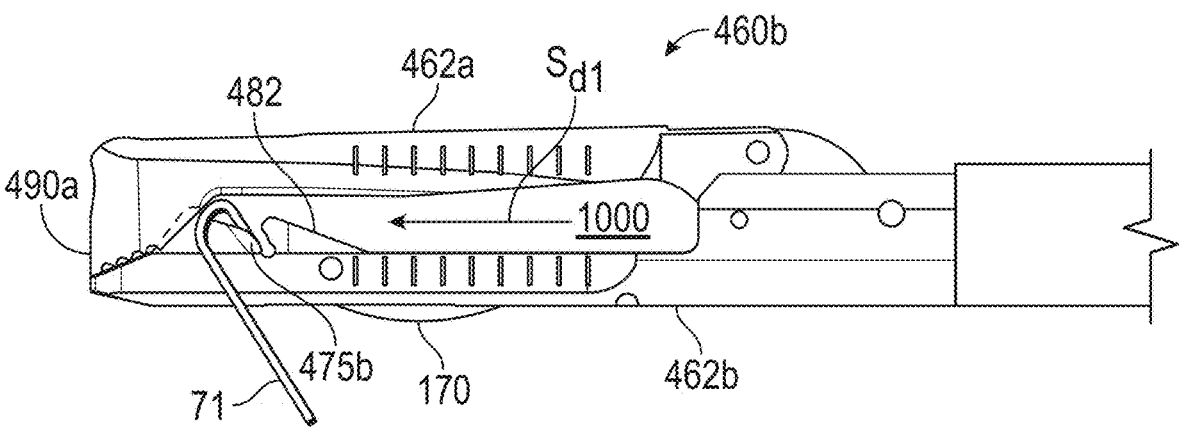
Figure 26R:
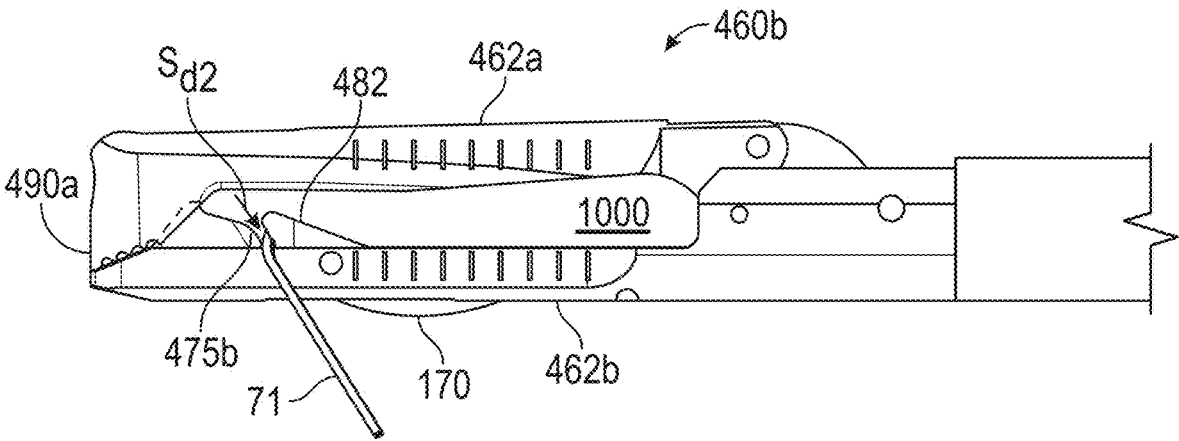
Figure 26S:
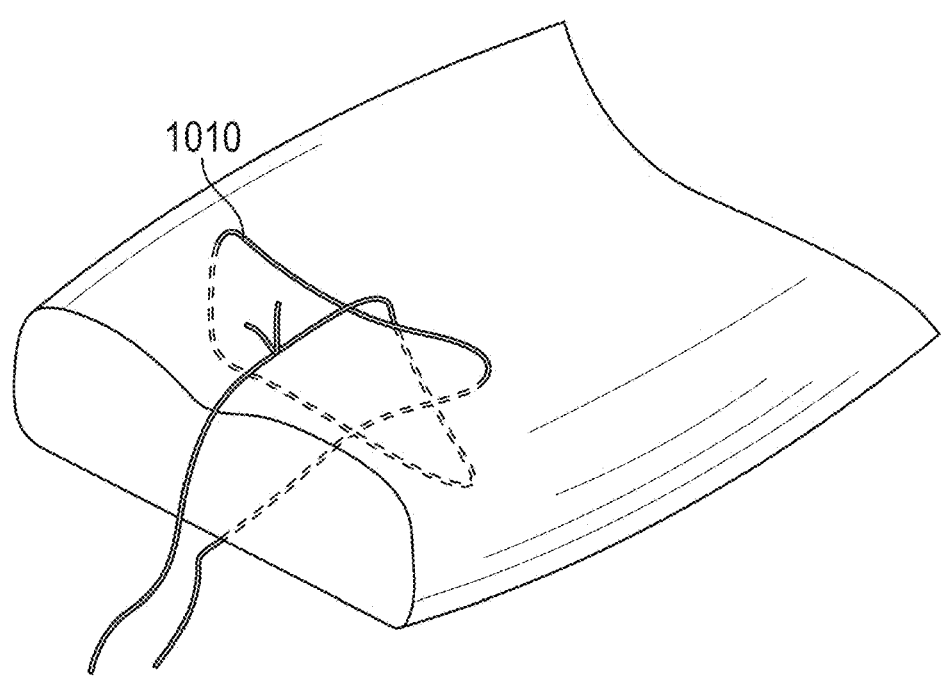
Figure 26T:
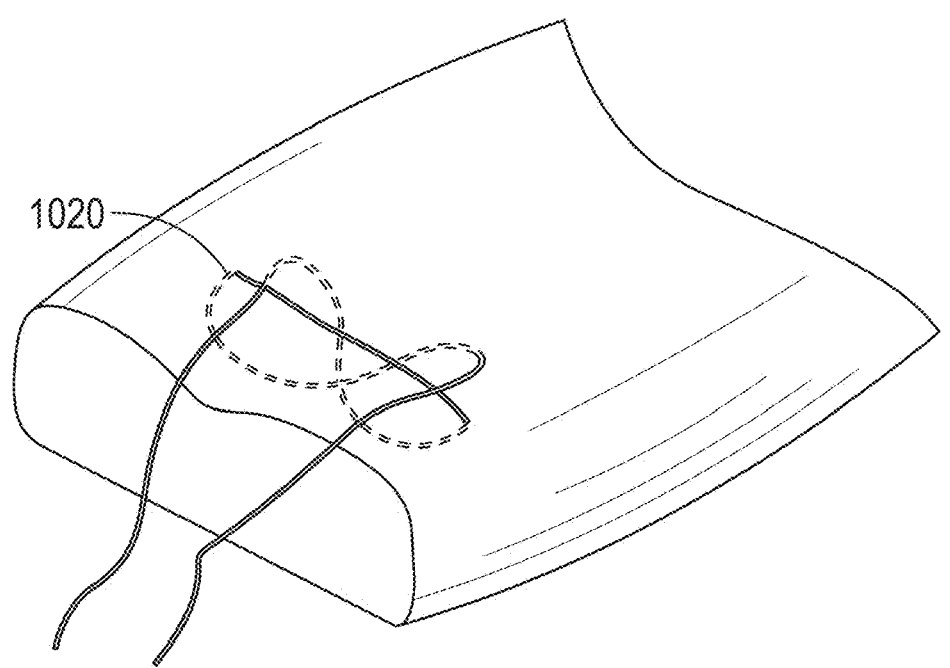
Figure 26U:
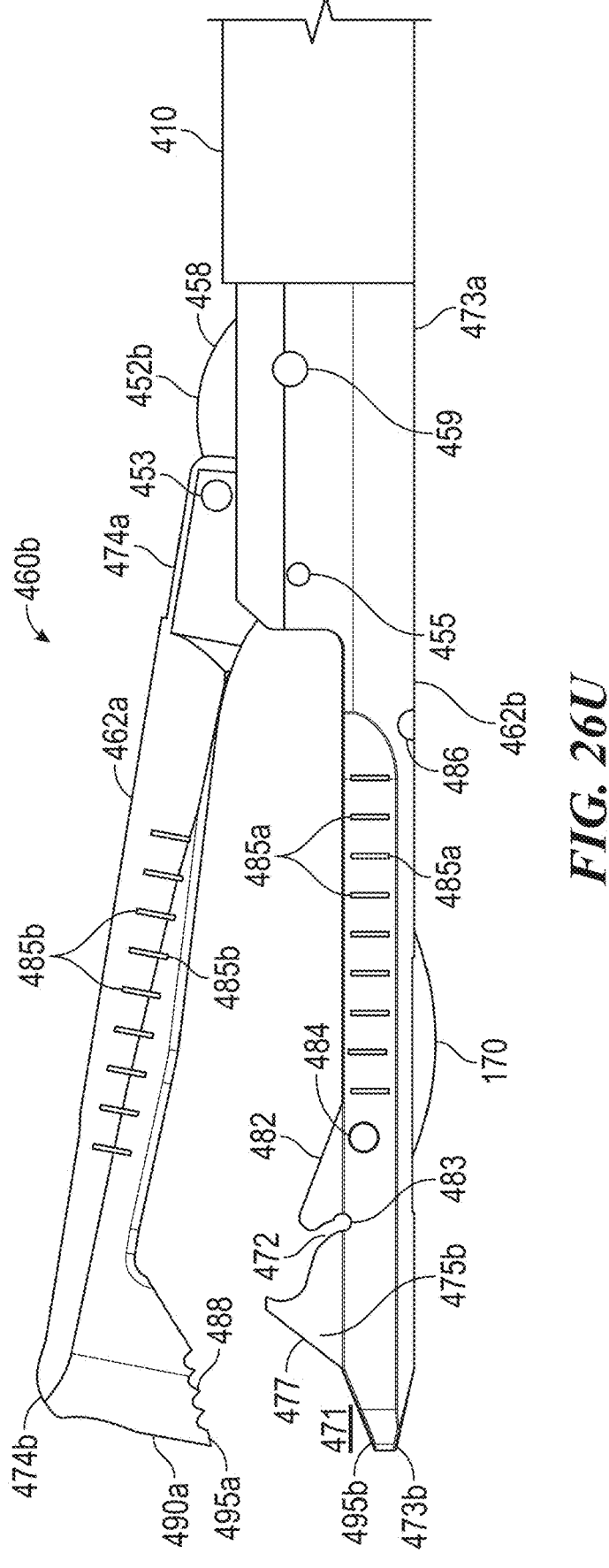
Figure 26V:
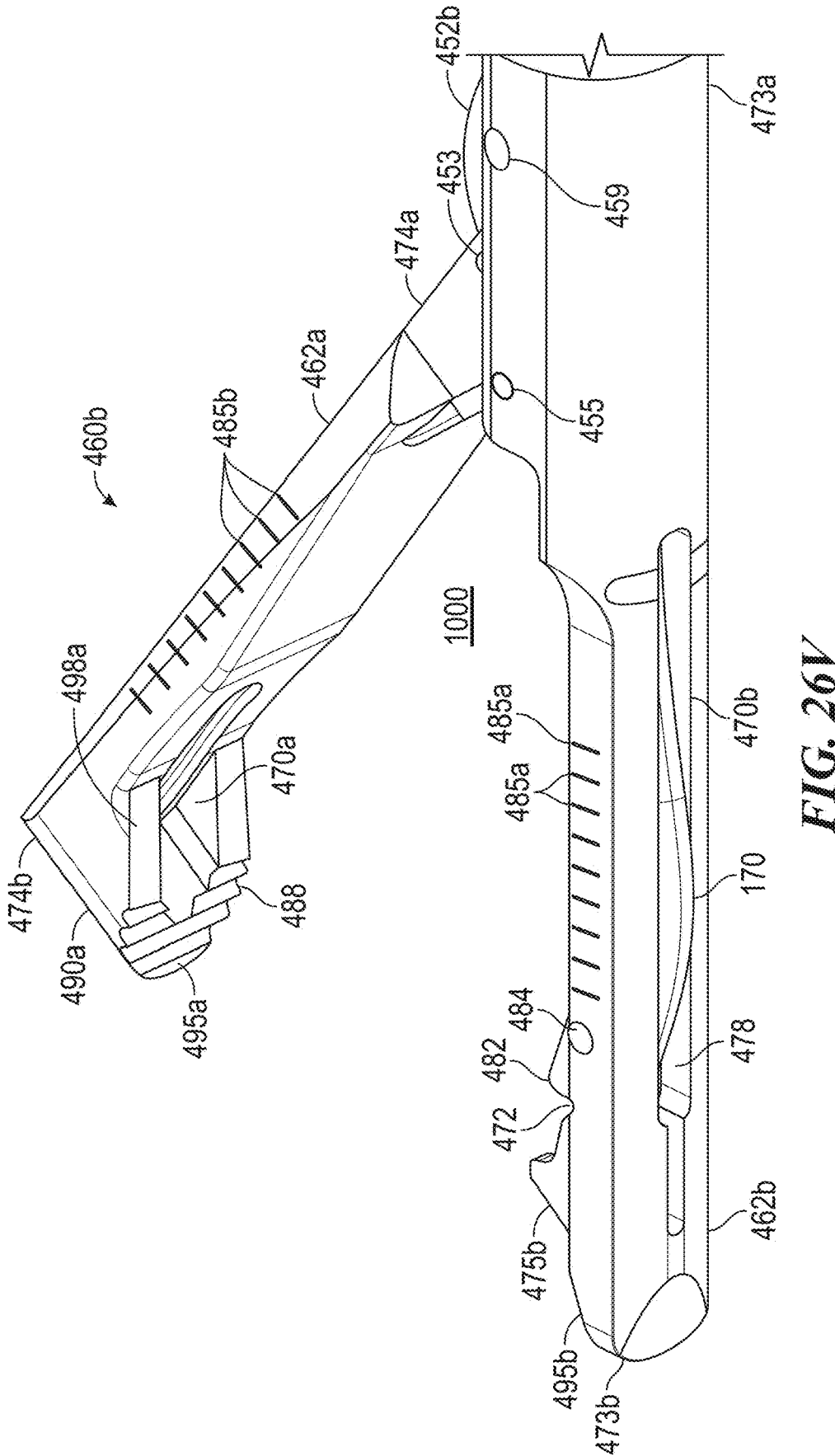
Figures 26W, 26X, 26Y:
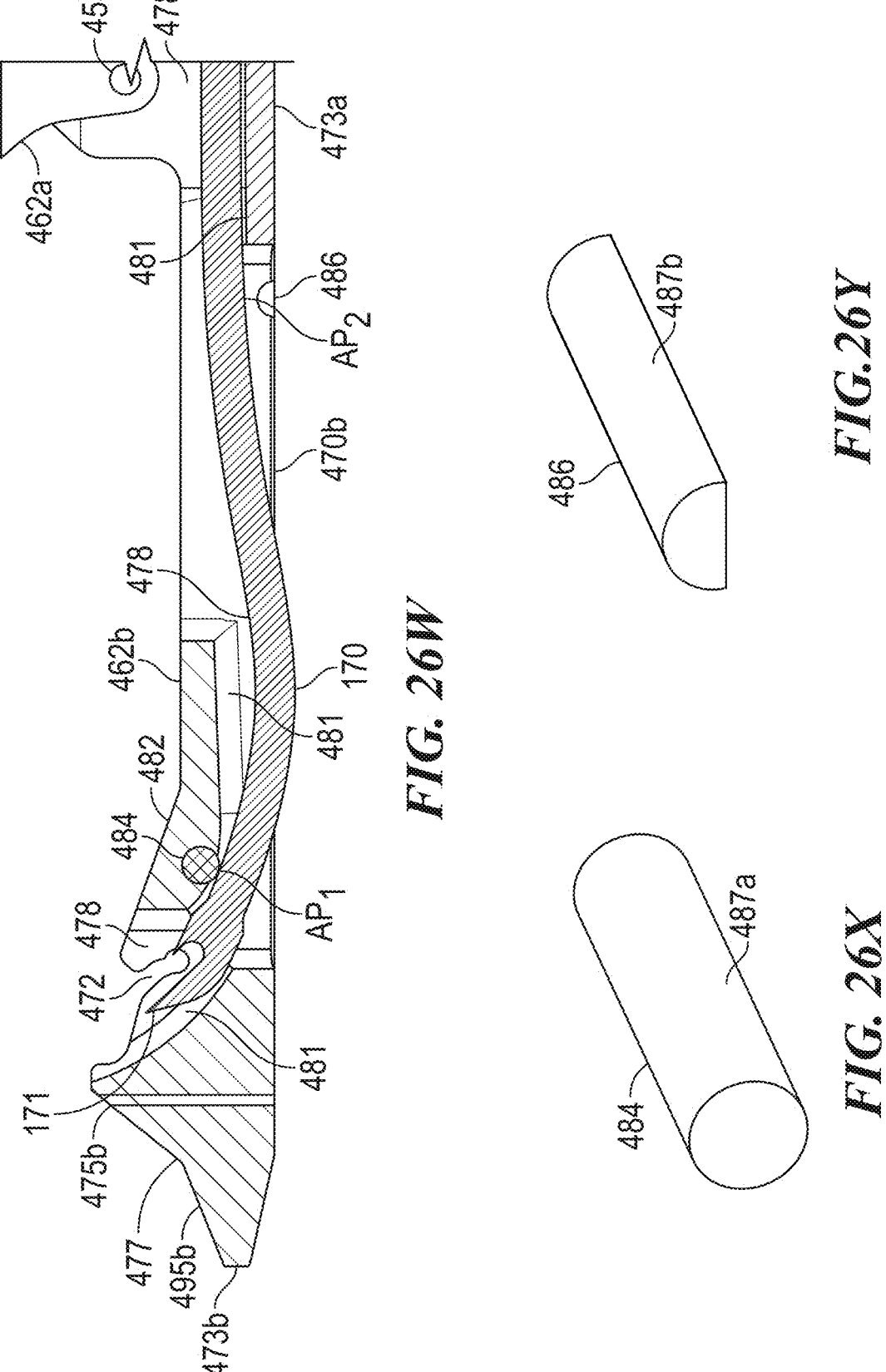
Figure 26Z:
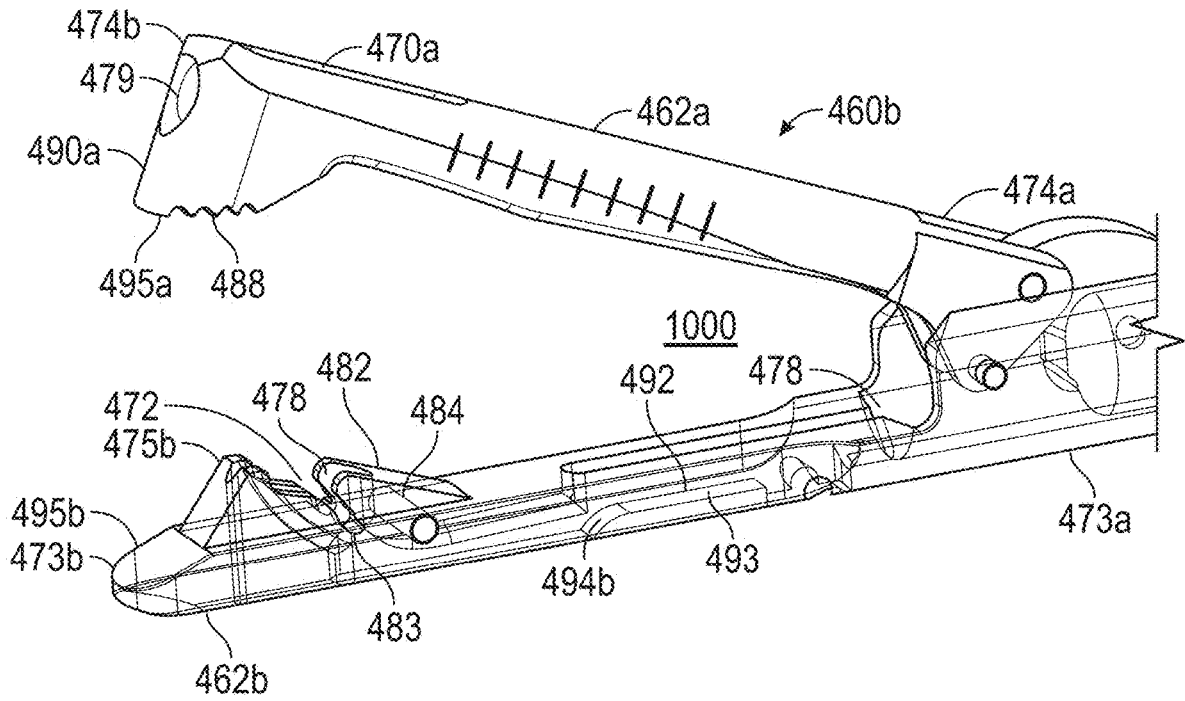

FIG. 3A is a partial perspective view of a lower jaw member of the system shown in FIG. 1A and a suture prior to loading in the lower jaw member, in accordance with the invention;

FIG. 3B is another perspective view of the lower jaw member shown in FIG. 3A showing the slot formed in the jaw member, in accordance with the invention;

FIG. 3C is a partial perspective partial sectional view of the lower jaw member, tubular needle, and suture shown in FIG. 3A, in accordance with the invention;

FIG. 4A is a partial perspective partial sectional view of the lower jaw member and tubular needle shown in FIG. 3A showing a cleat member engaged to the suture, in accordance with the invention;

FIG. 4B is a partial perspective view of the tubular needle shown in FIG. 3A and the cleat member disposed in the lumen thereof, in accordance with the invention;

FIG. 4C is a partial perspective view of the cleat member shown in FIG. 4B, in accordance with the invention;

FIG. 5A is a partial perspective view of the tubular needle shown in FIG. 4B comprising another embodiment of a cleat member disposed in the lumen thereof, in accordance with the invention;

FIG. 5B is a partial perspective view of the cleat member shown in FIG. 5A, in accordance with the invention;

FIG. 5C is a partial perspective view of the lower jaw member, tubular needle, the embodiment of the cleat member shown in FIG. 5A, and suture, in accordance with the invention;

FIG. 6A is a partial side view of the tubular needle that is extended to engage and carry the suture through the aperture of the jaw mechanism and pawl, in accordance with the invention;

FIG. 6B is a partial perspective view of the tubular needle that is extended to carry the suture through the aperture of the jaw mechanism and pawl shown in FIG. 6A, in accordance with the invention;

FIG. 6C is a perspective view of the suture captured by the pawl shown in FIG. 6A, in accordance with the invention;

FIG. 6D is a side plan view of the suture captured by the pawl shown in FIG. 6A, in accordance with the invention;

FIG. 7A is a partial perspective view of another embodiment of a suture passing device comprising two (2) tubular needles and a jaw mechanism with the two tubular needles extended through the aperture of the jaw mechanism, in accordance with the invention;

FIG. 7B is a partial perspective view of the hand grip, toggle switch and needle assemblies of the suture passing device shown in FIG. 7A, in accordance with the invention;

FIG. 8A is a side plan view of the jaw mechanism shown in FIG. 6A with a slot and floating pivot mechanism in the collapsed state, in accordance with the invention;

FIG. 8B is a perspective view of the floating pivot mechanism, in accordance with the invention;

FIG. 8C is a side plan view of the jaw mechanism shown in FIG. 6A with a slot and floating pivot mechanism in the expanded or vertically articulated state, in accordance with the invention;

FIGS. 9A-9C are side plan views of another embodiment of a suture passing system in various stages of deployment, in accordance with the invention;

FIG. 10A is a side plan partial sectional view of an elongated member distal tip and jaw mechanism of the suture passing system shown in FIG. 9A prior to loading a suture, in accordance with the invention;

FIG. 10B is a side plan view of a preformed tubular needle, in accordance with the invention;

FIG. 10C is a side plan partial sectional view of a preformed tubular needle retracted and constrained in the guide channel of the bottom jaw member, and the jaw mechanism set at a determined gap distance, in accordance with the invention;

FIG. 11A is a perspective view of the elongated member distal tip and jaw mechanism of the suture passing system shown in FIG. 10A showing the pawl feature, in accordance with the invention;

FIG. 11B is a side plan sectional view of the elongated member distal tip and jaw mechanism shown in FIG. 10A showing the guide channel track for the needle, in accordance with the invention;

FIG. 11C is another partial side view of the tubular needle shown in FIG. 10B comprising two segments to match a guide channel track profile, in accordance with the invention;

FIG. 12A is a perspective view of the suture passing system shown in FIG. 10A showing the elongated member distal tip, jaw mechanism, and tubular needle extended with suture, in accordance with the invention;

FIG. 12B is a partial perspective view of the tubular needle and cleat member of the suture passing system shown in FIG. 10A extended to engage and carry the suture through the aperture of the jaw mechanism, and pawl, in accordance with the invention;

FIG. 12C is a side plan sectional view of the elongated member distal tip, jaw mechanism, tubular needle and cleat member of the suture passing system shown in FIG. 10A, and the suture loaded on the distal end of the tubular needle, in accordance with the invention;

FIG. 13A is a partial perspective view of the tubular needle of the suture passing device shown in FIG. 10A with a front-loaded suture, in accordance with the invention;

FIG. 13B is a side plan sectional view of the elongated member distal tip, jaw mechanism, and tubular needle of the suture passing system shown in FIG. 10A with a front-loaded suture, in accordance with the invention;

FIG. 14 is a perspective view of another embodiment of the suture passing system comprising a jaw mechanism in the open position with the tubular needle fully retracted, showing the needle shield secured to the jaw mechanism top jaw member, in accordance with the invention;

FIG. 15 is a perspective view of tubular needle of the suture passing system shown in FIG. 14 that is extending from the guide channel of the bottom jaw member and transitioning from a constrained to an unconstrained configuration, in accordance with the invention;

FIG. 16 is a partial side plan view of the bottom jaw member of the jaw mechanism shown in FIG. 14 showing the suture loading slot that is disposed on a lateral side of the bottom jaw member, in accordance with the invention;

FIG. 17 is a perspective view of the jaw mechanism shown in FIG. 14 with the suture laterally loaded in the bottom jaw member, in accordance with the invention;

FIG. 18 is a perspective view of a tubular needle of the suture passing system shown in FIG. 14 extended from the guide channel of the bottom jaw member and transitioned from a constrained to an unconstrained configuration with a suture engaged thereto, in accordance with the invention;

FIG. 19 is a partial perspective view of the tubular needle shown in FIG. 18 with the cleat member engaged with the suture, in accordance with the invention;

FIG. 20 is a perspective view of the jaw mechanism of the suture passing system shown in FIG. 14, with the tubular needle shield in the default state, in accordance with the invention;

FIG. 21 is a perspective view of the jaw mechanism shown in FIG. 20 with the tubular needle shield in the deflected state, thereby, shielding the tubular needle distal end from surrounding tissue in a surgical site, in accordance with the invention;

FIG. 22 is a perspective view of the jaw mechanism shown in FIG. 20 with the needle shield in the deflected state, showing a window feature in the needle shield to prevent damage to the tubular needle distal end when the needle is extended into the needle shield, in accordance with the invention;

FIG. 23 is a perspective view of another embodiment of the suture passing system actuator, in accordance with the invention;

FIG. 24A is a perspective view of another embodiment of a jaw mechanism that is adapted to cooperate with the suture passing system actuator shown in FIG. 23, in accordance with the invention;

FIG. 24B is a partial side plan view of the jaw mechanism shown in FIG. 24A, in accordance with the invention;

FIG. 24C is a partial top plan view of the jaw mechanism shown in FIG. 24A, in accordance with the invention;

FIG. 24D is a further partial top plan view of the jaw mechanism shown in FIG. 24A, having a cut away section showing a top jaw member ribbon track and a suture retaining ribbon positioned therein, in accordance with the invention;

FIG. 24E is a partial perspective view of another embodiment of a system needle, in accordance with the invention;

FIG. 24F is a partial perspective view of a bottom jaw member of the jaw mechanism shown in FIG. 24A, showing a suture positioned thereon, in accordance with the invention;

FIG. 24G is a further partial perspective view of the bottom jaw member FIG. 24F, showing the suture captured by the system needle shown in FIG. 24E, in accordance with the invention;

FIG. 25 is a partial perspective view of another embodiment of a jaw mechanism comprising one embodiment of a fixed pivot mechanism, in accordance with the invention;

FIG. 26A is a side plan view of a multi-function jaw mechanism in an open position or configuration, in accordance with the invention;

FIG. 26B is a further side plan view of the multi-function jaw mechanism shown in FIG. 26A in a fully closed configuration, in accordance with the invention;

FIG. 26C is a partial side plan view of the bottom jaw member of the multi-function jaw mechanism shown in FIG. 26A, showing an embodiment of a raised distal guide region of the bottom jaw member, in accordance with the invention;

FIG. 26D is a further partial side plan view of the bottom jaw member of the multi-function jaw mechanism shown in FIG. 26A, showing another embodiment of a raised distal guide region of the bottom jaw member, in accordance with the invention;

FIG. 26E is a further partial side plan view of the bottom jaw member of the multi-function jaw mechanism shown in FIG. 26A, showing another embodiment of a raised distal guide region of the bottom jaw member, in accordance with the invention;

FIG. 26F is a partial side plan view of the multi-function jaw mechanism shown in FIG. 26B, showing the raised distal guide region of the bottom jaw member shown in FIG. 26C seated in the top jaw member of the multi-function jaw mechanism, in accordance with the invention;

FIG. 26G is a partial side plan view of the multi-function jaw mechanism shown in FIG. 26B, showing the raised distal guide region of the bottom jaw member shown in FIG. 26D seated in the top jaw member of the multi-function jaw mechanism, in accordance with the invention;

FIG. 26H is a partial side plan view of the multi-function jaw mechanism shown in FIG. 26B, showing the raised distal guide region of the bottom jaw member shown in FIG. 26E seated in the top jaw member of the multi-function jaw mechanism, in accordance with the invention;

FIG. 26I is a partial side plan view of the multi-function jaw mechanism shown in FIG. 26B, showing one embodiment of a suture backstop region of the multi-function jaw mechanism, in accordance with the invention;

FIG. 26J is a partial side plan view of the multi-function jaw mechanism shown in FIG. 26B, showing another embodiment of a suture backstop region of the multi-function jaw mechanism, in accordance with the invention;

FIG. 26K is a partial side plan view of the multi-function jaw mechanism shown in FIG. 26B, showing another embodiment of a suture backstop region of the multi-function jaw mechanism, in accordance with the invention;

FIG. 26L is further side plan view of the multi-function jaw mechanism shown in FIG. 26B, showing the gap formed between the top jaw member and suture engagement region of the bottom jaw member, when the multi-function jaw mechanism is in a closed jaw configuration, in accordance with the invention;

FIG. 26M is a side plan sectional view of the multi-function jaw mechanism shown in FIG. 26B, showing the open needle guide channel and track in the lower jaw member, in accordance with the invention;

FIG. 26N is a top plan view of the multi-function jaw mechanism shown in FIG. 26A, in accordance with the invention;

FIG. 26O is a side plan view of the multi-function jaw mechanism shown in FIG. 26A, showing the jaw mechanism in an open configuration with a suture disposed in the open internal region of the jaw mechanism, in accordance with the invention;

FIG. 26P is a side plan view of the multi-function jaw mechanism shown in FIG. 26A, showing the jaw mechanism in a closed configuration with the suture disposed in the open internal region of the jaw mechanism, in accordance with the invention;

FIG. 26Q is a side plan view of the multi-function jaw mechanism shown in FIG. 26A, showing the jaw mechanism in a closed configuration with the suture disposed in the suture containment region of the jaw mechanism, in accordance with the invention;

FIG. 26R is a side plan view of the multi-function jaw mechanism shown in FIG. 26A, showing the jaw mechanism in a closed configuration with the suture disposed in the suture loading slot of the lower jaw member of the jaw mechanism, in accordance with the invention;

FIG. 26S is an illustration of a Mason-Allen stitch pattern;

FIG. 26T is an illustration of a modified Mason-Allen stitch pattern;

FIG. 26U is a side plan view of the multi-function jaw mechanism shown in FIG. 26A, showing the jaw mechanism in a partially closed configuration, the aligned tissue engagement regions of the top and bottom jaw members and the means for measuring stitch placement positions in soft tissue, in accordance with the invention;

FIG. 26V is a side perspective view of the multi-function jaw mechanism shown in FIG. 26A, showing the open needle guide channel of the lower jaw member, in accordance with the invention;

FIG. 26W is a side partial perspective view of the bottom jaw member of the multi-function jaw mechanism shown in FIG. 26A, showing the needle disposed in the open needle guide channel, in accordance with the invention;

FIG. 26X is a perspective view of one embodiment of a distal needle wear resistance member, in accordance with the invention;

FIG. 26Y is a perspective view of one embodiment of a proximal needle wear resistance member, in accordance with the invention; and FIG. 26Z is a side perspective view of the multi-function jaw mechanism shown in FIG. 26A, showing the distal wear resistance member shown in FIG. 26X and a further embodiment of a second wear resistance member positioned in the lower jaw mechanism of the multi-function jaw mechanism, in accordance with the invention.

DETAILED DESCRIPTION OF THE PREFERRED EMBODIMENT

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with endoscopic procedures, the invention is not limited to such procedures. According to the invention, the systems, apparatus and methods of the invention can also be employed in connection with a multitude of other surgical procedures, including open surgical procedures.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The words used in the description to describe the invention and its various embodiments are to be understood not only in the sense of their commonly defined meanings, but to include by special definition in this specification the generic structure, material or acts of which they represent a single species.

The present invention relates generally to systems, apparatus and methods for advancing a needle and suture into and through soft tissue (typically, the needle will be affixed to a suture that remains in the tissue) using a cannula, introducer or other minimally invasive means. As discussed herein, the systems, apparatus and methods described herein can be used in any number of medical procedures, including, but not limited to, approximating tissue (e.g., bring separated tissue together), ligating tissue (e.g., encircling or tying off), and fixating of tissue (attaching tissue to another structure or different tissue or an implantable device).

Definitions

The terms "tissue", "soft tissue" and "biological tissue" are used interchangeably herein, and mean and include mammalian biological tissue, such as, by way of example, human abdominal tissue.

The term "biological cavity", as used herein, means and includes any cavity or space in a mammalian tissue structure.

The term "surgical site", as used herein, means and includes any space or region in a mammalian tissue structure where a surgical procedure is conducted.

The terms "endoscopy" and "endoscopic procedure", as used herein, mean and include any minimally invasive surgical procedure conducted through at least one opening in a subject's body, including, but not limited to arthroscopy, laparoscopy, hysteroscopy and the like.

The terms "system", "apparatus" and "device" are used interchangeably herein, and mean and include an assembly or component thereof that is configured and adapted to facilitate approximation, ligation and/or fixation of soft tissue.

The term "pharmacological agent", as used herein, means and includes an active agent, compound, composition or mixture thereof, including its formulation, which provides some therapeutic, often beneficial, effect. This includes any physiologically or pharmacologically active substance (or composition comprising same) that produces a localized or systemic effect or effects in animals, including warm-blooded mammals.

The term "pharmacological agent" thus means and includes, without limitation, antibiotics, anti-microbial agents, anti-viral agents, analgesic agents, anti-inflammatory agents, anti-neoplastic agents, anti-spasmodic agents, anticoagulant agents and agents the modulate proliferation and growth of tissue.

The term "pharmacological agent" thus means and includes, without limitation, the following antibiotics and compositions comprising same: penicillin, carboxypenicillins, such as ticarcillin, tetracyclines, such as minocycline, gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The term "pharmacological agent" thus also means and includes, without limitation, the following anti-inflammatory agents and compositions comprising same: dexamethasone, betamethasone, prednisone, prednisolone, methylprednisolone sodium succinate, methylprednisolone, cortisone, ketorolac, diclofenac and ibuprofen.

The term "pharmacological agent" thus also means and includes, without limitation, the following metal-based antimicrobials and compositions comprising same: silver particles, copper particles, cobalt particles, nickel particles, zinc particles, zirconium particles, molybdenum particles, lead particles and mixtures thereof.

The term "therapeutically effective", as used herein, means that the amount of the "pharmacological agent" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The phrase "in one configuration" or similar phrases employed herein do not necessarily refer to the same configuration and, unless specifically stated, do not limit the inclusion of a particular element of the invention to a single configuration. The element may thus be included in other, or all configurations discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all of the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The terms "patient" and "subject" are used interchangeably herein, and mean and include warm-blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present disclosure is directed to apparatus, systems and methods for approximating, ligating and/or fixating soft tissue; particularly, soft tissue that is accessed via an endoscopic procedure.

As is well known in the art, sutures are often employed in both open and endoscopic surgical procedures to approximate, ligate and fixate soft tissue or otherwise treat tissue. Generally, suture needles with attached suture are grasped either manually or by forceps and passed through the surgical site to approximate, ligate and fixate soft tissue.

Although such surgical procedures are relatively uncomplicated in open surgery procedures where most suture sites are readily accessible, surgeons must often use auxiliary devices to grasp the suture, i.e. strands thereof, and pass the suture through desired soft tissue in endoscopic procedures where access to a desired suture site is not readily available.

Referring now to FIG. 1A, there is illustrated one embodiment of a suture passing system of the present invention that is adapted to pass suture through soft tissue. As illustrated in FIG. 1A, the suture passing system comprises an elongated tubular body 10, a hand grip 20, a tip 30, a jaw mechanism 40, an actuator 50 and a needle assembly 60.

Figure 1B:
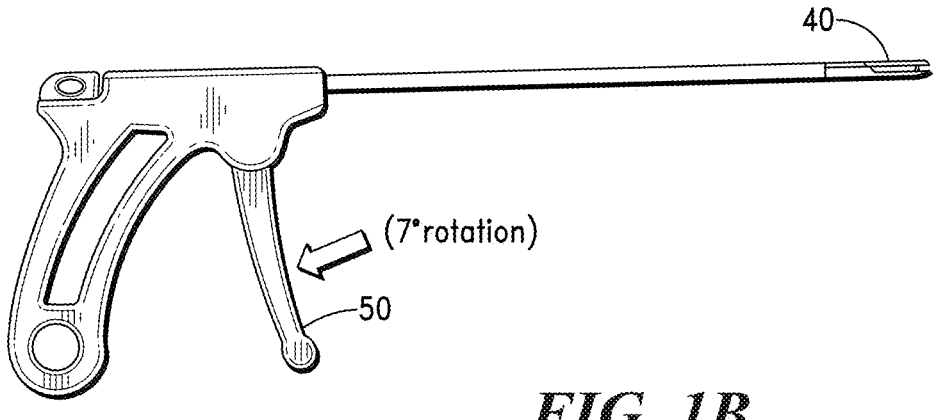
Figure 1C:
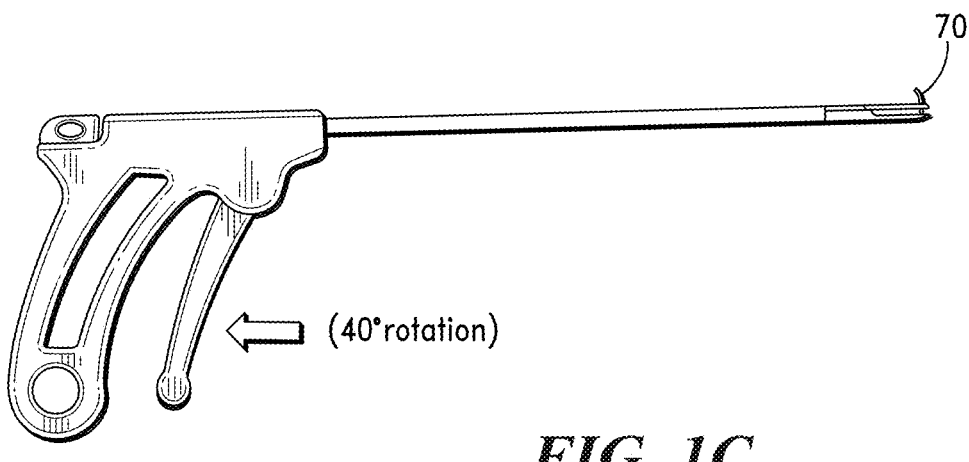

According to the invention, with actuator 50, a surgeon can seize and maintain soft tissue by movement of the jaw mechanism 40 against tip 30, as shown in FIG. 1B. Using actuator 50, a surgeon can also deploy a tubular needle 70 carrying a suture 71 through soft tissue, as shown in FIG. 1C and described below.

Figure 2A:
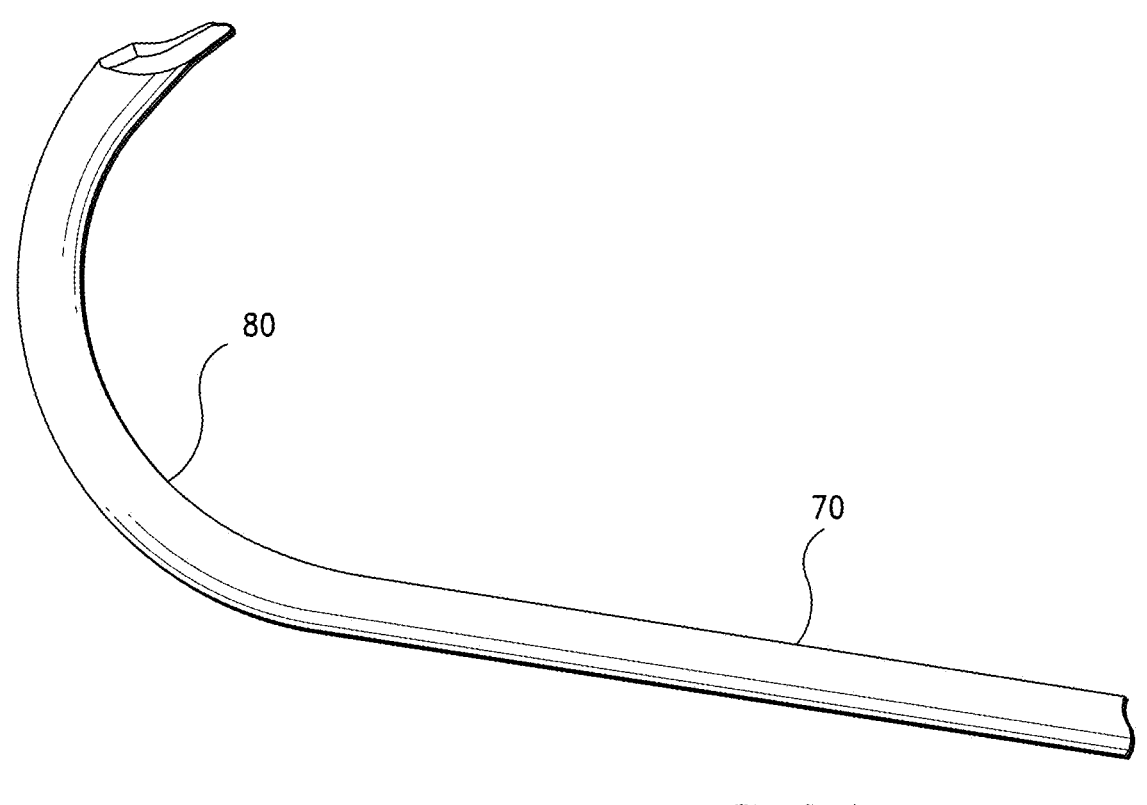
FIG. 2A is a partial side plan view of a notch-less tubular needle comprising a preformed memory shape, in accordance with the invention.

Referring now to FIG. 2A, there is illustrated one embodiment of a needle of the invention, i.e., a notchless tubular needle 70, in its natural, unconstrained state.

As used throughout the specification, the term "notchless" shall refer to the absence of notches, slots, eyelets, or other such transverse openings for receiving suture as typically formed in needles of prior art suture passers.

According to the invention, the needle 70 can also comprise a solid structure.

As illustrated in FIG. 2A, the distal end 80 of the needle 70 comprises a curvilinear configuration.

Figure 2B:
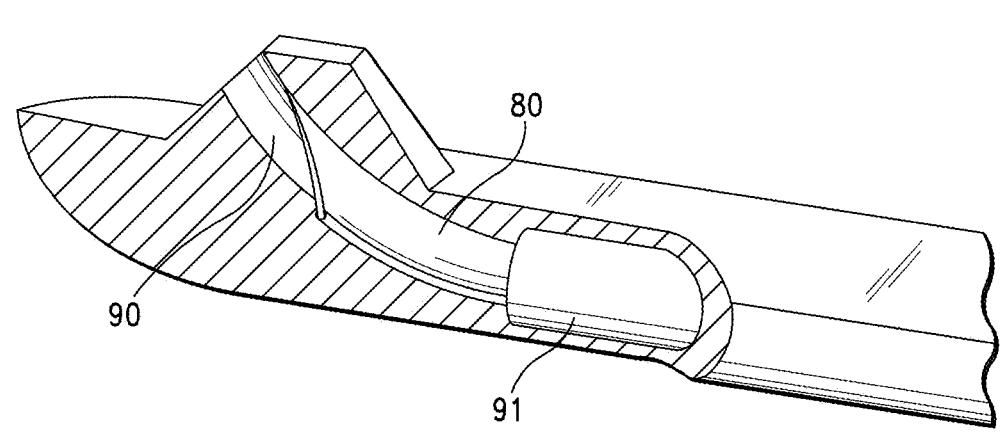
FIG. 2B is a partial side plan partial sectional view of a preformed tubular needle in a retracted, constrained state, in accordance with the invention.

As illustrated in FIG. 2B, the needle 70 comprises a formed end 80 sheathed in a constraining channel 91. In a preferred embodiment, the needle channel 91 also includes a curvilinear portion 90, or guide-path, which approximates the same geometry curve as the distal end 80 of the needle 70, thereby facilitating the consistent return of the needle 70 to its preformed curved shape each time the needle 70 exits the channel.

According to the invention, the constrained state needle 70 contained in the needle assembly 60 is loaded into the handle end of the elongated tubular body 10 and advanced through a guide channel or track in the tubular body 10.

FIG. 1A illustrates the hand grip 20 and actuator 50 of the suture passing device, which, as set forth in Applicant's U.S. Pat. No. 12,029,412, provide articulation of jaw 40 relative to tip 30.

As set forth in U.S. Pat. No. 12,029,412 and illustrated in FIGS. 3A and 3B, a loop of suture 71 is loaded into distal end of tip 30 with slot 31. According to the invention, the slot 31 facilitates spring action for gripping the loop of suture 71 when the loop of suture 71 is guided into the tip 30.

In one embodiment of the invention, illustrated in FIG. 3C, tubular needle 70 pierces the loop of suture 71 and, thereby, creates a bifurcation 72 in the suture 71.

According to the invention, when additional force is applied to the suture 71, the bifurcation 72 advances along the shaft of the needle 70.

As further set forth in U.S. Pat. No. 12,029,412 and illustrated in FIG. 4A, to prevent the bifurcation 72 from advancing along the shaft of the tubular needle 70, in some embodiments, a prong cleat 73 is positioned in the tubular needle 70 and adapted to pierce the loop of suture 71 loop in a second location. According to the invention, the pierce of the prong cleat 73 can partially engage the thickness of the suture 71 or create a second bifurcation 74 in the suture.

As illustrated in FIG. 4C, in a preferred embodiment, the prong cleat 73 comprises a wire rod or tube that is housed within the lumen 79 of the tubular needle 70. As further illustrated in FIG. 4C, the prong cleat 73 comprises a sharp distal tip, which slightly extends from the lumen 79 of the tubular needle 70, as illustrated in FIG. 4B. The piercing action of the needle 70 and the prong cleat 73 at different locations in the suture 71 act in conjunction to stabilize the suture 71 and prevent the suture 71 from advancing along the shaft of the needle 70.

Referring back to FIG. 3C, in another embodiment, tubular needle 70 pierces the loop of suture 71 and creates a bifurcation 72 in the suture 71. When additional force is applied to the suture 71, the bifurcation 72 advances along the shaft of the needle 70. To prevent the bifurcation 72 from advancing along the shaft of the needle 70, a lateral post cleat 75, illustrated in FIGS. 5A and 5B, is positioned to engage the bifurcated section of the suture 71, as illustrated in FIG. 5C.

Referring now to FIGS. 6A and 6B, there is illustrated one embodiment of a jaw mechanism 40 having an aperture 41 therein, which is sized and configured to receive tubular needle 70 and suture 71 and allow tubular needle 70 and suture 71 to pass therethrough.

As illustrated in FIGS. 6B and 6C, the jaw mechanism 40 further comprises a retractable pawl 42, which includes a window 43 that aligns with aperture 41 when the retractable pawl 42 is extended forward in the open position. When the tubular needle 70 and suture 71 are deployed within aperture 41 via actuator 50, the retractable pawl 42 is then moved to a retracted or rearward position, as illustrated in FIG. 6C. In some embodiments, the retractable pawl actuation mechanism includes a spring bias to provide a relatively constant force of the retractable pawl 42 against the deployed tubular needle 70 and suture 71.

As set forth in U.S. Pat. No. 12,029,412, upon release of the actuator 50, a spring in the actuator mechanism returns the tubular needle 70 to the constraining channel 90. The spring bias of the retractable pawl 42 allows the tubular needle 70 to return yet allows the retractable pawl 42 to maintain a grip on the suture 71 and pulls it in a rearward movement to become captured in between the proximal edge 44 of the aperture 41 in the jaw 40 and distal edge 47 of pawl window 43, as is shown in FIGS. 6C and 6D. Complete release of the actuator 50 disengages the jaw mechanism 40 to the default open position, thus, completing the passage of suture 71 through the soft tissue.

As further set forth in U.S. Pat. No. 12,029,412, in some embodiments, the suture passing system is configured to comprise two (2) or more tubular needles 70. In one embodiment, the suture passing system can throw more than one segment of suture 71 through soft tissue simultaneously. An exemplar two (2) needle suture passing device is illustrated in FIG. 7A, which shows a left tubular needle 70a and a right tubular needle 70b after being released to their natural states.

The segments of suture being passed by multiple tubular needles 70 can be attached to form a continuous loop of suture, thus enabling the formation of a desired suture pattern, e.g., a horizontal mattress stitch.

In some embodiments of the invention, the suture passing system is configured to deploy the left needle 70a and right needle 70b independently.

Referring now to FIG. 7B, there is illustrated another embodiment of handle mechanism 20 that is adapted to modulate multiple needles independently. As illustrated in FIG. 7B, the handle mechanism 20 comprises a switch 61 to toggle and engage one needle assembly at a time in the drive track 60. When the switch 61 of the handle mechanism 20 is toggled to engage the left needle assembly 64, the jaw mechanism 40 can be actuated to grasp a desired location of soft tissue and the left tubular needle 70a is deployed to pass and capture suture in a first soft tissue location.

As further set forth in U.S. Pat. No. 12,029,412, fully releasing the actuator 50 returns the left tubular needle 70a to its constrained state and disengages jaw mechanism 40. The suture passing device can then be repositioned to a second desired soft tissue location. When the switch 61 is toggled to engage the right tubular needle 70b, the jaw mechanism 40 can be actuated to grasp a second desired location of soft tissue and the right needle 70b is deployed to pass and capture suture in a second soft tissue location. Fully releasing the actuator 50 returns the right tubular needle 70b to its constrained state and disengages jaw mechanism 40 from soft tissue. The suture passing system can then be removed from the cannula to expose the two ends of the suture.

As further set forth in U.S. Pat. No. 12,029,412 and illustrated in FIGS. 8A-8C, in some embodiments, the suture passing system described above comprises a floating pivot mechanism to facilitate a lower profile when the jaw mechanism 40 and tip 30 are separated. In some embodiments, the jaw mechanism 40 thus includes a pivot interface 36 with a linkage 35. At the opposite end of linkage 35 is another pivot interface 37 that joins linkage 35 and drive rod 38.

As illustrated in FIGS. 8A and 8B, the tip 30 includes a slot 31 in which a pin 39a slidably translates within. The pin 39a is fixed to jaw mechanism 40. Axial movement of drive rod 38 in relation to the tip 30 causes jaw mechanism 40 to rotate about pin 39a in relationship to the tip 30.

As further illustrated in FIGS. 8A and 8B, a leaf spring 45 exerts a force on the pin 39a to bias the pin 39a against the lower end of slot 31, thus, resulting in the jaw mechanism 40 being positioned in a collapsed state and the gap 92 between the inner surfaces of the tip 30 and jaw mechanism 40 being minimized.

The collapsed state of the jaw mechanism 40 is advantageous for providing a minimum profile for advancing the device through an access cannula. According to the invention, the device can be configured to be advanced into the through an access cannula having a diameter in the range of 2.0 mm-15.0 mm, more preferably, in the range of 5.0 mm-8.0 mm.

When the tip 30 and jaw mechanism 40 are positioned proximate soft tissue, advancement of the drive rod 38 causes the jaw mechanism 40 to rotate about pin 39a to clamp onto the tissue. The resisting force of the soft tissue to compression between tip 30 and the jaw mechanism 40 results in a force applied to the inner surface of the jaw mechanism 40. If the force applied to the inner surface of the jaw mechanism 40 exceeds the force of the leaf spring 45 provided to hold the pin 39a against the lower end of slot 31, the pin 39a will ride up the slot 31, and increase the gap 92 between the inner surfaces of tip 30 and the jaw mechanism 40, as illustrated in FIG. 8C.

In some embodiments, the gap 92 between the inner surfaces of tip 30 and the jaw mechanism 40 comprises a width in the range of 0.5 mm-5.0 mm, more preferably, a width in the range of 1.5 mm-3.3 mm.

Referring now to FIGS. 9A-9C, there is shown another embodiment of a suture passing system 100 at various stages of actuation. As illustrated in FIG. 9A, the suture passing system 100 of the present invention comprises a hand grip 102 in operative communication with elongated tubular body or member 104 having a distal end 110.

As further illustrated in FIG. 9A, hand grip 102 comprises a proximal end 103, an actuator 106 and a needle assembly 108, and elongated tubular member 104 comprises a jaw mechanism 112 having top and bottom jaw members 114a, 114b disposed proximate the elongated tubular member 104 distal end 110. In a preferred embodiment, the jaw mechanism 112 top and bottom jaw members 114a, 114b comprise proximal and distal ends.

In a preferred embodiment, the jaw mechanism 112 of the suture passing system 100 similarly comprises the floating pivot mechanism and pivot interface discussed above and shown in FIGS. 8A-8C to facilitate a lower profile when the top and bottom jaw members 114a, 114b of jaw mechanism 112 are separated and during axial articulation of the top and bottom jaw members 114a, 114b.

In the noted embodiments, the jaw mechanism 112 preferably comprises first and second pins 39a, 39b, the proximal end of the jaw mechanism 112 top jaw member 114a comprises first and second pin lumens, and the proximal end of the jaw mechanism 112 bottom jaw member 114b comprises a third pin lumen and a pin slot 31.

Preferably, the first pin lumen and the pin slot 31, and the second and third pin lumens are in axial alignment.

In a preferred embodiment, the jaw mechanism 112 top jaw member 114a first pin lumen and the bottom jaw member 114b pin slot 31 are configured to receive and position the jaw mechanism 112 first pin 39a, wherein, when the jaw mechanism 112 first pin 39a is received by and positioned in the jaw mechanism 112 top jaw member 114a first pin lumen and the bottom jaw member pin slot 31, the jaw mechanism 112 top jaw member 114a is allowed to vertically or linearly articulate with respect to the jaw mechanism 112 bottom jaw member 114b.

In a preferred embodiment, the jaw mechanism 112 top jaw member 114a second pin lumen and the bottom jaw member 114b third pin lumen are configured to receive and position the jaw mechanism 112 second pin 39b, wherein, when the jaw mechanism 112 second pin 39b is received by and positioned in the jaw mechanism 112 top jaw member 114a second pin lumen and the bottom jaw member third pin lumen, the jaw mechanism 112 top jaw member 114a is allowed to axially or rotatably articulate with respect to the jaw mechanism 112 bottom jaw member 114b.

According to the invention, any of the embodiments of the jaw mechanisms described herein can comprise the floating pivot mechanism and pivot interface discussed above and shown in FIGS. 8A-8C.

According to the invention, the suture passing system 100 can be used to capture and maintain soft tissue by positioning the jaw mechanism 112 of the suture passing device 100 proximate the soft tissue applying a first radial force on the actuator 106 to transition the top and bottom jaw members 114a, 114b of jaw mechanism 112 from an open configuration, as illustrated in FIG. 9A, to a closed configuration, as illustrated in FIG. 9B. A second radial force can also be applied to actuator 106 to deploy a tubular needle 116 having a suture attached thereto into and through the tissue, as illustrated in FIG. 9C and discussed in detail below.

In a preferred embodiment, the actuator 106 provides axial articulation of top jaw member 114a relative to bottom jaw member 114b of jaw mechanism 112. In some embodiments, the actuator 106 can be coupled to a return spring (not shown) that biases the actuator 106 in the open configuration shown in FIG. 9A.

In some embodiments of the invention, the actuator 106 of the hand grip 102 comprises a spring-loaded mechanism that is configured to provide a resistance force on the actuator 106 to provide tactile feedback for the operator to indicate that the tubular needle 116 is slidably translating into and through the jaw mechanism 112.

Referring now to FIG. 10A, there are shown top and bottom jaw members 114a, 114b of jaw mechanism 112 in an open configuration. As illustrated in FIG. 10A, the top jaw member 114a comprises a guide channel 118a and the bottom jaw member 114b comprises a guide channel 118b. In a preferred embodiment, the guide channels 118a, 118b are sized and configured to receive tubular needle 116 of the invention therein.

As further illustrated in FIG. 10A, in a preferred embodiment, guide channel 118b is in aligned communication with the elongated member 104 internal lumen 105.

Referring now to FIGS. 10B and 11C, there is shown tubular needle 116 in a first natural, unconstrained state comprising a distal end 120 and internal lumen 122. As illustrated in FIG. 10B, the tubular needle 116 comprises a formed curvilinear portion 150.

In some embodiments, the tubular needle 116 comprises multiple curvilinear sections 150 to slidably translate into and through the guide channels 118a, 118b. According to the invention, the curvilinear portion 150 of the tubular needle can comprise any suitable shape where 6.0% strain is not exceeded.

In a preferred embodiment, the tubular needle 116 comprises nickel-titanium alloy (Nitinol®) and is configured to transition (or deform) from an unconstrained or natural state to a constrained state, and from the constrained state back to the unconstrained state. As illustrated in FIG. 10B, in a preferred embodiment, the unconstrained state tubular member 116 comprises formed curvilinear portion 150.

As shown in FIG. 10C, in some embodiments, the tubular needle 116 is adapted to transition or deform into a constrained state when the curvilinear portion 150 of the tubular needle 116 is advanced through the elongated tubular member 104 internal lumen 105 and into guide channel 118b of the jaw mechanism 112 bottom jaw member 114b.

In some embodiments, the curvilinear portion 150 of the tubular needle 116 is adapted to reassume a curvilinear shape upon further advancement out of guide channel 118b and into and through guide channel 118a of the jaw mechanism 112 top jaw member 114a.

In some embodiments, the tubular needle 116 comprises a hollow and rigid structure. In some embodiments, the tubular needle 116 comprises geometry where the area moment of inertia about the neutral bending axis is in the range of $20.0 \times 10^{-9}$-$300.0 \times 10^{-9}$ inches to the $4^{th}$ power, more preferably, the tubular needle comprises a geometry where the area moment of inertia about the neutral bending axis in the range of $25.0 \times 10^{-9}$-$75.0 \times 10^{-9}$ inches to the $4^{th}$ power, which allows the tubular needle 116 to be driven into soft tissue with minimal deflection or skiving.

According to the invention, the tubular needle 116 distal end 120 can comprise various configurations, including, but not limited to, a beveled, curved, and serrated edge, which is configured to pierce through soft tissue.

In a preferred embodiment, the tubular needle 116 distal end 120 comprises a beveled edge having an angle "α" in the range of approximately 1°-90° with respect to the longitudinal axis "LA" of the tubular needle 116. More preferably, the angle "α" of the beveled distal end 120 is in the range of approximately 45°-90°.

In some embodiments, the needle 116 comprises a solid structure.

Referring now to FIG. 10C, there are shown top and bottom jaw members 114a, 114b of jaw mechanism 112 in a closed configuration comprising tubular needle 116 disposed in the guide channel 118b of bottom jaw member 114b. As illustrated in FIG. 10C, the top and bottom jaw members 114a, 114b of jaw mechanism 112 comprise a reciprocating curvilinear configuration that is configured to align guide channels 118a, 118b and, thereby, approximate the same curvilinear shape or configuration as the formed curvilinear portion 150 of the tubular needle 116 when the jaw mechanism 112 is in a closed configuration.

As further illustrated in FIG. 10C, when the top and bottom jaw members 114a, 114b of jaw mechanism 112 are in a closed configuration the top and bottom jaw members 114a, 114b are configured to be partially closed at a set distance $d_1$ from each other.

In some embodiments, the top and bottom jaw members 114a, 114b are configured to fully close to facilitate passage through an access cannula.

In a preferred embodiment, the needle assembly 108 and the tubular needle 116 in communication therewith are engaged to the proximal end 103 of hand grip 102 and the tubular needle 116 is slidably transitioned into and through the elongated tubular member 104 internal lumen 105 in a constrained state.

Referring now to FIGS. 11A and 11B, there is illustrated pawl 124 of the top jaw member 114a of jaw mechanism 112. As illustrated in FIGS. 11A and 11B, the pawl 124 comprises a distal end 126 and intersects the guide channel 118a and, hence, the path defined by the guide channel 118a.

As further illustrated in FIG. 11A, the bottom jaw member 114b of jaw mechanism 112 comprises a capture lip 128 that is configured to facilitate the capture of a portion of suture 71 shown in FIG. 12B.

As further set forth in U.S. Pat. No. 12,029,412, in some embodiments, the pawl 124 is used as a suture capturing mechanism. Referring now to FIG. 12C, when the tubular needle 116 guides the suture 71 into the guide channel 118a the pawl 124 is deflected, which allows the suture 71 to be guided beyond the distal end 126 of the pawl 124 by tubular needle 116.

According to the invention, when the tubular needle 116 is retracted from the guide channel 118a past the pawl 124, the distal end 126 of pawl 124 exerts a closure force on the suture 71 and captures the suture 71 between the pawl 124 distal end 126 and the inner wall 119 of guide channel 118*a*.

Referring now to FIGS. 12B and 12C, there is shown suture 71 having a distal end 77 that is loaded onto the distal end 120 of the tubular needle 116. As illustrated in FIGS. 12B and 12C, the distal end 120 of tubular needle 116 is configured to pierce at least a portion of suture 71.

As further illustrated in FIG. 12B, in a preferred embodiment, the distal tip 120 of tubular needle 116 is configured to pierce and form a bifurcation 72 in the suture 71.

As illustrated in FIGS. 12B and 12C, in some embodiments, the tubular needle 116 comprises a cleat member 130 having a piercing distal end 132 and is positioned in the tubular needle 116 internal lumen 122 and configured to pierce and engage at least a portion of the suture 71.

In a preferred embodiment, the tubular needle 116 distal end 120 and the cleat member 130 distal end 132 are adapted to pierce and engage suture 71 at two (2) predetermined locations on the suture 71 to secure the suture 71 thereto.

Referring now to FIGS. 13A and 13B, there is illustrated distal end 77 of suture 71 front loaded into the internal lumen 122 of the tubular needle 116 distal end 120. As illustrated in FIGS. 13A and 13B, the bend in the distal end 77 of the suture 71 provides a strain relief section that functions to releasably secure the distal end 77 of the suture 71 to the tubular needle 116 distal end 120 for penetration and advancement into soft tissue. According to the invention, when the tubular needle 116 is retracted from soft tissue, at least a portion of suture 71 is captured and retained by the soft tissue.

As illustrated in FIG. 13B, in some embodiments, the suture 71 distal end 77 is engaged by the distal end 126 of pawl 124, wherein the suture 71 distal end 77 is captured between the distal end 126 of pawl 124 and the inner wall 119 of the guide channel 118*a*.

Referring now to FIGS. 14-19, there is shown another embodiment of a jaw mechanism (now denoted "212") comprising top and bottom jaw members 214*a*, 214*b* and a suture retriever component (or needle shield) 250 that is secured to the jaw mechanism 212 top jaw member 214*a*.

As illustrated in FIGS. 14-16, the jaw mechanism 212 bottom jaw member 214*b* similarly comprises a guide channel 218*b* that is configured to receive tubular needle 116 having cleat member 130 disposed in the internal lumen 122 thereof. As further illustrated in FIGS. 14-16, in a preferred embodiment, the guide channel 218*b* comprises a curvilinear shape or geometry that is configured to approximate the same curvilinear shape or configuration as the formed curvilinear portion 150 of the tubular needle 116.

In a preferred embodiment, guide channel 218*b* is in aligned communication with the elongated member 104 internal lumen 105.

As illustrated in FIG. 16, the jaw mechanism 212 bottom jaw member 214*b* comprises a suture loading slot 232 that transects the guide channel 218*b* of the bottom jaw member 214*b*.

As illustrated in FIG. 17, in a preferred embodiment, the suture 71 is loaded into the suture loading slot 232 from either lateral side, whereby the suture 71 is allowed to slidably translate therethrough and intersect a path defined by the guide channel 218*b*, wherein the suture 71 can be engaged by the tubular needle 116 as it is slidably translated through guide channel 218*b*.

As illustrated in FIGS. 18 and 19, in a preferred embodiment, when the tubular needle 116 comprising cleat member 130 disposed therein is slidably translated through guide channel 218*b*, the cleat member 130 distal end 132 pierces and engages at least a portion of suture 71. As the tubular needle 116 is slidably translated further through the guide channel 218*b* of the jaw mechanism 212 bottom jaw member 214*b*, the tubular needle 116 drives the portion of suture 71 forward and into the window 254 of the jaw 212 mechanism top jaw member 214*a*.

As further illustrated in FIG. 18, in a preferred embodiment, the curvilinear portion 150 of the tubular needle 116 is adapted to transition from a constrained state to an unconstrained state and reassume a curvilinear, unconstrained shape upon further advancement out of guide channel 218*b*.

Referring now to FIGS. 20-22, when the tubular needle 116 is slidably translated through the guide channel 218*b* and into the window 254 of the jaw mechanism 212 top jaw member 214*a*, the tubular needle 116 is guided into needle shield 250. As illustrated in FIG. 20, in a preferred embodiment, the needle shield 250 comprises a deflecting trapdoor mechanism that is configured to prevent the tubular needle 116 from penetrating soft tissue and bone beyond the top jaw member 214*a* and damaging the soft tissue and bone. In a preferred embodiment, the needle shield 250 is configured to deflect and flex when the tubular needle 116 distal end 120 is slidably translated into the needle shield 250.

In a preferred embodiment, the needle shield 250 of the jaw mechanism 212 top jaw member 214*a* enables antegrade and retrograde passing of suture 71 during an endoscopic procedure, which allows an operator to generate a wide variety of stitch patterns in soft tissue including, without limitation, modified Mason-Allen, mattress, sliding mattress, Mason-Allen, far-near-near-far, Bunnell-Mayer, three-loop pulley, locking loop, modified Kessler, simple interrupted, simple continuous, Ford interlocking, interrupted cruciate, interrupted horizontal mattress, continuous horizontal mattress, interrupted vertical mattress, quilled, interrupted or continuous Lembert, interrupted quilt, Cushing, Connel, Parker-Kerr, purse string and modified variants thereof.

In some embodiments, the needle shield 250 is configured to provide a closure force that captures the suture 71 when the tubular needle 116 is retracted and the needle shield 250 is relieved from the force applied to the needle shield 250 by slidable translation of the tubular needle 116.

As illustrated in FIGS. 20-22, in a preferred embodiment, the needle shield 250 comprises a window member 252 that is configured to protect the distal end 120 of tubular needle 116 from damage. According to the invention, the needle shield 250 can comprise other features to protect the distal end 120 of tubular needle 116, such as a coined recess or other geometry that is configured to receive the distal end 120 of tubular needle 116 without damaging the distal end 120.

According to the invention, the window member 252 can comprise any shape or size suitable to receive the distal end 120 of tubular needle 116 without damaging the distal end 120.

Referring now to FIGS. 23-25, there is shown another embodiment of a suture passing system of the invention (denoted "400").

As illustrated in FIGS. 23 and 24A, the suture passing system 400 similarly comprises a body 402, comprising proximal and distal ends 401*a*, 401*b*, a handle 404, a trigger 406, and an elongated member or shaft 410 that similarly comprises a jaw mechanism (denoted "460*a*" in this embodiment), which is adapted to grasp soft tissue.

As illustrated in FIGS. 24A and 24B, the jaw mechanism 460a similarly comprises top and bottom jaw members 461a, 461b. As further illustrated in FIGS. 24A and 24B, the bottom jaw member 461b similarly comprises a guide channel 478 that is configured to receive a needle of the invention; preferably, needle 170 illustrated in FIG. 24E and discussed below, therein, and a suture loading slot 472 that similarly allows a suture 71, to be loaded therein from either lateral side of the jaw mechanism 460a, as illustrated in FIG. 24F, whereby the suture 71 can be engaged by the needle 170 as it slidably translates through the guide channel 478, as illustrated in FIG. 24G.

Referring now to FIG. 24E, there is shown a plan view of needle 170. As illustrated in FIG. 24E, the needle 170 comprises a suture ensnarement end 171 comprising a suture piercing region 171a and a suture retaining region 171b. As further illustrated in FIG. 24E, the suture piercing region 171a and the suture retaining region 171b forming a suture seat 171c therebetween, which, as illustrated in FIG. 24G, is configured to seat a suture therein.

In a preferred embodiment, the suture retaining region 171b of needle 170 is disposed in a low strain region of the needle 170.

As illustrated in FIG. 24E, the needle 170 further comprises a curvilinear region (denoted "CR") disposed on the distal end thereof.

In a preferred embodiment, the curvilinear portion "CR" of needle 170 comprises a bend radius that is in the range of approximately 10.0% to 80.0% greater than the track radius of the guide channel 478.

As illustrated in FIGS. 24B and 24C, in a preferred embodiment, the top jaw member 461a of the jaw mechanism 460a comprises a side wall opening 476 and hook 481, which facilitates suture capture in a surgical site.

As further illustrated in FIG. 24B, in a preferred embodiment, the bottom jaw member 461a comprises a raised distal guide region 475 proximate the distal end 473b of the bottom jaw member 461b, and the top jaw member 461a comprises side wall opening 476, which is sized and configured to restrict access of a suture, e.g., suture 71, into the jaw mechanism 460a from the distal end 474b thereof and, hence, further facilitate suture capture from a lateral side of the jaw mechanism 460a.

As further illustrated in FIGS. 24A and 24B, in one embodiment, the jaw mechanism 460a further comprises the aforementioned floating pivot mechanism (denoted "451").

In the noted embodiment, the floating pivot mechanism 451 thus comprises a first pin 453, which is sized and configured to be positioned in a first pin lumen (not shown) in the top jaw member 461a, a second pin 455, which is sized and configured to be positioned in a second pin lumen 457 in the top jaw member 461a, a third pin lumen in link 452a, and a floating pin slot 456 in the bottom jaw member 461b.

According to the invention, the floating pivot mechanism 451 operates in a similar manner and provides the same features and advantages as the floating pivot mechanism illustrated in FIGS. 8A and 8C and discussed above.

Referring now to FIG. 25, in some embodiments, the jaw mechanism 460a comprises a simple pin 453 that defines a pivot point, wherein the top and bottom jaw members 461a, 461b are in pivotal communication and the top jaw member 461a axially articulates with respect to the bottom jaw member 461b.

As set forth in priority U.S. application Ser. No. 18/623, 903, now U.S. Pat. No. 12,390,213, suture passing system 400 also comprises the following control systems: (i) a jaw articulation control system that is adapted to modulate articulation of jaw mechanism 460a, (ii) a needle articulation control system that is adapted to modulate translation and articulation of needle 170, and a suture control system that is adapted to modulate engagement, retainment and release of suture 71.

As further set forth in U.S. application Ser. No. 18/623, 903, the suture passing system 400 also comprises a multi-function actuation system that is configured to control the jaw articulation control system, needle articulation control system and suture control system.

The preferred multi-function actuation system (denoted "405") is configured to provide the following synchronized functions during a single continuous rotational (or angular) articulation of a system trigger (denoted 406) from a default position, i.e., 0° rotation, to a fully actuated position: (i) articulation of the system jaw mechanism 460a, (ii) suture control, i.e., suture engagement, retainment and release, by the jaw mechanism 460a, and (iii) translation and positioning of the system needle 170. The multifunction actuation system 405 is also configured to provide the same functions in reverse order during continuous rotational articulation of the system trigger 406 from the fully actuated position to the default position, i.e., upon release of the trigger 406.

Referring now to FIGS. 26A-26R, there is shown another embodiment of a jaw mechanism of the invention (denoted "460b").

As discussed in detail below, in addition to facilitating effective approximation, ligation and fixation of a myriad of soft tissue having a wide range of thicknesses and structure variations without collateral damage to extraneous soft tissue and bone structures, the jaw mechanism 460b is designed and configured to facilitate multiple seminal surgical functions, including highly effective and efficient means for (i) uncomplicated and highly reliable suture loading and retrieval with minimal visual guidance, (ii) optimal suture manipulation and retrieval in soft tissue in a confined surgical site, (iii) measurement of stitch placement positions in soft tissue in a confined surgical site for accurate and precise provision of complex stitch patterns, such as modified Mason-Allen stitch patterns, and (iv) capturing and engaging soft tissue, suture and surgical instruments in a confined surgical site with minimal visual guidance.

Additional advantages of the "multi-function" jaw mechanism 460b, which are also discussed below, include unique needle wear resistance means that increases the durability and longevity of a needle employed with the jaw mechanism 460b and a needle protection means that prevents breakage of the needle when subjected to high strain during a surgical procedure.

As illustrated in FIGS. 26A-26R, the multi-function jaw mechanism 460b similarly comprises top and bottom jaw members, in this instance, denoted 462a and 462b, respectively.

In a preferred embodiment, the multi-function jaw mechanism 460b also comprises a fixed pivot mechanism 458 that allows the jaw mechanism 460b to transition from a default open configuration, as described above and illustrated in FIG. 26A, which, as discussed below, facilitates receipt of sutures and soft tissue in the open jaw region (referred to hereinafter as the "internal jaw region 1000"), to a closed configuration, as illustrated in FIG. 26B, and back to the default open configuration via a jaw articulation control system of the invention.

In the noted embodiment, the fixed pivot mechanism 458 comprises (i) a first pin 453, which is sized and configured to be positioned in a first pin lumen in the top jaw member 462a and a second pin lumen in link 452b, (ii) a second pin 455, which is sized and configured to be positioned in a third pin lumen in the top jaw member 462a and a fourth pin lumen in the bottom jaw member 462b, and (iii) a third pin 459, which is sized and configured to be positioned in a fifth pin lumen in the bottom jaw member 462b, a sixth pin lumen in link 452b, and a seventh pin lumen in the distal end of the driver support rod 416 (shown in FIGS. 26M and 26N).

As illustrated in FIGS. 26A and 26B, the bottom jaw member 462b comprises a proximal end 473a, a distal end 473b, and a suture engagement region 489a and a tissue/suture engagement region 489b disposed on the distal end 473b of the bottom jaw member 462b.

As illustrated in FIGS. 26A and 26C-26E, the suture engagement region 489a comprises a raised proximal suture guide region 482, a raised distal guide region (denoted "475a", "475b" and "475c") and a suture loading or receiving slot 472 disposed therebetween.

As illustrated in FIGS. 26C-26E, the raised distal guide regions 475a, 475b, 475c comprise a distal tissue guide region 477 and a proximal suture guide region (denoted "480a", "480b" and "480c").

As further illustrated in FIGS. 26C-26E and discussed in detail below, each proximal suture guide region 480a, 480b, 480c comprises a different configuration to cooperate with the top jaw member 462a, as discussed below.

In a preferred embodiment, the outer edges of the raised distal guide regions 475a, 475b, 475c and, hence, proximal suture guide regions 480a, 480b, 480c thereof, and outer edges of raised proximal suture guide region 482 comprise rounded configurations to eliminate snagging of sutures thereon.

According to the invention, the outer surfaces of the raised distal guide regions 475a, 475b, 475c and, hence, proximal suture guide regions 480a, 480b, 480c thereof, and outer edges of raised proximal suture guide region 482 can further comprise curved or convex (or curvilinear) configurations to further abate snagging of sutures thereon.

As illustrated in FIG. 26R and discussed in detail below, the suture receiving slot 472 is sized and configured to slidably receive a suture therein, whereby, a suture, such as suture 71, can be readily loaded therein transversely or, as discussed below, as a loop, as illustrated in FIG. 26O.

As further illustrated in FIGS. 26O and 26P, the suture receiving slot 472 comprises a suture seat 483 that is sized and configured to receive, position and releasably secure a suture, such as suture 71, in the suture receiving slot 472. As discussed below, suture seat 483 defines a needle engagement and tissue stitch point.

As illustrated in FIG. 26M, the bottom jaw member 462b further comprises a continuous needle guide channel 478 that runs from the elongated shaft 410 of the suture passer device 400, into and through the bottom jaw member window 470b, and transects the suture loading slot 472.

In a preferred embodiment, the needle guide channel 478 is sized and configured to receive a needle of the invention; preferably, needle 170, therein and allow translation of the needle therethrough and articulation of the needle therein.

In a preferred embodiment, the needle guide channel 478 is positioned in the bottom jaw member 462b, whereby, a suture disposed in the suture loading slot 472 can be engaged by the needle 170 when the needle 170 slidably translates through and articulates in the needle guide channel 478.

As illustrated in FIG. 26V, in a preferred embodiment, the needle guide channel 478 comprises an open structure.

As illustrated in FIGS. 26A and 26B, the top jaw member 462a comprises a proximal end 474a and a distal end 474b.

Referring now to FIGS. 26I and 26J, in some embodiments, the top jaw member 462a comprises a raised or projecting guide region (denoted "490a" and "490b") that is disposed on the distal end 474b of the top jaw member 462a.

As illustrated in FIGS. 26I and 26J, the projecting guide regions 490a, 490b comprise a proximal end 497a, a distal end 497b, and a tissue/suture engagement region 489c disposed on the distal end 497b.

As further illustrated in FIGS. 26I and 26J, the projecting guide regions 490a, 490b of the top jaw member 462a further comprise a suture guide region (denoted "498a" and "498b") disposed on the proximal end 497a of the projecting guide regions 490a, 490b.

According to the invention, the suture guide region of the projecting guide regions 490a, 490b can comprise various shapes.

As illustrated in FIGS. 26A-26B, 26F-26G and 26I, in some embodiments, suture guide region 498a comprises a substantially planar shape.

In a preferred embodiment, the suture guide region of the projecting guide regions 490a, 490b comprise a curvilinear shape, such as suture guide region 498b illustrated in FIG. 26J, and FIGS. 37 and 38 of priority U.S. Provisional App. No. 63/766,960, which is expressly incorporated by reference herein in its entirety.

As further illustrated in FIGS. 26M and 26N, the top jaw member 462a further comprises a top jaw member window 470a that is sized and configured to allow needle 170 (not shown) to traverse therethrough.

As illustrated in FIGS. 26F-26H, top jaw member window 470a is further sized and configured to receive and seat the suture engagement region 489a of the bottom jaw member 462b, whereby, as illustrated in FIGS. 26F-26K, a suture containment region 491 is provided when the multi-function jaw mechanism 460b is in a closed configuration.

Referring back to FIGS. 26F-26H, in a preferred embodiment, when the multi-function jaw mechanism 460b is in a closed configuration and the suture engagement region 489a of the bottom jaw member 462b is seated in the top jaw member window 470a, a gap 499 is provided between the top jaw member 462a and the proximal suture guide region 482 of the suture engagement region 489a and, hence, bottom jaw member 462b, which allows a suture, such as suture 71, to be translated in a distal direction into the suture containment region 491.

In a preferred embodiment, the gap 499 comprises a distance of 0.25 mm.

In a preferred embodiment, when the multi-function jaw mechanism 460b is in a closed configuration and the suture engagement region 489a of the bottom jaw member 462b is seated in the top jaw member window 470a, a suture backstop region (denoted "BR") is formed in the suture containment region 491, which abates translation of a suture, such as suture 71, in a distal direction.

In some embodiments, the projecting guide region 490a of the top jaw member 462a forms the suture backstop region (BR), such as illustrated in FIG. 26H.

In some embodiments, the projecting guide region 490b of the top jaw member 462a forms the suture backstop region (BR), such as illustrated in FIG. 26J.

In some embodiments, the suture engagement region 489a of the bottom jaw member 462b forms the suture backstop region (BR), such as illustrated in FIGS. 26F and 26K.

In some embodiments, the projecting guide region 490a of the top jaw member 462a and the suture engagement region 489*a* of the bottom jaw member 462*b* form the suture backstop region (BR), such as illustrated in FIGS. 26G and 26I.

In some embodiments, the projecting guide region 490*b* of the top jaw member 462*a* and the suture engagement region 489*a* of the bottom jaw member 462*b* form the suture backstop region (BR).

In a preferred embodiment, the outer edges of the proximal end regions of the projecting guide regions 490*a*, 490*b* of the top jaw member 462*a* similarly comprise rounded configurations to eliminate snagging of sutures thereon.

According to the invention, the outer surfaces of the proximal end regions of the projecting guide regions 490*a*, 490*b* of the top jaw member 462*a* can similarly further comprise curved or convex (or curvilinear) configurations to further abate snagging of sutures thereon.

As discussed in detail below, the backstop region (BR) and suture engagement region 489*a* of the bottom jaw member 462*b* jointly facilitate several seminal functions and, hence, features of the "multi-function" jaw mechanism 460*b*; particularly, uncomplicated and highly reliable suture loading and retrieval with minimal visual guidance.

Referring now to FIGS. 26O-26R, operation of the multi-function jaw mechanism 460*b* will be described in detail below.

Referring first to FIG. 26O, in accordance with one preferred procedure for loading suture into the multi-function jaw mechanism 460*b*, a loop of suture, in this instance, suture 71, is initially guided into the internal jaw region 1000 defined by the top and bottom jaw members 462*a*, 462*b* of the jaw mechanism 460*b*.

After the loop of suture 71 is guided into the internal jaw region 1000, the jaw mechanism 460*b* is induced to transition from the default open configuration illustrated in FIG. 26O, to a closed configuration, as illustrated in FIG. 26P, via a jaw articulation control system of the invention, whereby the loop of suture 71 is entrapped in the internal jaw region 1000.

After the jaw mechanism 460*b* is positioned in the closed configuration with the suture 71 entrapped in the internal jaw region 1000, the loop of suture 71 is manually drawn in a distal direction toward the suture containment region 491, as denoted by arrow "Sai" in FIG. 26Q, until, as discussed below, the suture 71 abuts against the backstop region (BR) of the jaw mechanism 460*b*, wherein further distal translation of the suture 71 is abated.

After distal translation of the suture 71 is abated by the backstop region (BR) of the jaw mechanism 460*b*, the suture 71 is manually drawn in a proximal inferior direction, as denoted by arrow "$S_{d2}$" in FIG. 26R, wherein the backstop region (BR) and the suture engagement region 489*a* guide the suture 71 into the suture receiving slot 472 and suture seat 483 thereof, whereby, as discussed below, the suture 71 is in a position to be captured by the system needle 170 and passed into and through target soft tissue.

According to the invention, the suture 71 can be captured by the system needle 170 and directed into and through a target suture site in the soft tissue by transitioning the jaw mechanism 460*b* back to the open configuration, positioning the jaw mechanism 460*b* at the target soft tissue site, positioning the soft tissue in the internal jaw region 1000 of the jaw mechanism 460*b*, capturing the soft tissue with the jaw mechanism 460*b* by transitioning the jaw mechanism 460*b* back to the closed configuration, and inducing translation of the system needle 170 through and out of the jaw mechanism 460*b* and into the soft tissue.

After the suture 71 is passed into and through the soft tissue, the system needle 170 is retracted and the jaw mechanism 460*b* is transitioned back to the default open configuration, wherein the soft tissue is released with a portion of the suture 71 engaged thereto and a portion of the suture 71, i.e., free end, engaged to the jaw mechanism 460*b* via suture retaining ribbon (which is shown in phantom in FIG. 26M, and denoted "450"), which is induced to slidably translate through ribbon slot 454 of the top jaw member 462*a* toward the distal end 474*b* and into the suture ensnarement region 479 thereof (which is disposed in the distal wall 496 of the window 470*a*) by a suture control system of the invention. The suture passing system is thereafter withdrawn from the soft tissue site with the free end of the suture 71 engaged to the jaw mechanism 460*b*.

After the suture passing device is withdrawn from the soft tissue site, the free end of the suture 71 is released from the jaw mechanism 460*b*. The suture 71 can then be reloaded into the jaw mechanism 460*b* and directed into and through a second target suture site in the soft tissue in the same manner as discussed above to facilitate the provision of various stitch patterns at the surgical site; particularly, Mason-Allen and modified Mason-Allen stitch patterns, including the Mason-Allen and modified Mason-Allen stitch patterns illustrated in FIGS. 26S and 26T, and denoted "1010" and "1020", respectively.

By virtue of the optimal suture manipulation provided by the jaw mechanism 460*b*, various additional stitch patterns can be precisely formed in soft tissue, including, without limitation, mattress, sliding mattress, far-near-near-far, Bunnell-Mayer, three-loop pulley, locking loop, modified Kessler, simple interrupted, simple continuous, Ford interlocking, interrupted cruciate, interrupted horizontal mattress, continuous horizontal mattress, interrupted vertical mattress, quilled, interrupted or continuous Lembert, interrupted quilt, Cushing, Connel, Parker-Kerr, purse string stitch patterns and modified variants thereof.

As indicated above, an additional surgical function and, hence, feature of the jaw mechanism 460*b* comprises means for separately and effectively capturing and engaging soft tissue (prior to and after passage of suture therethrough) and surgical instruments, such as tissue graspers and suture retrievers, at and within a confined surgical site with minimal visual guidance.

According to the invention, the jaw mechanism 460*b* is also preferably adapted to engage and capture suture within a confined surgical site with minimal visual guidance. According to the invention, the suture can comprise the same or first suture passed through soft tissue and retained by the jaw mechanism 460*b* and other suture while the first suture is retained by the jaw mechanism 460*b*, i.e., static and dynamic suture capture.

In a preferred embodiment, to facilitate the soft tissue, suture and surgical apparatus engagement and capture function(s), the top and bottom jaw members 462*a*, 462*b* comprise tissue/suture engagement regions (denoted "489*c*" and "489*b*", respectively, in FIG. 26A).

As illustrated in FIG. 26A, in some embodiments, the tissue/suture engagement region 489*c* of the top jaw member 462*a* comprises projecting top jaw member region 490*a*.

As illustrated in FIG. 26J, in some embodiments, the tissue/suture engagement region 489*c* of the top jaw member 462*a* comprises projecting top jaw member region 490*b*.

As illustrated in FIG. 26K, in some embodiments, the tissue/suture engagement region 489*c* of the top jaw member 462*a* merely comprises a planar tissue/suture engagement region (denoted "490*c*").

As illustrated in FIGS. 26A and 26B and FIGS. 26F-26K, in one preferred embodiment, the tissue/suture engagement region 489c of the top jaw member 462a comprises a tissue/suture engaging surface 495a and the tissue/suture engagement region 489b of the bottom jaw member 462b comprises a mating tissue/suture engaging surface 495b.

As illustrated in FIGS. 26B, 26F and 26K, in a preferred embodiment, the tissue/suture engaging surfaces 495a, 495b are positioned on the top and bottom jaw members 462a, 462b, wherein the tissue/suture engaging surfaces 495a, 495b are aligned when the multi-function jaw mechanism 460b is in a closed configuration (shown in phantom in FIG. 26K) and, as illustrated in FIG. 26U, during transition of the multi-function jaw mechanism 460b to the closed configuration, the tissue/suture engagement regions 489b, 489c of the top and bottom jaw members 462a, 462b provide a tissue capture region (denoted "471" in FIG. 26U), which is configured to receive and, hence, facilitate capture and engagement of soft tissue, sutures and surgical instruments therein.

According to the invention, the surface of the tissue/suture engaging surface 495a of the top jaw member 462a can comprise various surface features to facilitate capture and engagement of soft tissue, sutures and surgical instruments between the tissue/suture engaging surfaces 495a, 495b. As illustrated in FIGS. 26A and 26B, and FIGS. 26F-26J, in one preferred embodiment, the tissue/suture engaging surface 495a of the top jaw member 462a comprises a serrated surface 488.

According to the invention, the surface of the tissue/suture engaging surface 495b of the bottom jaw member 462b can similarly comprise various surface features to similarly facilitate engagement of capture and engagement of soft tissue, sutures and surgical instruments between the tissue/suture engaging surfaces 495a, 495b, such as a plurality of reciprocating serrations that are sized and configured to interlock with the serrated surface 488 of the tissue/suture engagement surface 495a of the top jaw member 462a, or simply comprise a substantially flat or planar surface, as illustrated in FIGS. 26A and 26B, and FIGS. 26F-26J.

In a preferred embodiment, the distal ends 474b, 473b of the top and bottom jaw members 462a, 462b and hence, tissue/suture engaging surfaces 495a, 495b are configured and adapted to engage and capture fine sutures and a portion thereof, and defined, finite portions of tissue proximate the distal ends 474b, 473b of the top and bottom jaw members 462a, 462b and hence, tissue engaging surfaces 495a, 495b within a confined surgical site.

Thus, in a preferred embodiment, when the multi-function jaw mechanism 460b is in a closed configuration, at least the distal ends 474b, 473b of the top and bottom jaw members 462a, 462b and hence, tissue/suture engaging surfaces 495a, 495b are in contact.

As further illustrated in FIGS. 26A and 26B, and FIGS. 26F-26K, in at least one embodiment, when the multi-function jaw mechanism 460b is in a closed configuration, at least 10% of the tissue/suture engaging surfaces 495a, 495b extending from the distal ends 474b, 473b of the top and bottom jaw members 462a, 462b and hence, tissue/suture engaging surfaces 495a, 495b are in contact.

As illustrated in FIGS. 26C-26E and 26U and indicated above, in a preferred embodiment, the raised distal guide regions 475a, 475b, 475c of the bottom jaw member 462b comprise a distal tissue guide region 477, which is sized and configured to position the portion of soft tissue in the tissue capture region 471 when the portion of the soft tissue is advanced therein.

In a preferred embodiment, systems of the invention employing the multi-function jaw mechanism 460b similarly comprise (i) a jaw articulation control system that is adapted to modulate articulation of jaw mechanism 460b, (ii) a needle articulation control system that is adapted to modulate articulation of needle 170, and a suture control system that is adapted to modulate engagement, retainment and release of suture 71.

Preferred jaw articulation control systems, needle articulation control systems and suture control systems are described in detail in Applicant's priority U.S. application Ser. No. 18/623,903, which is expressly incorporated herein in its entirety.

In a preferred embodiment, the suture passing systems also comprise a multi-function actuation system that is configured to control the jaw articulation control system, needle articulation control system and suture control system.

Preferred multi-function actuation systems similarly comprise the multi-function actuation systems (denoted "405" and "505") that are described in detail in U.S. application Ser. No. 18/623,903.

According to the invention, control of jaw mechanism 460b, needle 170 and suture engagement, retainment and release by the suture passing systems of the invention can also be provided via robotic systems.

By way of example, in some embodiments, a robotic system comprises at least one robotic interface or manipulator configured and adapted to interface with a suture passing system of the invention, such as suture passing system 400, and, hence, jaw mechanism 460b, and a control system comprising programming means and associated algorithms adapted to control the robotic interface, whereby, at least the following synchronized functions are provided: axial articulation of the jaw mechanism 460b, needle articulation, and suture control, including access of suture into the open internal jaw region of the jaw mechanism 460b, releasable engagement of the suture by the needle, and release of the suture by the needle.

According to the invention, the suture passing systems of the invention can also be adapted and configured to operate in conjunction with commercial robotic surgical systems, such as the da Vinci surgical systems (Intuitive Surgical), Hugo robotic-assisted surgery systems (Medtronic), and Versius surgical systems (CMR Surgical).

As indicated above, an additional surgical function and, hence, feature of the multi-function jaw mechanism 460b comprises means for measuring stitch placement positions in soft tissue for accurate and precise provision of complex stitch patterns, such as the modified Mason-Allen stitch pattern illustrated in FIG. 26T.

Referring to FIGS. 26A, 26B and 26N, in some embodiments, the means for measuring stitch placement positions in soft tissue comprises a first plurality of markers 485a disposed on a lateral side 463c or 463d of the bottom jaw member 462b that are defined distances from the suture loading slot 472 and, hence, needle engagement and stitch point referenced above.

In some embodiments, the means for measuring stitch placement positions in soft tissue further comprises a second plurality of markers 485b disposed on an opposing lateral side 463a or 463b of the top jaw member 462a, wherein the first and second plurality of markers 485a, 485b are aligned when the multi-function jaw mechanism 460b is in a closed configuration.

In a preferred embodiment, the first plurality of markers 485a is disposed on both lateral sides, i.e., lateral sides 463c and 463d, of the bottom jaw member 462b and the second plurality of markers 485b is disposed on both lateral sides, i.e., lateral sides 463a or 463b, of the top jaw member 462a, the first and second plurality of markers 485a, 485b being similarly aligned when the multi-function jaw mechanism 460b is in a closed configuration.

According to the invention, the distance from a border of soft tissue captured in the internal jaw region 1000 to a desired stitch position in the soft tissue, e.g., "$d_2$" in FIG. 26B can be determined and realized by advancing the border of the soft tissue into the internal jaw region 1000 of the jaw mechanism 460b and aligning the border of the soft tissue with a desired marker of the first or second plurality of markers 485a, 485b.

According to the invention, the markers 485a, 485b can comprise any suitable form, such as printed markers, engraved markers, radiopaque markers, and any combination thereof, e.g., printed and engraved markers.

As will be readily appreciated by one having ordinary skill in the art, the multi-function jaw mechanism 460b thus facilitates multiple seminal surgical functions, including highly effective and efficient means for (i) uncomplicated and highly reliable suture loading with minimal visual guidance, (ii) optimal suture manipulation and retrieval in soft tissue in a confined surgical site, (iii) measurement of stitch placement positions in soft tissue in a confined surgical site for accurate and precise provision of complex stitch patterns, such as modified Mason-Allen stitch patterns, and (iv) engaging and capturing soft tissue, suture and surgical instruments in a confined surgical site with minimal visual guidance.

The suture passing systems of the invention employing the multi-function jaw mechanism 460b thus obviate the need for various multiple surgical instruments, such as tissue graspers and suture retrievers, which are typically employed during a surgical procedure.

As further indicated above, additional features and advantages of the multi-function jaw mechanism 460b comprise (i) unique needle wear resistance means that increases the durability and longevity of a needle employed with the jaw mechanism 460b and (ii) needle protection means that prevents breakage of the needle 170; particularly, the needle tip (or suture ensnarement end 171), when subjected to high strain.

Referring now to FIG. 26W, in a preferred embodiment, the needle wear resistance means comprises two (2) wear resistance members that are positioned and configured to abut the outer surface of the needle employed within the jaw mechanism 460b, in this instance, needle 170, at defined needle abutment points (denoted $AP_1$, $AP_2$ in FIG. 26W) when the needle 170 is slidably translated through the needle guide channel 478.

As illustrated in FIG. 26W, in a preferred embodiment, a first wear resistance member 484 is disposed proximate the distal end 473b of the bottom jaw member 462b, i.e., at needle abutment point $AP_1$, and a second wear resistance member 486 is disposed on the bottom surface of the bottom jaw member 462b proximate the proximal end 473a thereof and transects the bottom jaw member window 470b, i.e., at needle abutment point $AP_2$.

According to the invention, the first and second wear resistance members 484, 486 can comprise any suitable size and shape. As illustrated in FIGS. 26W and 26X, in a preferred embodiment, the first wear resistance member 484 comprises a cylindrical-shaped pin member, which, as discussed below, preferably comprises a metal or metal alloy subjected to a cold-working process that enhances hardening of at least the surface region 487a and, thereby wear resistance and friction reduction of the wear resistance "pin" member 484.

As illustrated in FIGS. 26W and 26Y, in a preferred embodiment, the second wear resistance member 486 comprises a partial cylindrical-shaped structure. In a preferred embodiment, the second wear resistance member 486 is formed from a cylindrical-shaped pin structure, which has similarly been subjected to a cold-working process that enhances hardening of the surface region. As further illustrated in FIGS. 26W and 26Y, after the cylindrical-shaped pin structure is subjected to the cold-working process, the cylindrical-shaped pin structure is further fabricated to form the illustrated partial cylindrical-shaped structure to minimize the profile size, while the critical work hardened surface 487b, which will interface with the needle 170, remains intact.

Referring now to FIG. 26Z, in some embodiments, the second wear resistance member (now denoted "492") comprises a wedge-shaped insert member comprising a top needle abutment surface 493. In a preferred embodiment of the invention, the "wedge-shaped" wear resistance member 492 is similarly comprises a cold-worked metal or metal alloy, i.e., a surface hardened sheet.

According to the invention, the "wedge-shaped" wear resistance member 492 can also be subjected to a forming process to form the rounded distal end 494b, and a subsequent process to minimize the profile size with the hardened surface remaining intact and providing enhanced wear resistance and friction reduction.

As indicated above, in a preferred embodiment, the wear resistance members 484, 486, 492 comprise a metal or metal alloy subjected to a cold-working process, i.e., a work-hardened metal or metal alloy, that enhances hardening and, thereby wear resistance and friction reduction of the wear resistance members 484, 486, 492; particularly, the surfaces thereof.

According to the invention, suitable metals and metal alloys include, without limitation, stainless steel and alloys thereof; particularly, nitrogen-strengthened (austenitic) stainless-steel alloys (e.g., Nitronic 60 and Nitronic 30), nickel-chromium-iron alloys (e.g., Inconel 625) and cobalt-chromium-nickel alloys (e.g., Elgaloy 60).

In a preferred embodiment, the wear resistance members 484, 486, 492 comprise cold-worked Nitronic 60 or Elgaloy 60.

According to the invention, the wear resistance members 484, 486, 492 can also comprise various polymeric materials comprising low wear rates and/or coefficients of friction, such as, without limitation, acetal, nylon, ultra-high molecular weight polyethylene (UHMW-PE), polyphenylene sulfide (PPS), polyether ether ketone (PEEK) and polyamide-imide (PAI).

According to the invention, to further enhance wear resistance of the wear resistance members 484, 486, 492 and, hence, durability and longevity of a needle employed with the jaw mechanism 460b, the wear resistance members 484, 486, 492 can further comprise a surface coating that further lowers the coefficient of friction and, hence, wear rate.

According to the invention, suitable friction abatement coatings comprise, without limitation, diamond-like carbon (DLC) materials, graphene-based coatings, synthetic fluoropolymers and combinations thereof.

According to the invention, other components of the suture passing systems of the invention, such as needle 170 and surfaces (which are collectively denoted "481" in FIGS. 26M and 26W) of needle guide channel 478, can also comprise one or more of the aforementioned friction abatement coatings.

According to the invention, components of the suture passing systems of the invention, such as top and bottom jaw members 462a, 462b, can also comprise an anti-reflective coating, e.g., a cerium oxide ($CeO_2$) or $CeO_2$-based coating, to prevent glare, such as arthroscope glare, during a surgical procedure to facilitate visualization within a surgical site.

According to the invention, the outer coatings can also comprise various pharmaceutical agents, including, without limitation, antibiotics, anti-microbial agents, anti-viral agents, analgesic agents, anti-inflammatory agents, antineoplastic agents, anti-spasmodic agents, anticoagulant agents and agents that modulate proliferation and growth of tissue.

As indicated above, an additional feature and advantage of the multi-function jaw mechanism 460b comprises needle protection means that prevents breakage of the needle when subjected to high strain during a surgical procedure.

According to the invention, the needle protection means is provided via the uniquely configured needle guide channel 478.

Referring back to FIG. 26W, in a preferred embodiment, when slidable translation of the needle 170 is induced through the guide channel 478 and the suture ensnarement end 171 of the needle 170 abuts a semi-penetrable or impenetrable object, the "open" needle guide channel 478 allows needle 170 to flex (or bend) at abutment points $AP_1$, $AP_2$ and, hence, prevent fracture and/or breakage of the needle 170 at the suture ensnarement end 171, and thus prevent small fragments of the needle 170 from being introduced into the surgical site.

An additional feature of the multi-function jaw mechanism 460b is that the jaw mechanism 460b is readily adapted to receive and advance virtually all conventional sutures into and through various soft tissues and soft tissue structures, including, without limitation, the HS-Fiber Suture Implants developed by Tensor Surgical, Inc. (NV) and various additional sutures comprising biodegradable polymers; particularly, poly(glycerol sebacate) (PGS) and derivatives thereof, such as poly(glycerol-co-sebacate) acrylate (PGSA).

As set forth in Yu, et al., *Development of Poly (Glycerol Sebacate) and its Derivatives: A Review of the Progress Over the Past Two Decades*, Polymer Reviews, vol. 63, no. 3, pp. 613-678 (2023) and Wu, et al., *A Review: Optimization for Poly (Glycerol Sebacate) and Fabrication Techniques for its Centered Scaffolds*, Macromolecular Bioscience, vol. 21, no. 9, pg. 2100022 (2021), PGS and derivatives thereof possess a plurality of unique structural and chemical properties, whereby PGS and its derivatives induce remodeling of damaged soft tissue and bone tissue and structures, and, hence, healing thereof, when disposed proximate thereto.

As will readily be appreciated by one having ordinary skill in the art, the suture passing systems, apparatus and methods of the invention thus provide numerous advantages compared to prior art systems, apparatus and methods for passing suture through soft tissue and soft tissue structures. Among the advantages are the following:

The provision of highly reliable suture passing systems, apparatus and associated methods that can be readily employed to effectively approximate, ligate, fixate soft tissue and soft tissue structures and/or close soft tissue structures;

The provision of suture passing systems, apparatus and associated methods that can be readily employed to pass suture into and through soft tissue and soft tissue structures without collateral damage to extraneous soft tissue and bone structures;

The provision of suture passing systems, apparatus and associated methods that provide an enhanced degree of control of soft tissue and soft tissue structure engagement, needle articulation and suture manipulation by an operator with minimal complexity;

The provision of suture passing systems, apparatus and associated methods that enable an operator to load suture with greater case and efficiency compared to conventional suture passing systems;

The provision of suture passing systems, apparatus and associated methods that provide enhanced suture manipulation in a confined surgical site with minimal visual guidance;

The provision of suture passing systems, apparatus and associated methods that enable an operator to precisely measure stitch placement locations in soft tissue and soft tissue structures in a confined surgical site for accurate and precise provision of complex stitch patterns, such as modified Mason-Allen stitch patterns;

The provision of suture passing systems, apparatus and associated methods that can be readily employed to effectively capture and engage soft tissue, soft tissue structures and surgical instruments within a confined surgical site;

The provision of suture passing systems, apparatus and associated methods that provide enhanced needle durability over thousands of cycles of suture passing in and through soft tissue and soft tissue structures;

The provision of suture passing systems and apparatus that can be readily employed to endure multiple use cycles with limited impact on suture passing efficacy;

The provision of suture passing systems, apparatus and associated methods that prevent needle breakage in a surgical site during a surgical procedure; and The provision of suture passing systems, apparatus and associated methods that (i) enable an operator to load suture with greater case and efficiency compared to conventional suture passing systems, and (ii) provide enhanced suture manipulation and retrieval in a confined surgical site with minimal visual guidance, and (iii) enable an operator to precisely measure stitch placement locations in soft tissue and soft tissue structures in a confined surgical site for accurate and precise provision of complex stitch patterns, such as modified Mason-Allen stitch patterns, and (iv) can be readily employed to effectively capture and engage soft tissue, soft tissue structures and surgical instruments within a confined surgical site, and (v) provide enhanced needle durability over thousands of cycles of antegrade and retrograde passing of suture, and (vi) prevent needle breakage in a surgical site during a surgical procedure.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A multi-function jaw apparatus, comprising:

a jaw assembly comprising top and bottom jaw members, said top jaw member adapted to axially articulate with respect to said bottom jaw member, whereby said jaw assembly is adapted to transition from an open jaw configuration, wherein said top and bottom jaw members provide an open internal jaw region, to a closed jaw configuration, said open internal jaw region configured to receive a suture and soft tissue therein, said bottom jaw member comprising a bottom jaw member proximal end and a bottom jaw member distal end, said bottom jaw member further comprising a suture engagement region disposed on said bottom jaw member distal end, said suture engagement region comprising a raised proximal guide region, a raised distal guide region and a suture loading slot disposed between said raised proximal guide region and said raised distal guide region, said suture loading slot comprising a suture seat, said suture loading slot sized and configured to receive said suture therein and position said suture in said suture seat, said top jaw member and said bottom jaw member forming a suture containment region when said jaw assembly is in said closed jaw configuration, said top jaw member and said suture engagement region of said bottom jaw member forming a gap therebetween when said jaw assembly is in said closed jaw configuration, said gap sized to allow distal translation of said suture into said suture containment region when said jaw assembly is in said closed jaw configuration, said jaw assembly forming a suture backstop region in said suture containment region when said jaw assembly is in said closed jaw configuration, said suture backstop region configured to abate translation of said suture in a distal direction when said suture is disposed in said suture containment region.

2. The apparatus of claim 1, wherein said jaw assembly further comprises means for measuring a stitch placement location in said soft tissue when said soft tissue is positioned in said open internal jaw region of said jaw assembly.

3. The apparatus of claim 2, wherein said means for measuring a stitch placement location in said soft tissue comprises a first plurality of markers disposed on a first outer surface of said lower jaw mechanism, each of said first plurality of markers spaced a defined distance from said suture loading slot, whereby, when a border of said soft tissue is advanced into said open internal jaw region of said jaw assembly and aligned with a first marker of said first plurality of markers, a measurement of a first stitch placement location in said soft tissue is provided.

4. The apparatus of claim 3, wherein said means for measuring said stitch placement location in said soft tissue further comprises a second plurality of markers disposed on a second outer surface of said top jaw mechanism, said second plurality of markers positioned on said top jaw mechanism relative to said first plurality of markers, wherein said second plurality of markers and said first plurality of markers are aligned when said jaw assembly is in said closed jaw configuration.

5. A system for approximating and fixating soft tissue, comprising:

a needle comprising a tissue piercing distal end configured and adapted to releasably engage a suture and pierce into and through soft tissue with said suture said engaged thereto;

a multi-function jaw mechanism adapted to receive and cooperate with said needle, wherein said needle is allowed to articulate with respect to said jaw mechanism, said multi-function jaw mechanism comprising top and bottom jaw members, said top jaw member adapted to axially articulate with respect to said bottom jaw member, whereby said multi-function jaw mechanism is adapted to transition from an open jaw configuration, wherein said top and bottom jaw members provide an open internal jaw region, to a closed jaw configuration, said open internal jaw region configured to receive said suture and said soft tissue therein, said bottom jaw member comprising a bottom jaw member proximal end and a bottom jaw member distal end, said bottom jaw member further comprising a suture engagement region disposed on said bottom jaw member distal end, said suture engagement region comprising a raised proximal guide region, a raised distal guide region and a suture loading slot disposed between said raised proximal guide region and said raised distal guide region, said suture slot comprising a suture seat, said suture loading slot sized and configured to receive said suture therein and position said suture in said suture seat for said engagement by said needle, said top jaw member and said bottom jaw member forming a suture containment region when said multi-function jaw mechanism is in said closed jaw configuration, said top jaw member and said raised proximal guide region of said suture engagement region of said bottom jaw member forming a gap therebetween when said multi-function jaw mechanism is in said closed jaw configuration, said gap sized to allow distal translation of said suture into said suture containment region when said multi-function jaw mechanism is in said closed jaw configuration, said multi-function jaw mechanism forming a suture backstop region in said suture containment region when said multi-function jaw mechanism is in said closed jaw configuration, said suture backstop region configured to abate translation of said suture in a distal direction when said suture is disposed in said suture containment region; and system control means for synchronizing said axial articulation of said top jaw member and said needle articulation.

6. The system of claim 5, wherein said multi-function jaw mechanism further comprises means for measuring a stitch placement location in said soft tissue when said soft tissue is positioned in said open internal jaw region of said multi-function jaw mechanism.

7. The system of claim 6, wherein said means for measuring a stitch placement location in said soft tissue comprises a plurality of markers disposed on an outer surface of said lower jaw mechanism, each of said first plurality of markers spaced a defined distance from said suture loading slot, whereby, when a border of said soft tissue is advanced into said open internal jaw region of said multi-function jaw mechanism and aligned with a first marker of said plurality of markers, a measurement of a first stitch placement location in said soft tissue is provided.

8. The system of claim 5, wherein said bottom jaw member further comprises a needle guide channel sized and configured to receive said needle therein and allow slidable translation of said needle therethrough and articulation of said needle therein.

9. The system of claim 8, wherein said multi-function jaw mechanism further comprises needle wear resistance means for increasing durability and longevity of said needle.

10. The system of claim 9, wherein said needle wear resistance means comprises first and second wear resistance members.

11. The system of claim 10, wherein said first wear resistance member is disposed in said lower jaw mechanism at a first abutment point of said needle when said needle is said received in said needle guide channel, and said second wear resistance member is disposed in said lower jaw mechanism at a second abutment point of said needle when said needle is said received in said needle guide channel and said translated therethrough.

12. The system of claim 11, wherein said first and second wear resistance members comprise a work-hardened stainless-steel alloy.

13. The system of claim 12, wherein said work-hardened stainless-steel alloy comprises Nitronic 60.

14. The system of claim 11, wherein said first and second wear resistance members comprise a work-hardened cobalt-chromium-nickel alloy.

15. The system of claim 14, wherein said work-hardened cobalt-chromium-nickel alloy comprises Elgaloy 60.

16. The system of claim 5, wherein said multi-function jaw mechanism further comprises a suture control system adapted to control release of said suture by said needle.

\* \* \* \* \*